United States Patent
Hwang et al.

(10) Patent No.: US 11,257,985 B2
(45) Date of Patent: Feb. 22, 2022

(54) SEMICONDUCTOR ELEMENT AND SENSING DEVICE HAVING A LIGHT EMITTING UNIT AND A SENSOR UNIT

(71) Applicant: SUZHOU LEKIN SEMICONDUCTOR CO., LTD., Taicang (CN)

(72) Inventors: Deok Ki Hwang, Seoul (KR); Jae Hun Jeong, Seoul (KR); Ki Bum Sung, Seoul (KR); Sang Jun Park, Seoul (KR); Tae Yong Lee, Seoul (KR); Yong Han Jeon, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 209 days.

(21) Appl. No.: 16/466,953

(22) PCT Filed: Dec. 4, 2017

(86) PCT No.: PCT/KR2017/014100
§ 371 (c)(1),
(2) Date: Jun. 5, 2019

(87) PCT Pub. No.: WO2018/105975
PCT Pub. Date: Jun. 14, 2018

(65) Prior Publication Data
US 2020/0066936 A1 Feb. 27, 2020

(30) Foreign Application Priority Data

Dec. 5, 2016 (KR) .................. 10-2016-0164313
Dec. 5, 2016 (KR) .................. 10-2016-0164316
Dec. 15, 2016 (KR) .................. 10-2016-0171887

(51) Int. Cl.
*H01L 33/36* (2010.01)
*G01N 17/00* (2006.01)
(Continued)

(52) U.S. Cl.
CPC ............ *H01L 33/36* (2013.01); *G01N 17/004* (2013.01); *G01N 21/1702* (2013.01); *G01N 21/33* (2013.01); *G01N 2021/1704* (2013.01)

(58) Field of Classification Search
CPC ....... H01L 33/382; H01L 33/60; H01L 33/62; H01L 25/167; H01L 33/20; H01L 33/36;
(Continued)

(56) References Cited

U.S. PATENT DOCUMENTS 5,753,916 A * 5/1998 Ooisi ................. G01N 21/3504
250/339.03
8,393,196 B2 * 3/2013 Ikawa ................. G01N 27/128
73/31.06
(Continued)

FOREIGN PATENT DOCUMENTS

JP 2006-003153 A 1/2006
KR 10-2005-0005899 A 1/2005
(Continued)

*Primary Examiner* — Khiem D Nguyen
(74) *Attorney, Agent, or Firm* — Birch, Stewart, Kolasch & Birch, LLP

(57) ABSTRACT

A semiconductor device disclosed in an embodiment comprises: a light emitting unit comprising a light emitting structure layer which has a first conductivity type semiconductor layer, a second conductivity type semiconductor layer, and an active layer between the first conductivity type semiconductor layer and the second conductivity type semiconductor layer; and a sensor unit disposed on the light emitting unit, wherein the sensor unit comprises: a sensing material changing in resistance with light emitted by the light emitting unit; a first sensor electrode comprising a first pad portion and a first extension part extending from the first
(Continued)

pad portion and contacting the sensing material; and a second sensor electrode comprising a first pad portion and a second extension part extending toward the first extension part from the second pad portion and contacting the sensing material. The sensor unit senses an external gas in response to the light generated from the light emitting unit.

9 Claims, 43 Drawing Sheets

(51) Int. Cl.
     *G01N 21/17*           (2006.01)
     *G01N 21/33*           (2006.01)

(58) Field of Classification Search
     CPC ..... H01L 33/44; H01L 33/145; G01N 17/004; G01N 21/1702; G01N 21/33; G01N 2021/1704; G01N 21/1704; G01N 27/127; G01N 27/125; G01N 33/0031; G01N 33/0057
     USPC ............................................ 257/80; 250/551
     See application file for complete search history.

(56) References Cited

U.S. PATENT DOCUMENTS

| | | | |
|---|---|---|---|
| 9,064,773 B2* | 6/2015 | Cho | H01L 25/167 |
| 9,244,031 B2* | 1/2016 | Humbert | G01N 27/128 |
| 10,211,382 B2 | 2/2019 | Ahn et al. | |
| 2002/0142478 A1* | 10/2002 | Wado | G01N 27/124 436/151 |
| 2007/0062812 A1 | 3/2007 | Weber et al. | |
| 2007/0140908 A1* | 6/2007 | Mizuguchi | G01N 27/126 422/83 |
| 2008/0063566 A1* | 3/2008 | Matsumoto | G01N 27/4145 422/68.1 |
| 2010/0033723 A1* | 2/2010 | Thundat | G01N 21/1702 356/432 |
| 2010/0103421 A1* | 4/2010 | Johansen | G01N 21/03 356/367 |
| 2010/0147685 A1 | 6/2010 | Ikawa et al. | |
| 2012/0138959 A1* | 6/2012 | Tsang | H01L 25/167 257/80 |
| 2013/0059396 A1* | 3/2013 | LeBoeuf | G01N 27/414 436/149 |
| 2013/0273665 A1* | 10/2013 | Swager | G01N 33/0047 436/142 |
| 2016/0331289 A1* | 11/2016 | Kahlman | A61B 5/14552 |
| 2016/0351548 A1* | 12/2016 | Chen | H01L 25/0753 |
| 2017/0276627 A1* | 9/2017 | Dobrokhotov | G01N 33/0031 |
| 2018/0202956 A1* | 7/2018 | Hsieh | G08B 21/14 |

FOREIGN PATENT DOCUMENTS

| | | |
|---|---|---|
| KR | 10-2006-0055525 A | 5/2006 |
| KR | 10-2006-0110278 A | 10/2006 |
| KR | 10-2010-0101046 A | 9/2010 |
| KR | 10-2011-0027274 A | 3/2011 |
| KR | 10-1532557 B1 | 6/2015 |

* cited by examiner

[FIG. 1]
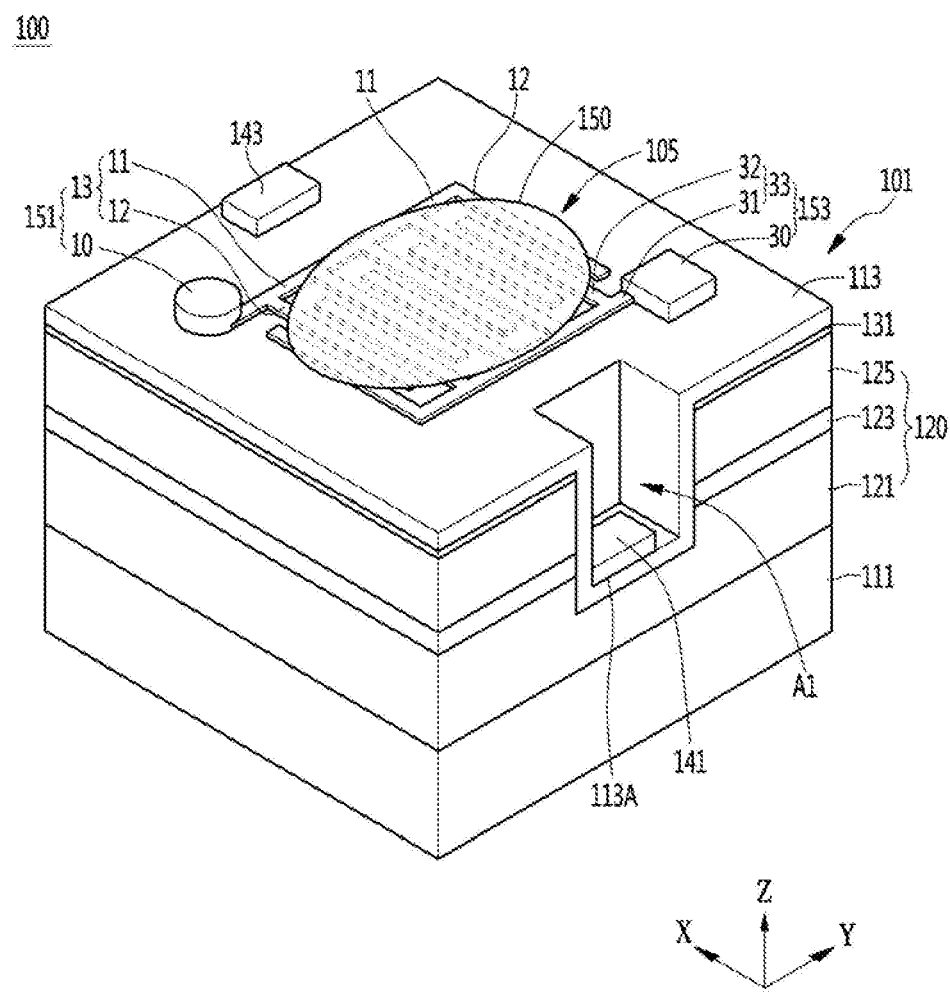

[FIG. 2]
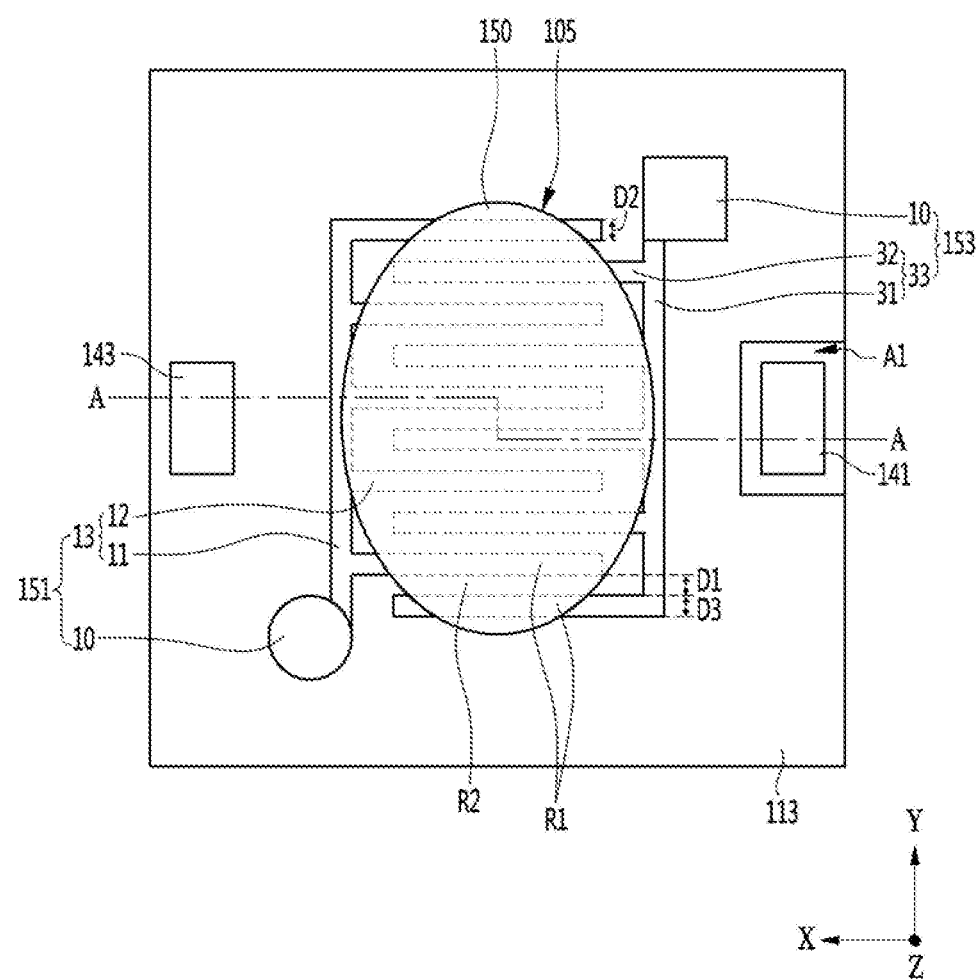

[FIG. 3]
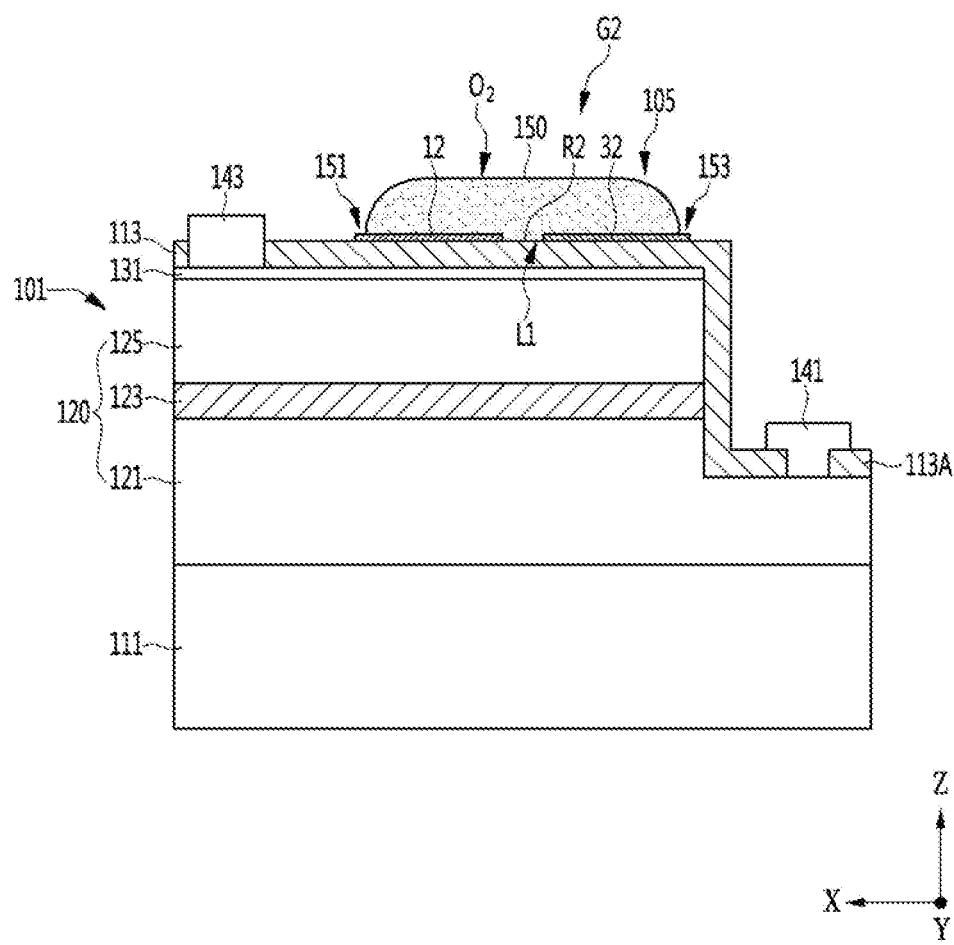

[FIG. 4]
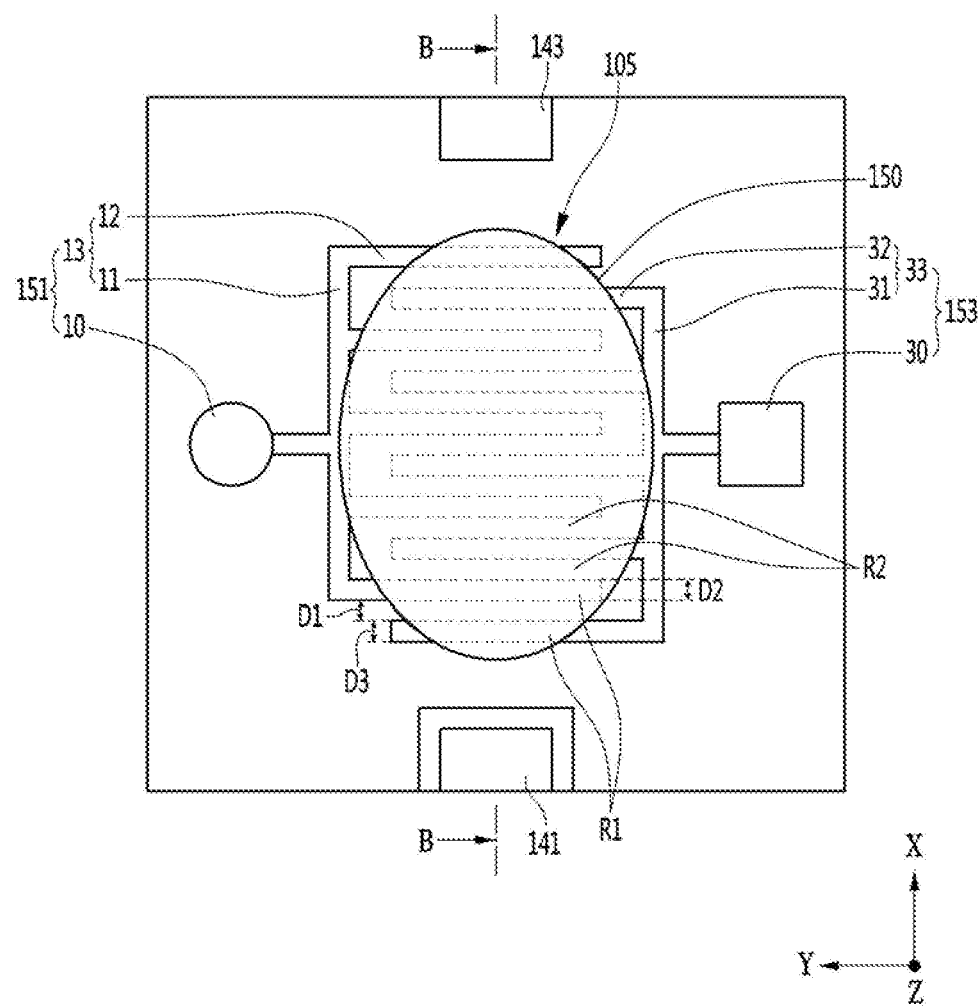

[FIG. 5]
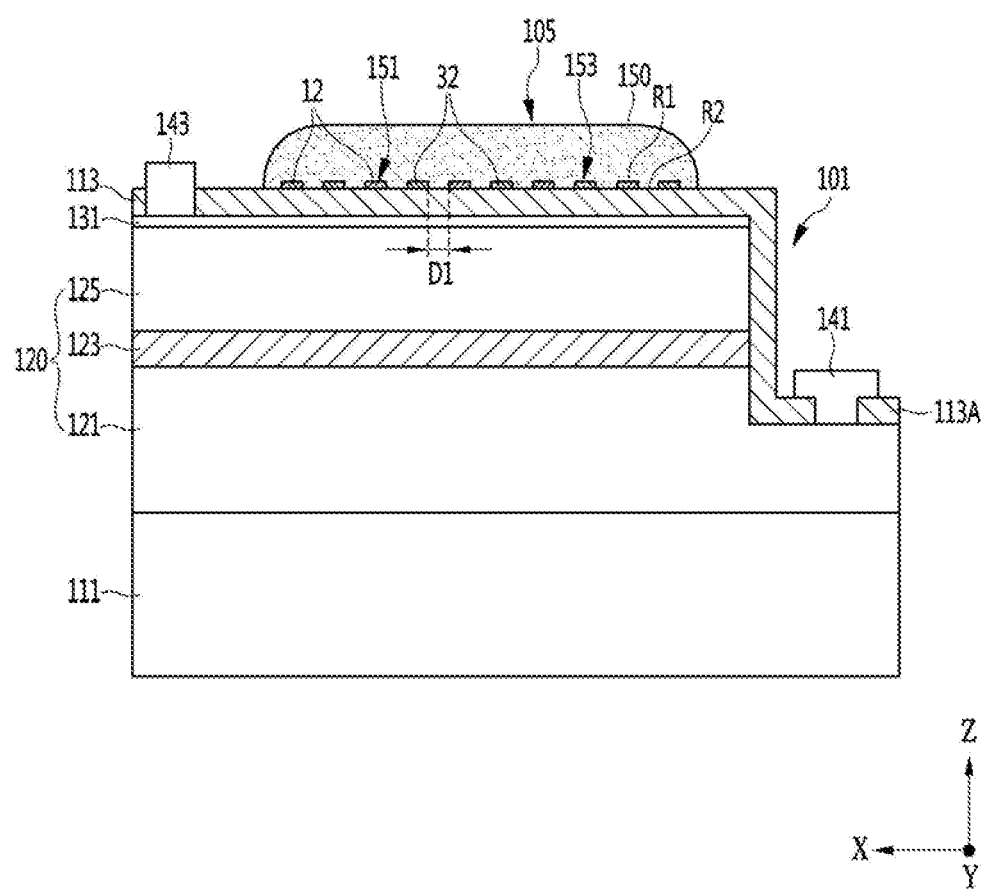

[FIG. 6]
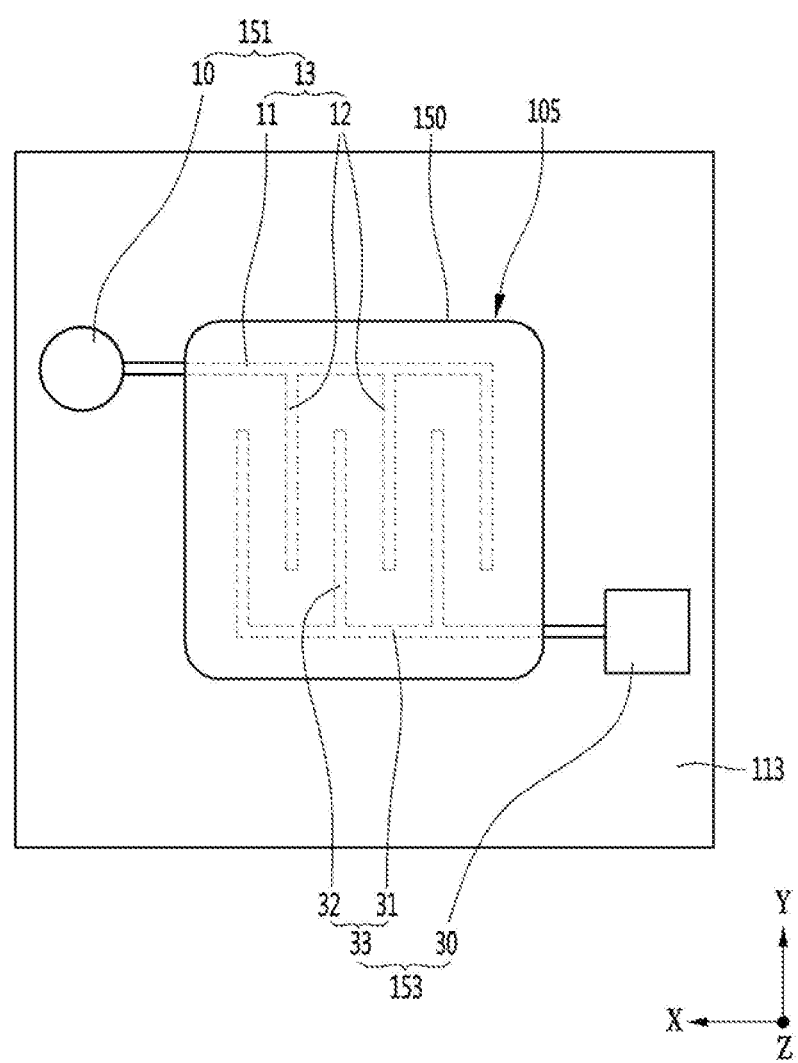

[FIG. 7]
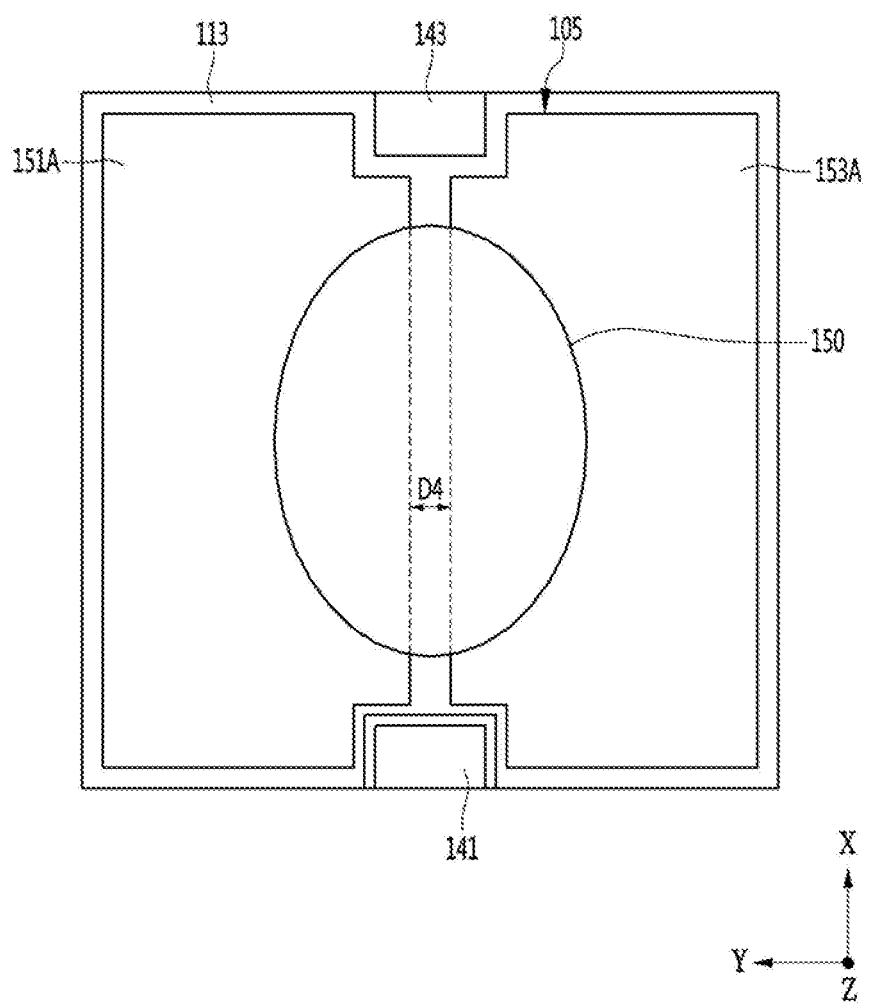

[FIG. 8]
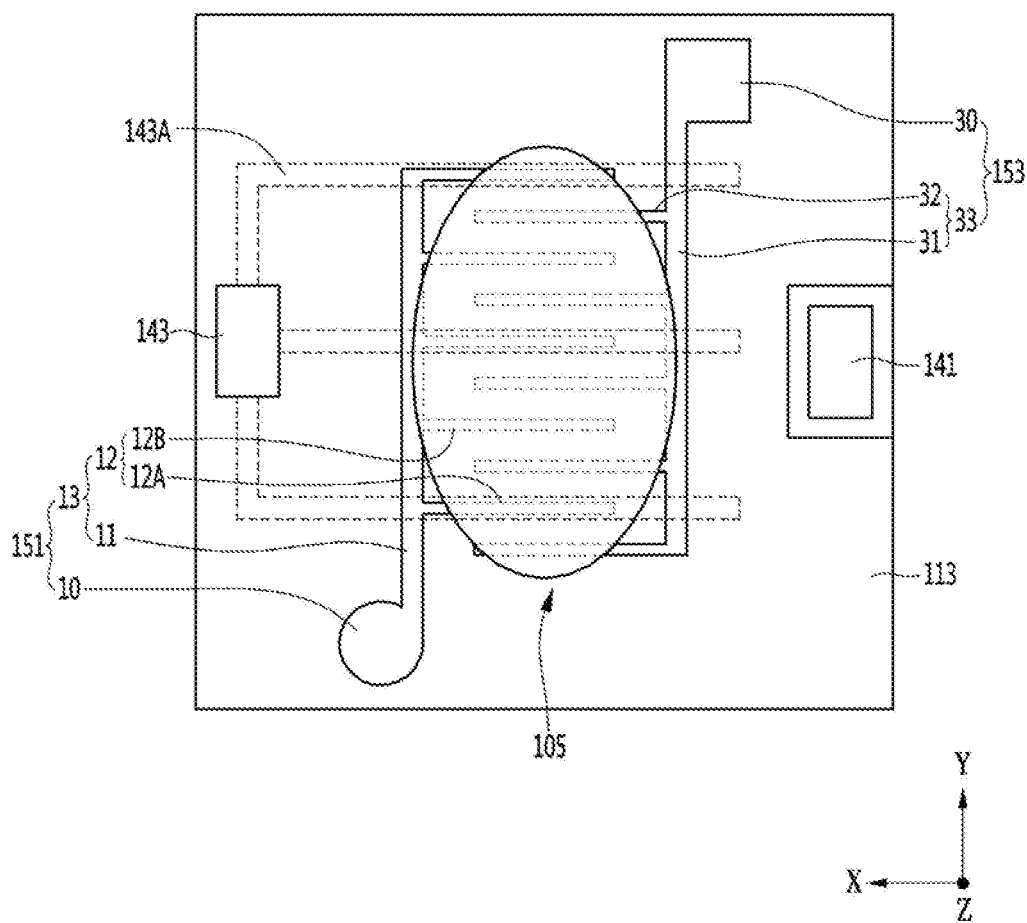

[FIG. 9]
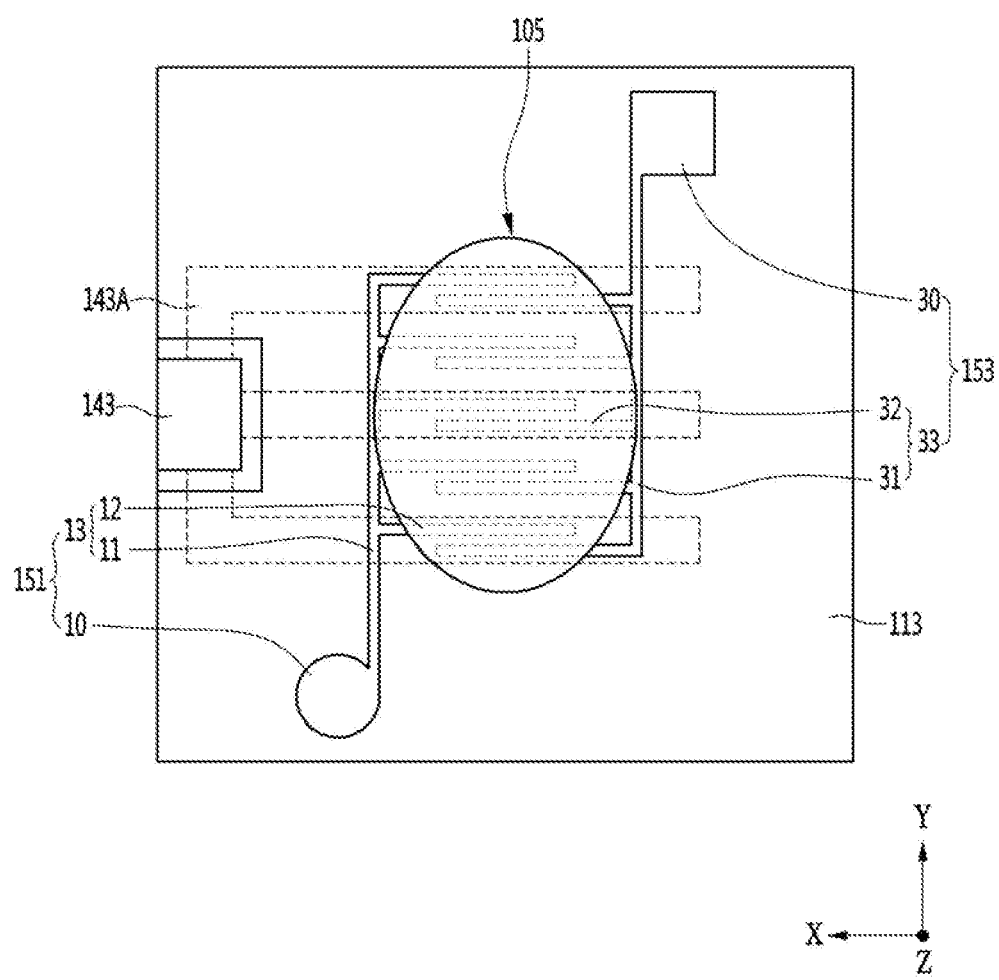

[FIG. 10]
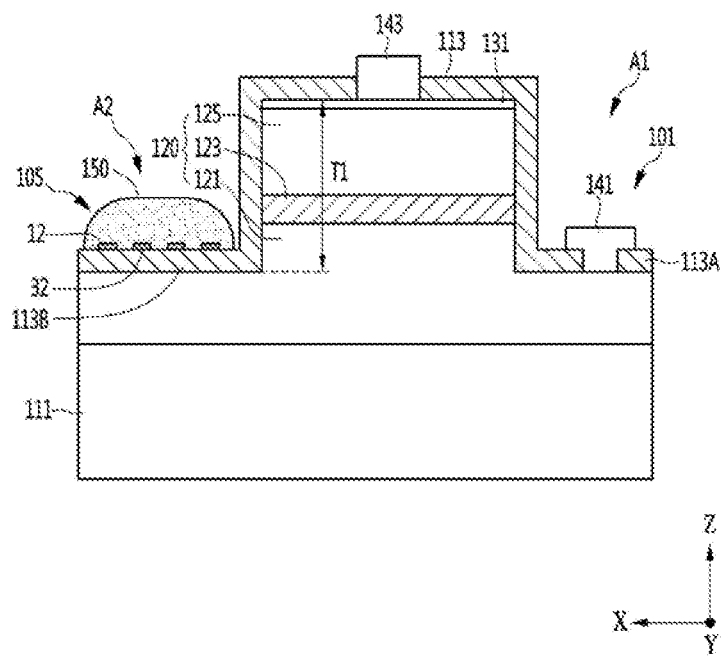
[FIG. 11]
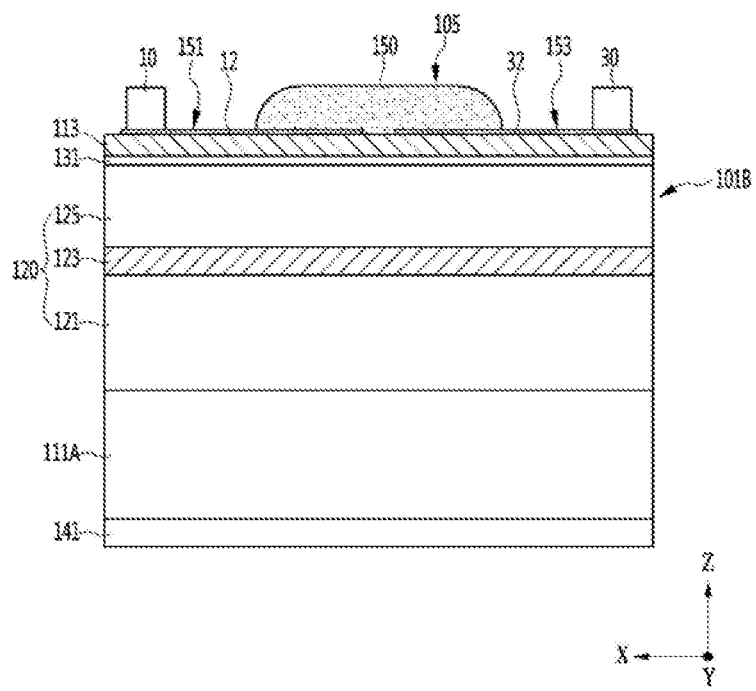

[FIG. 12]
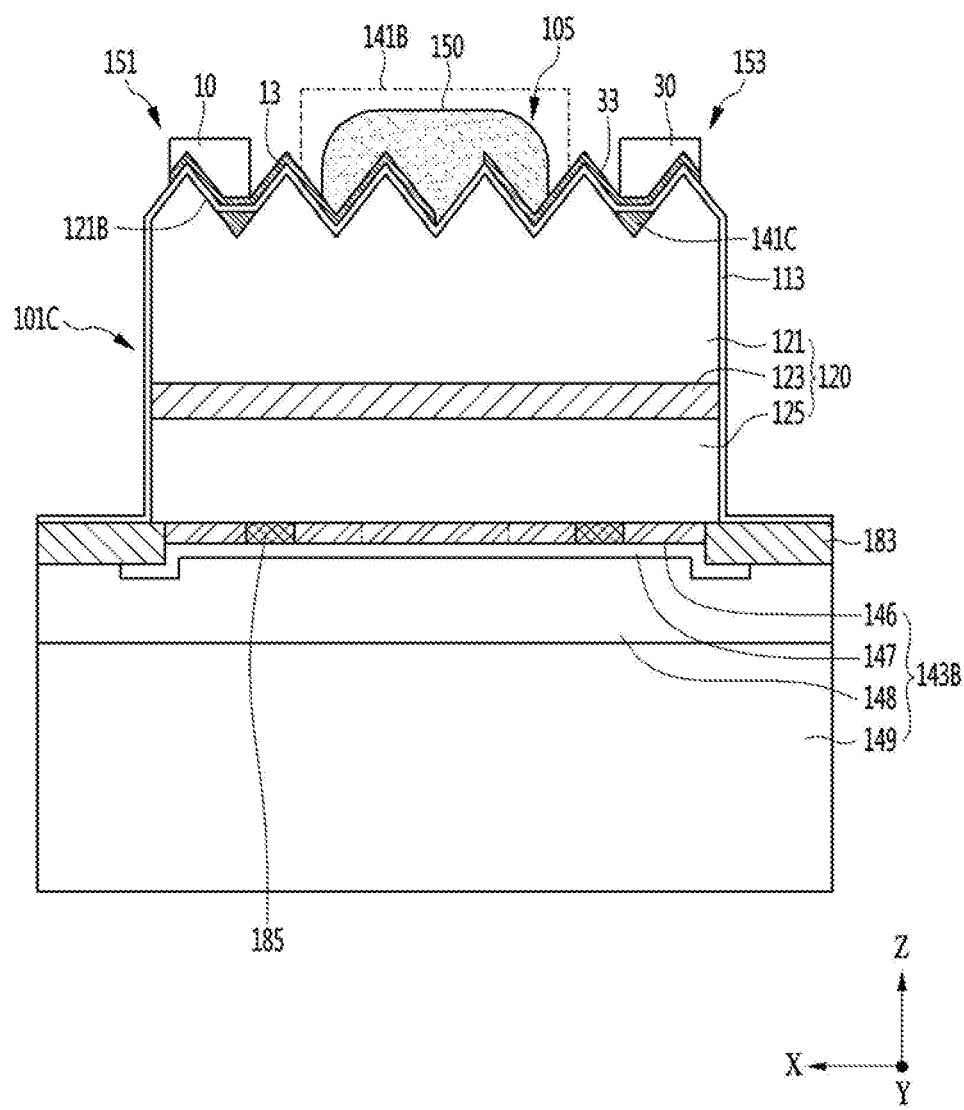

[FIG. 13]
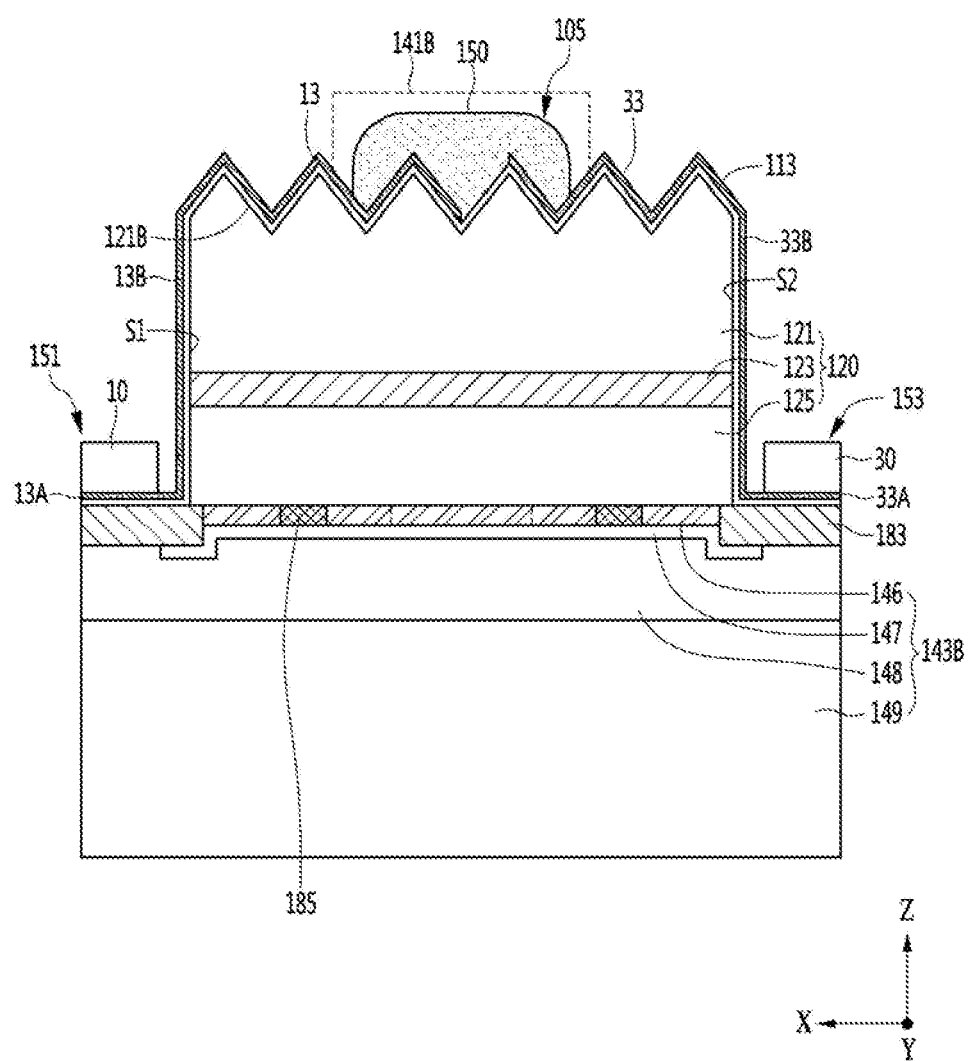

[FIG. 14]
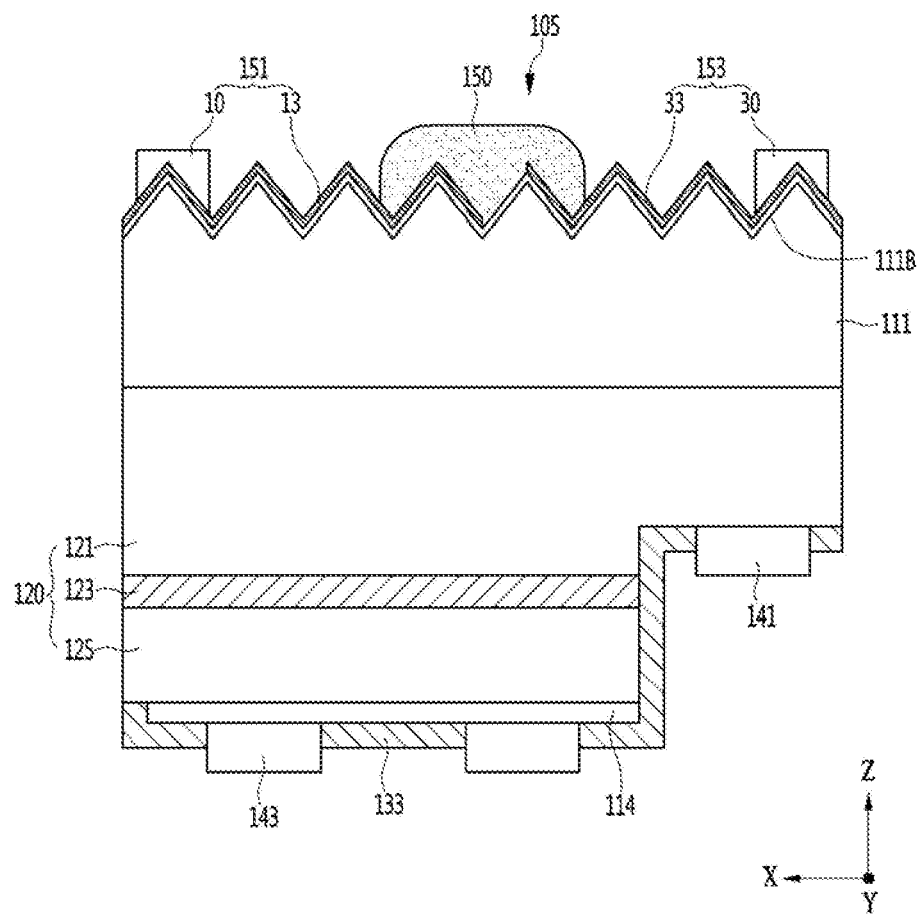

[FIG. 15]
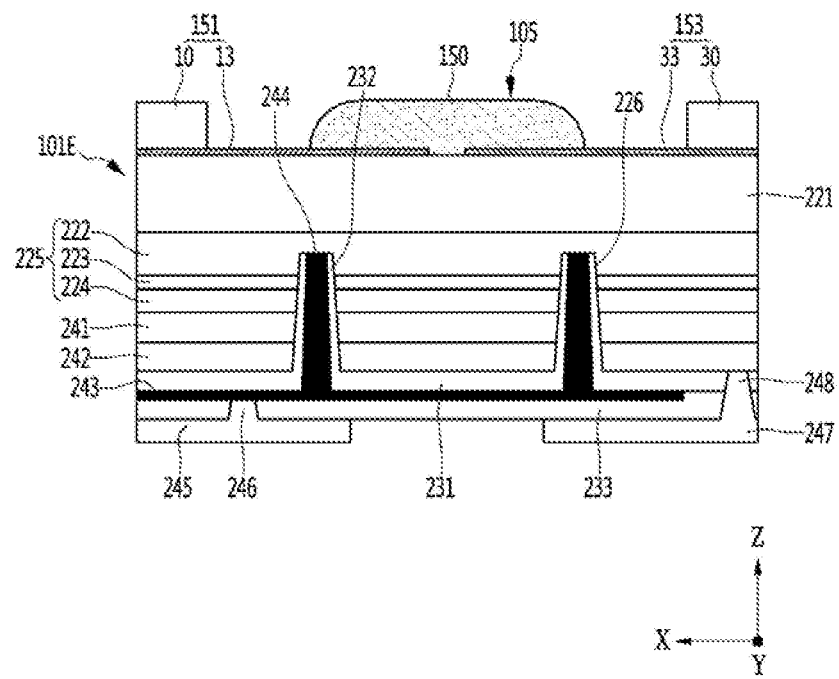
[FIG. 16]
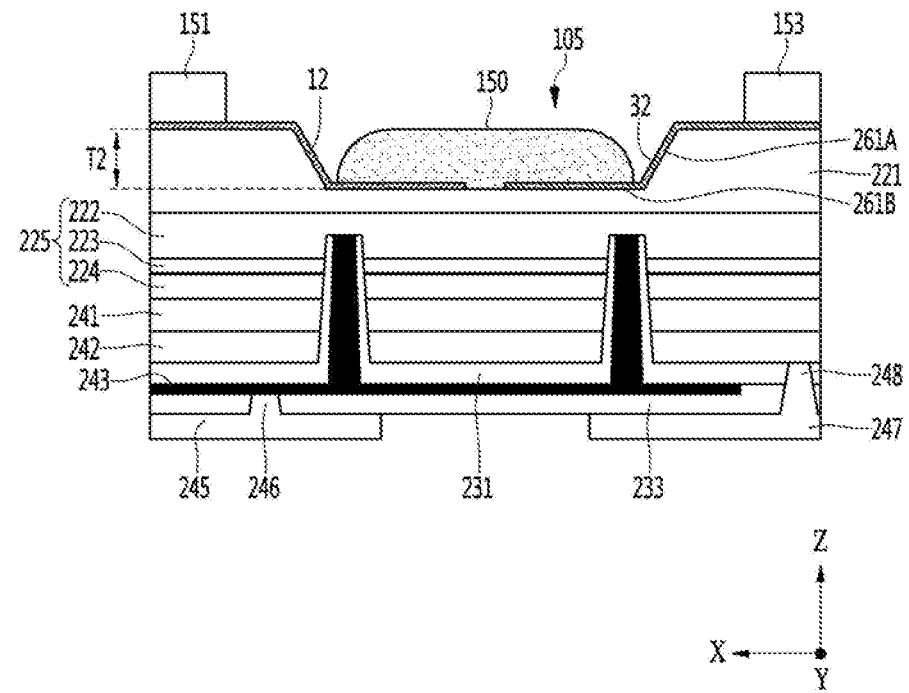

[FIG. 17]
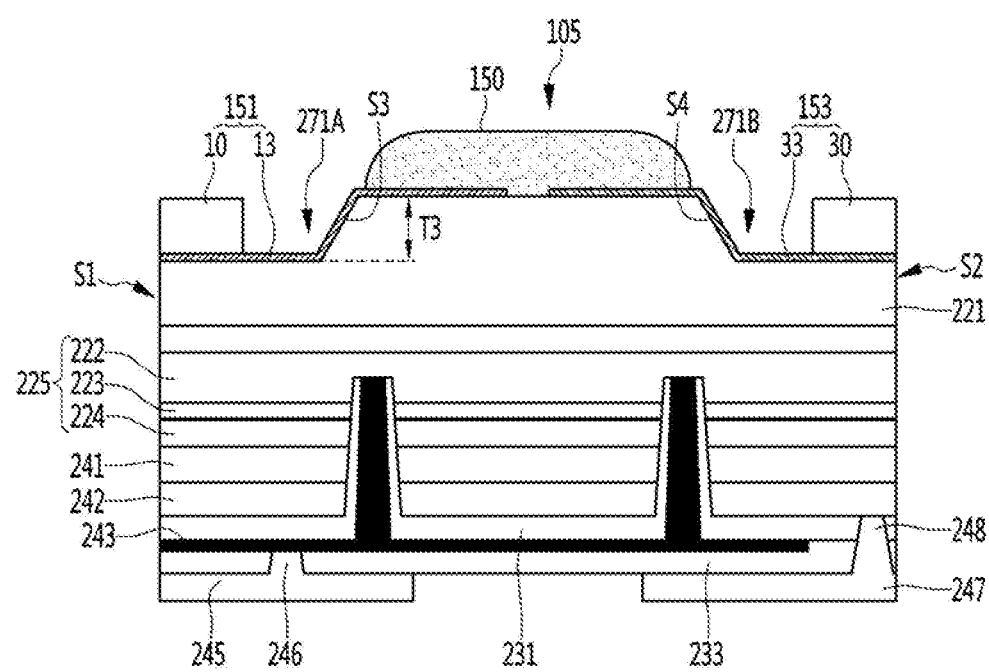

[FIG. 27]
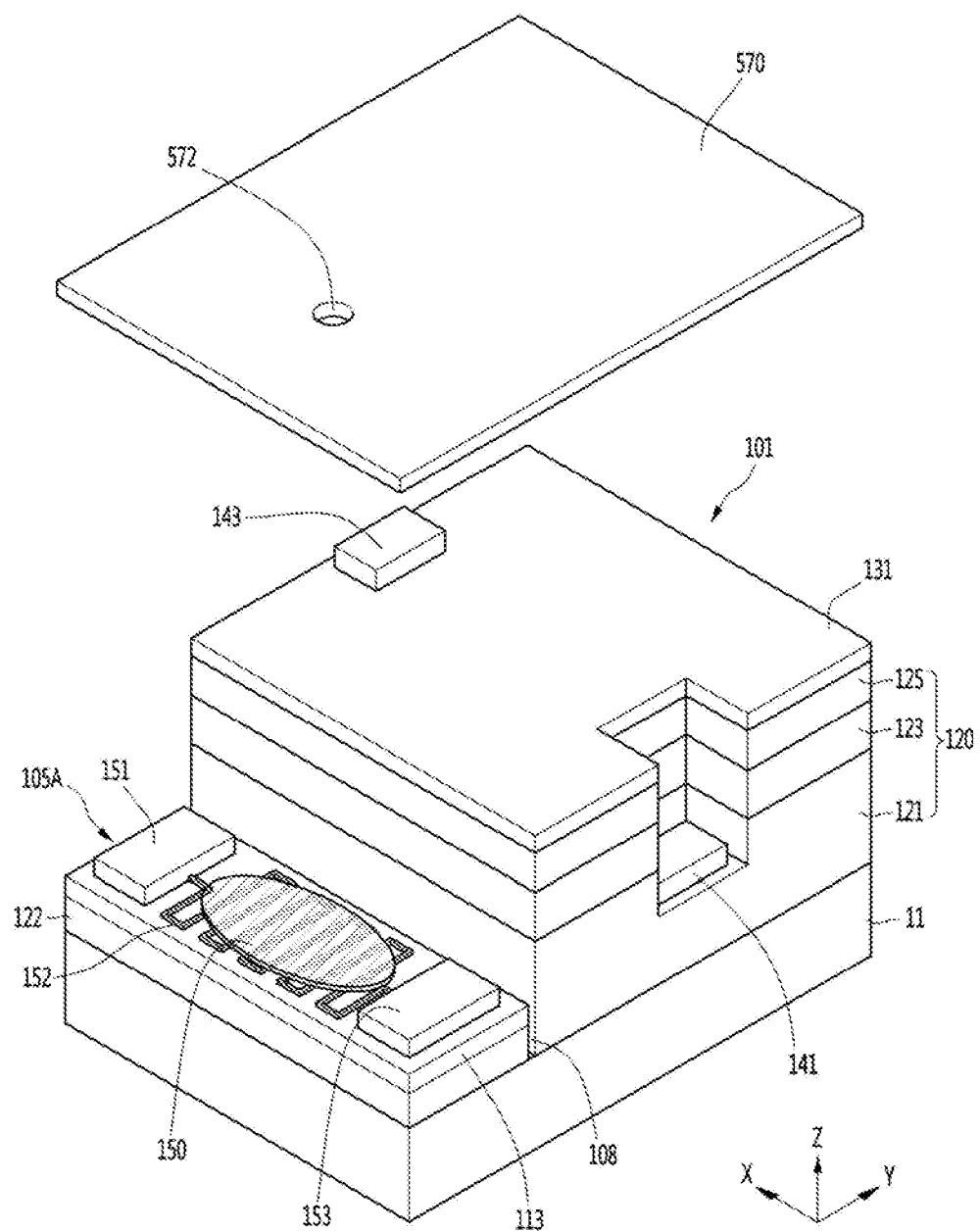

[FIG. 28]
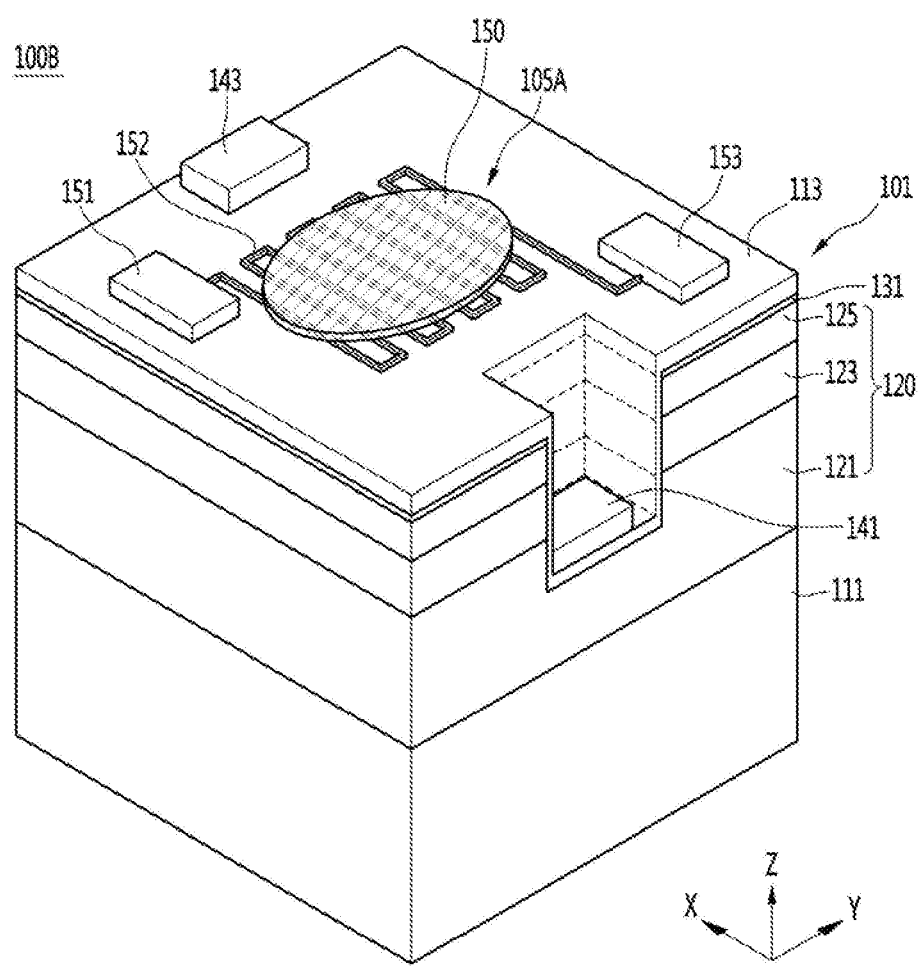

[FIG. 29]
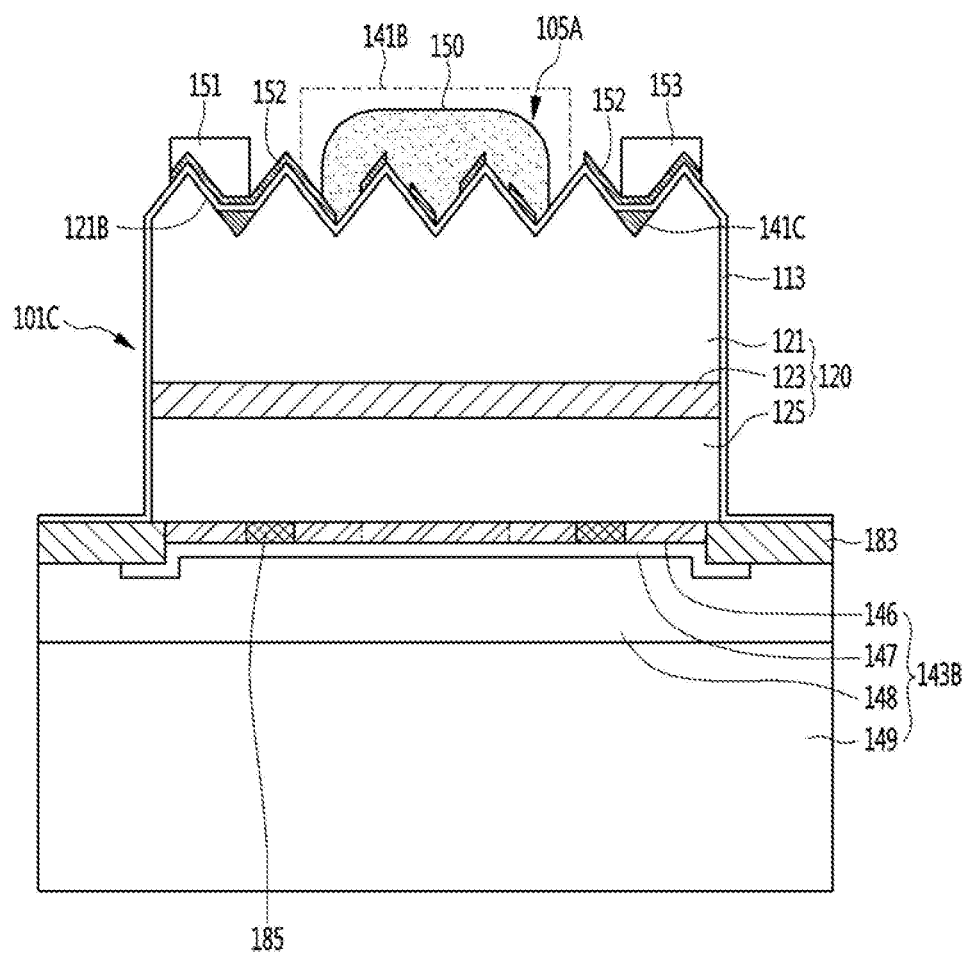

[FIG. 30]
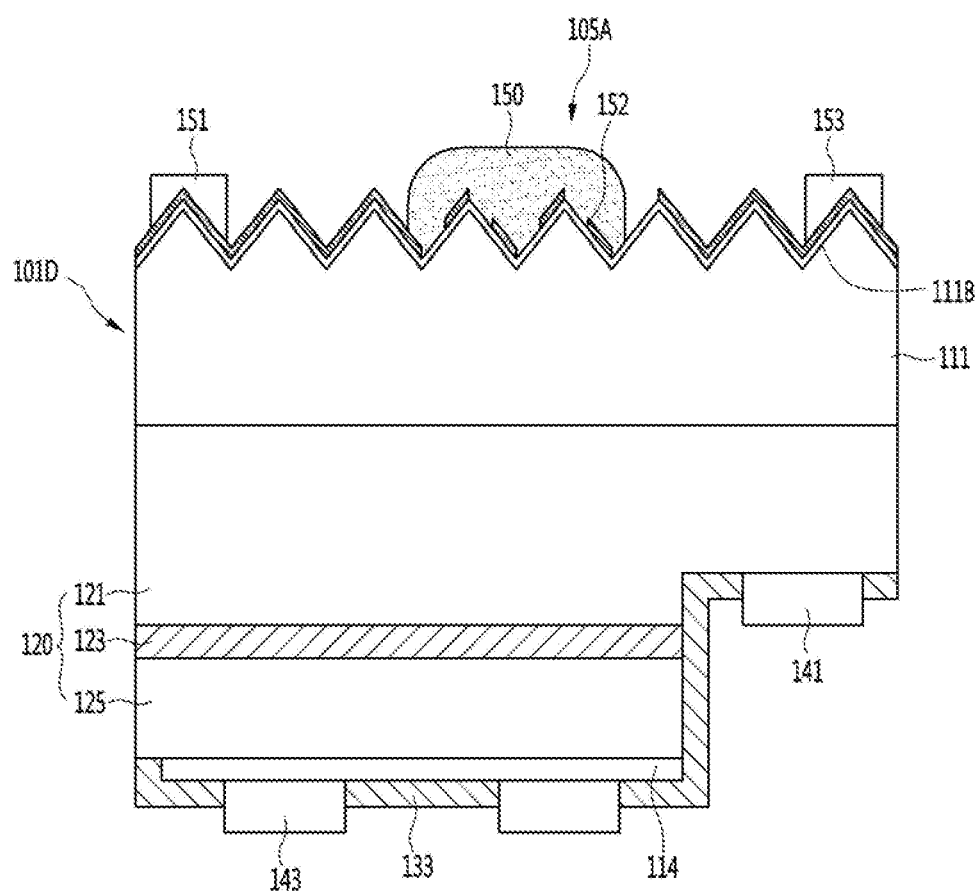

[FIG. 31]
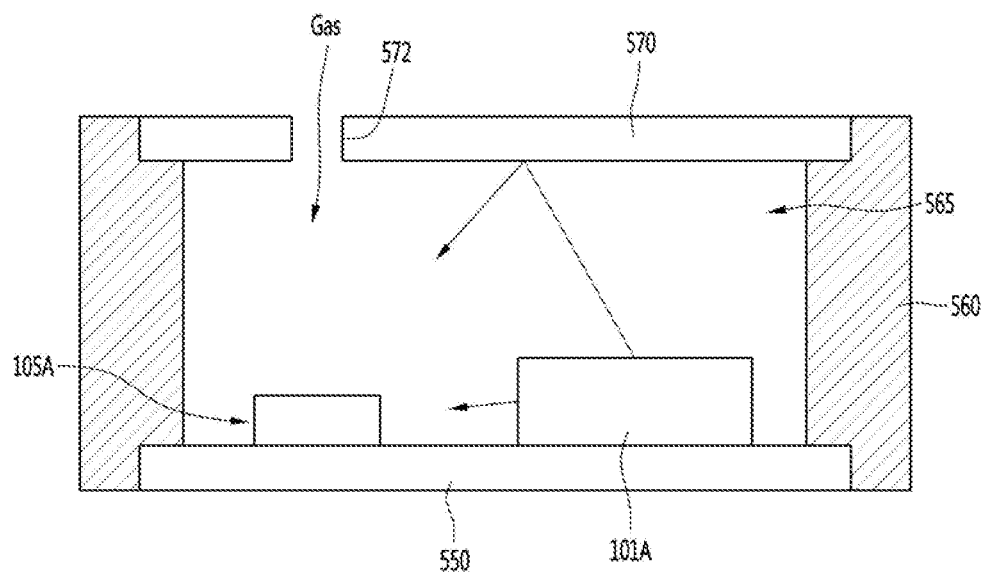
[FIG. 32]
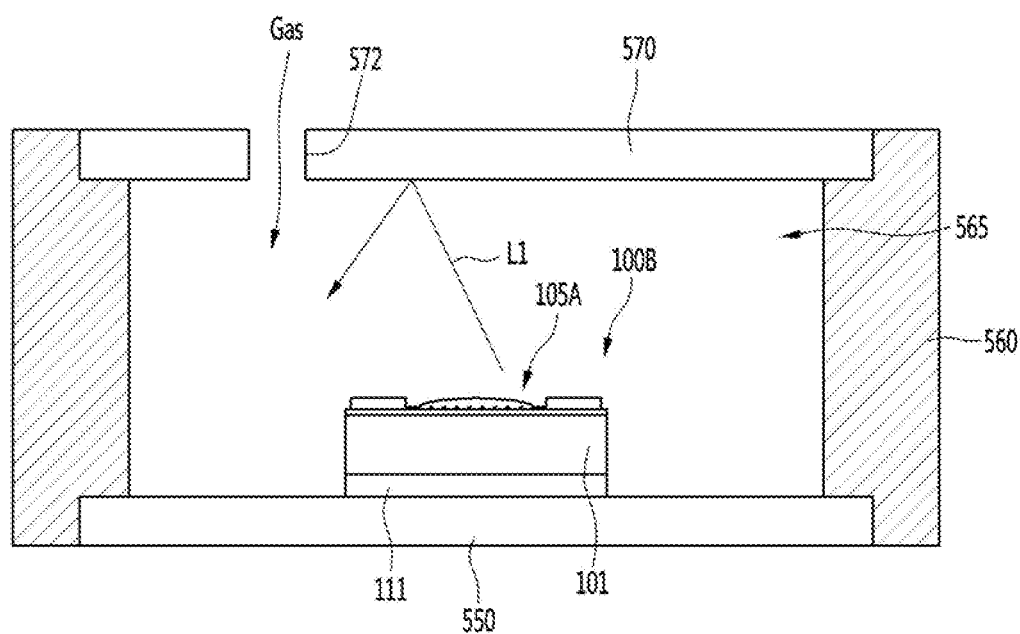

[FIG. 34]
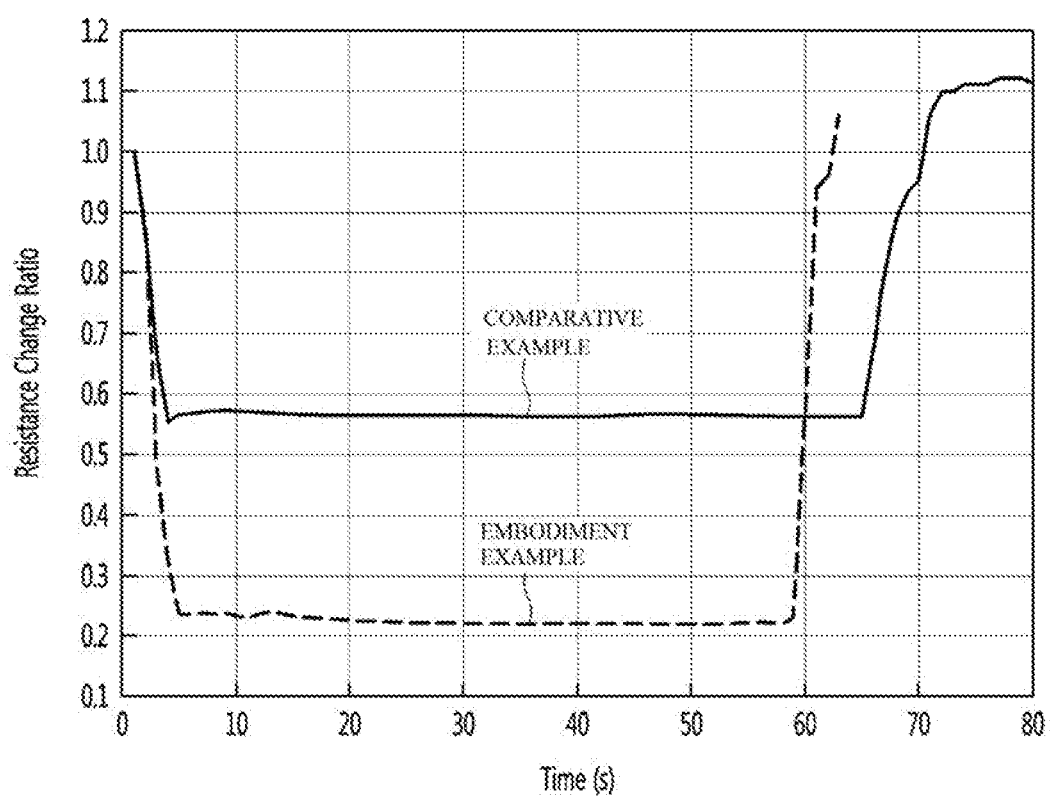

[FIG. 35]
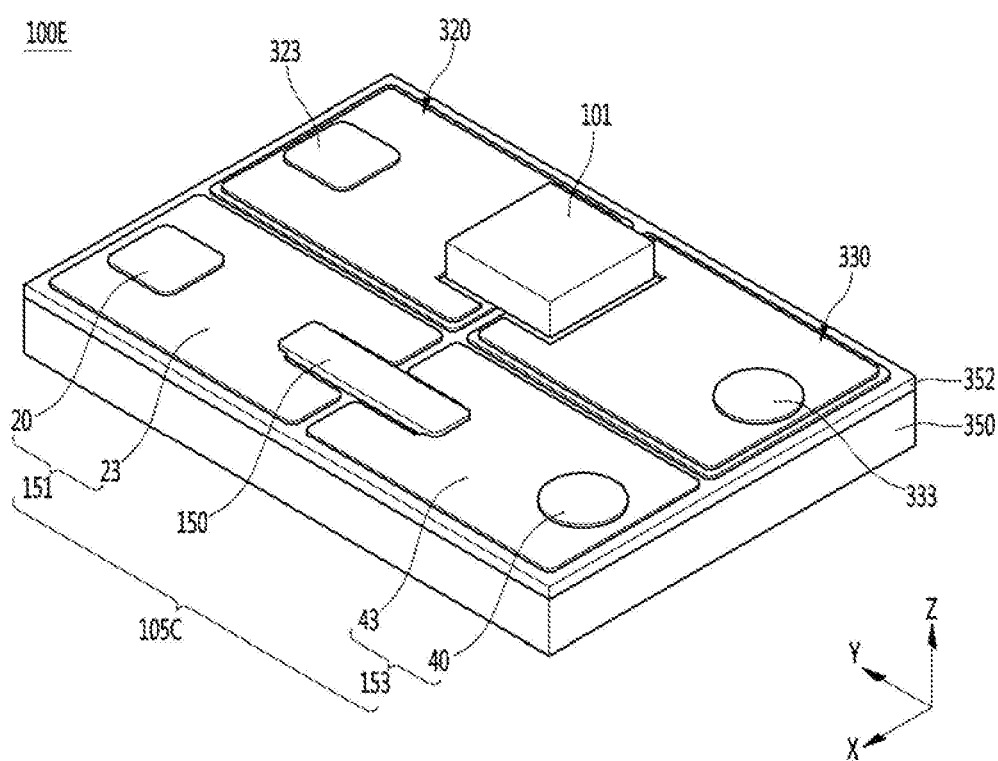

[FIG. 36]
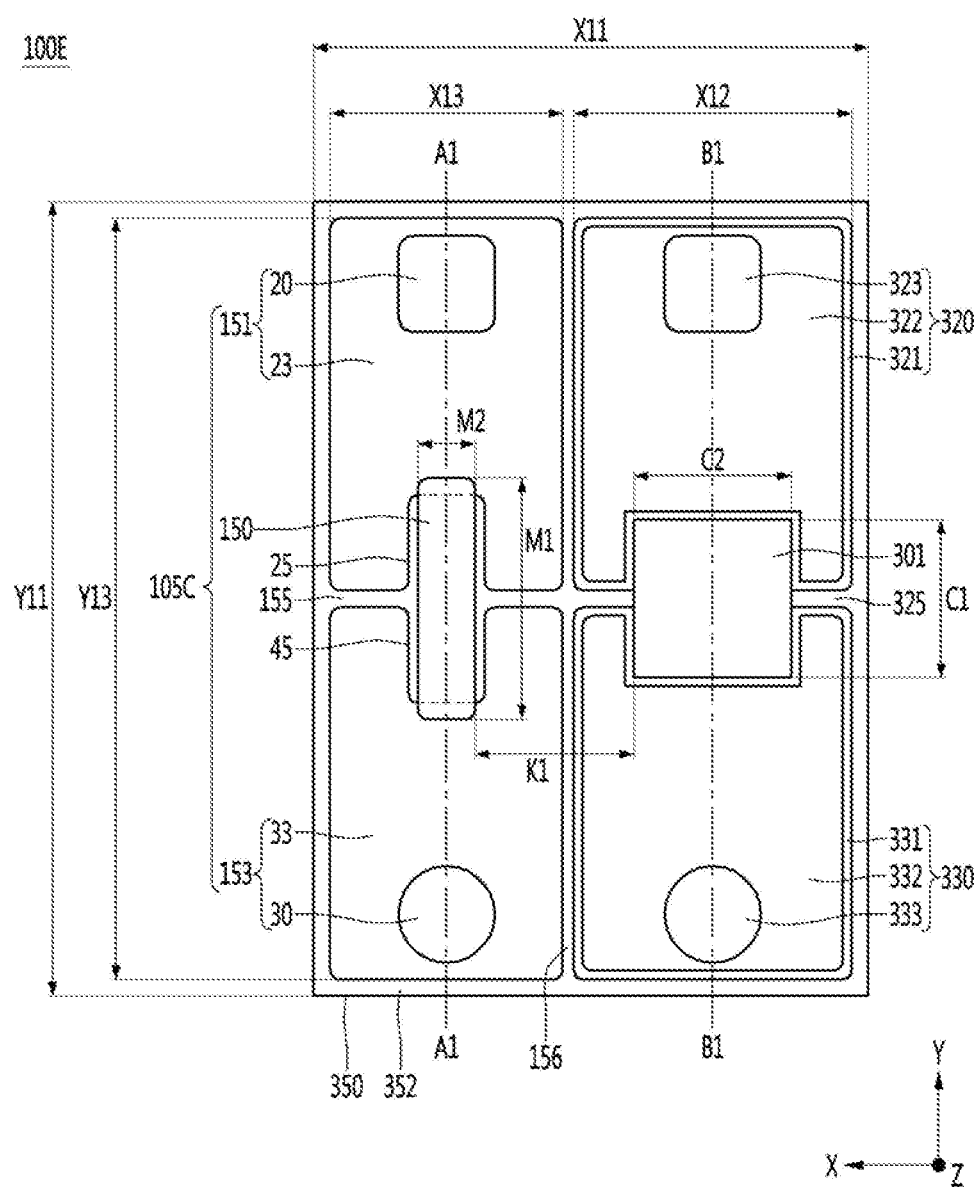

【FIG. 37】
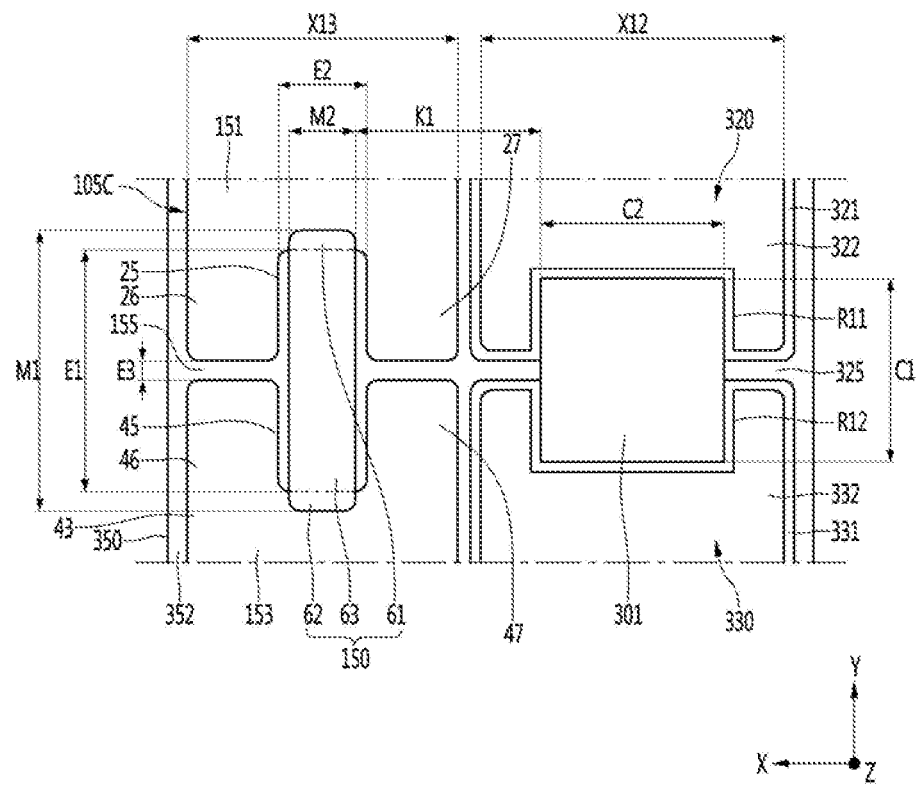
【FIG. 38】

[FIG. 39]
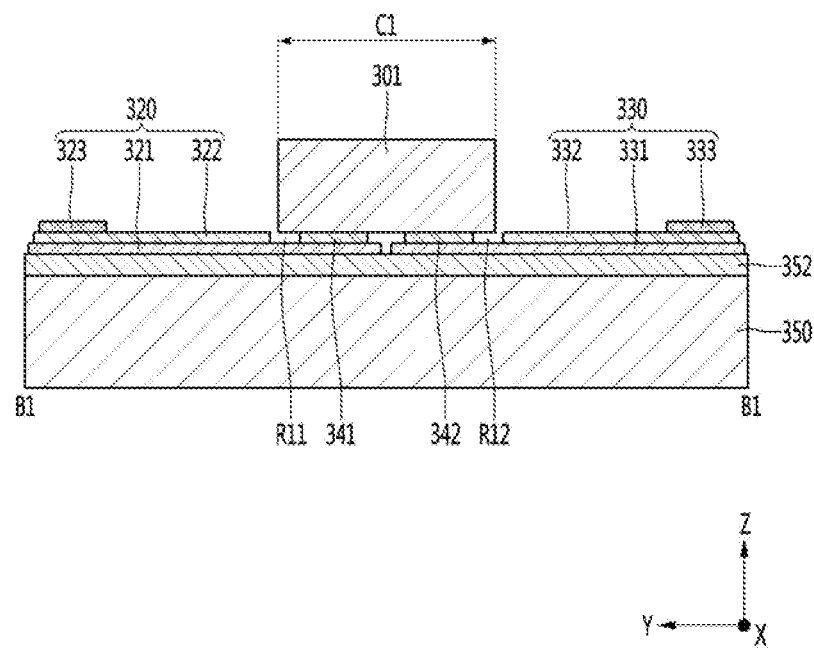
[FIG. 40]
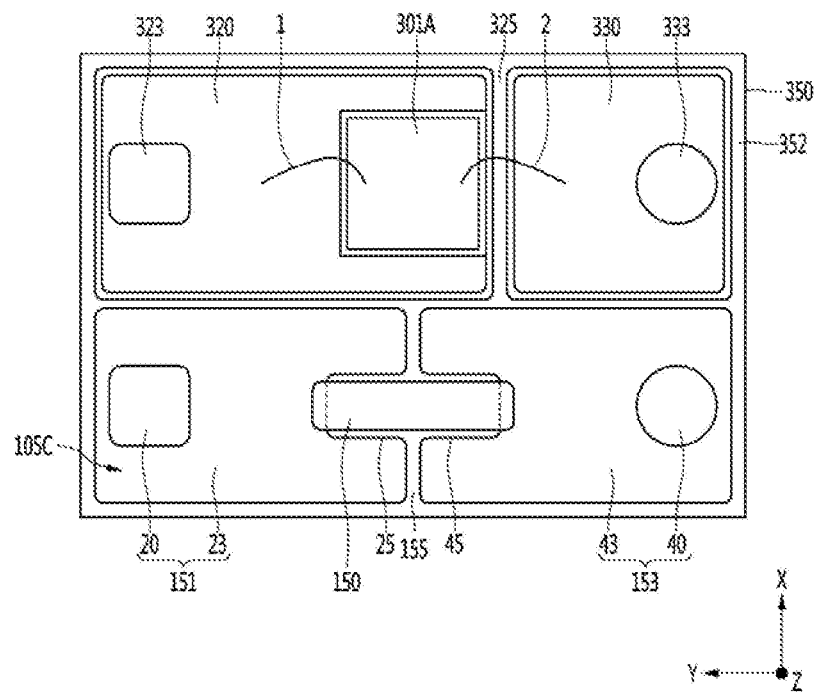

【FIG. 41】
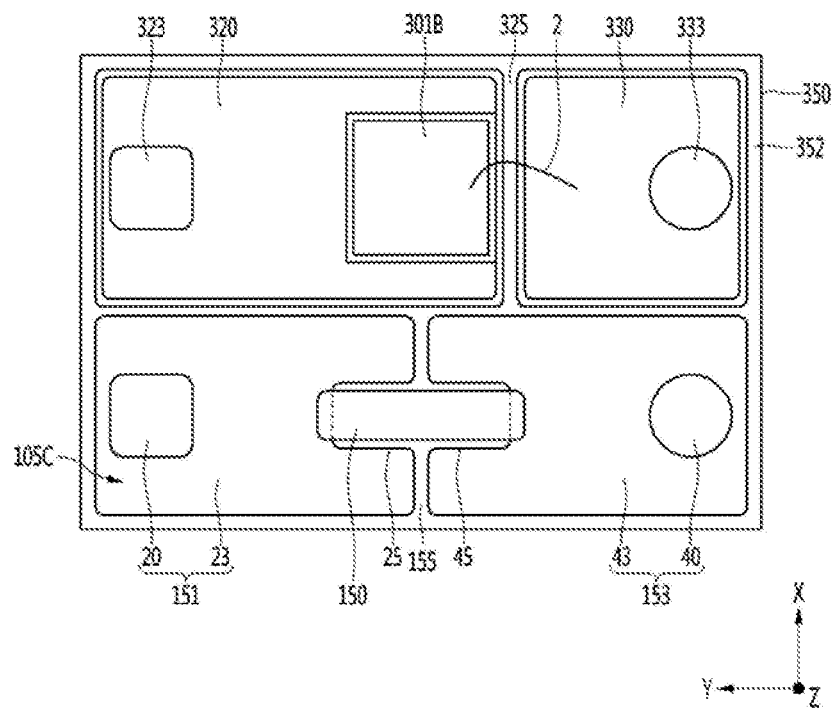
【FIG. 42】
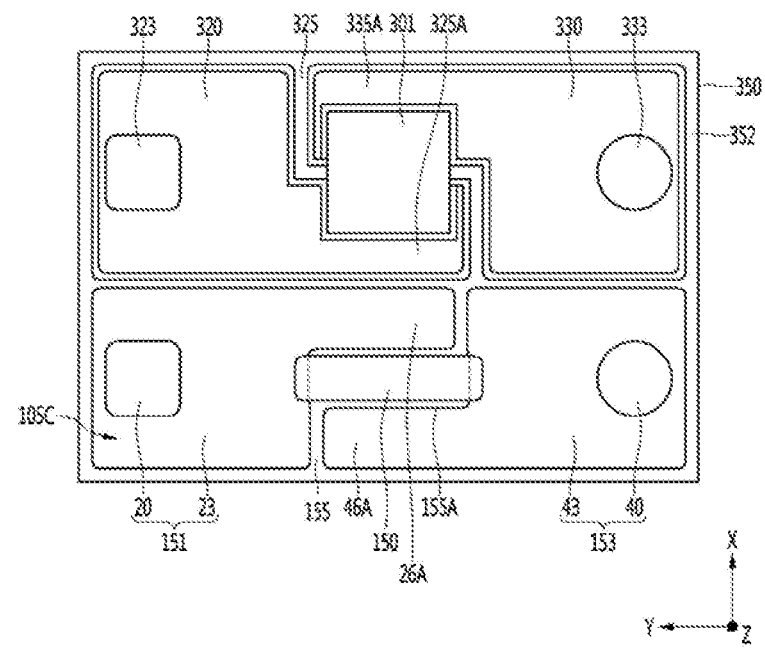

[FIG. 43]
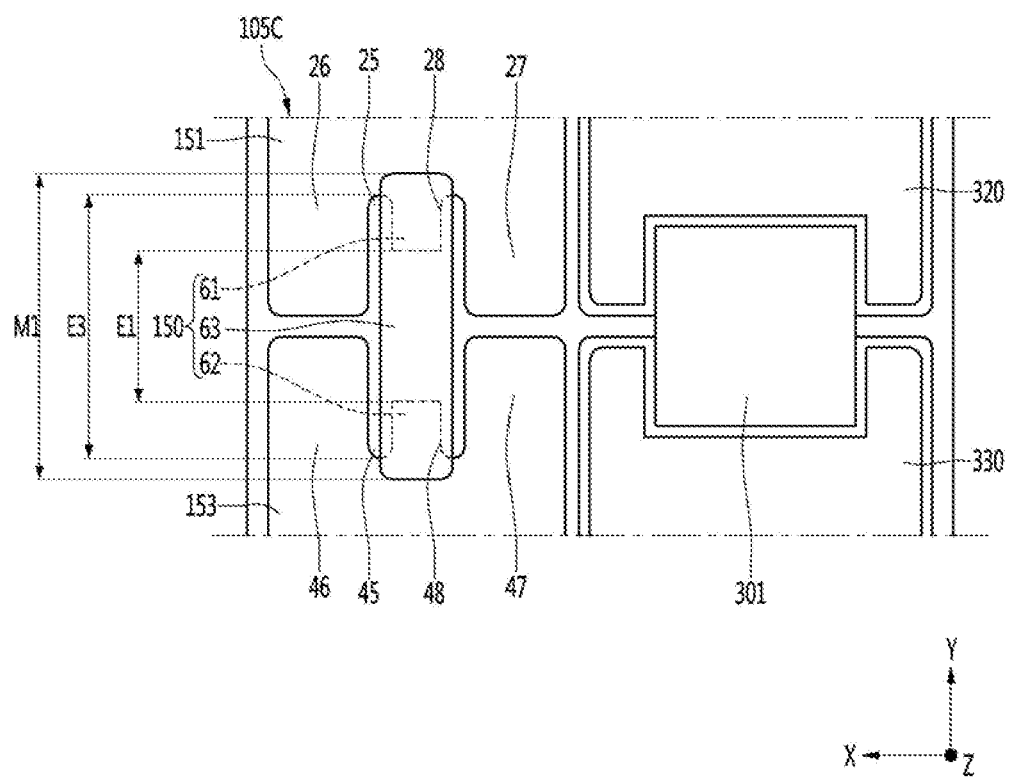
[FIG. 44]
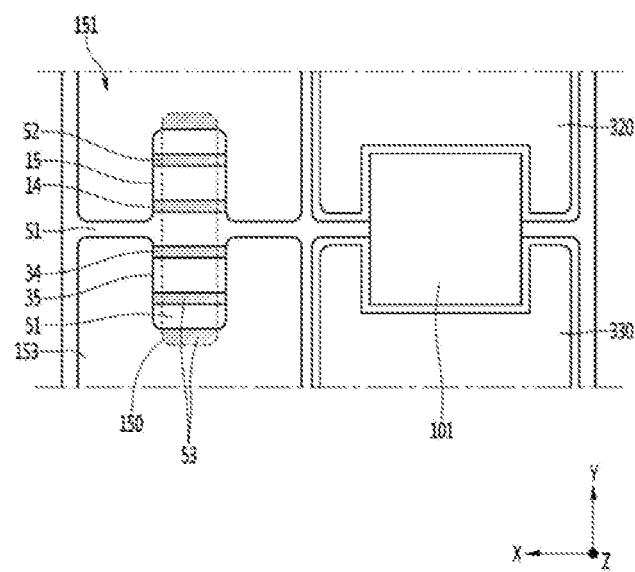

[FIG. 45]
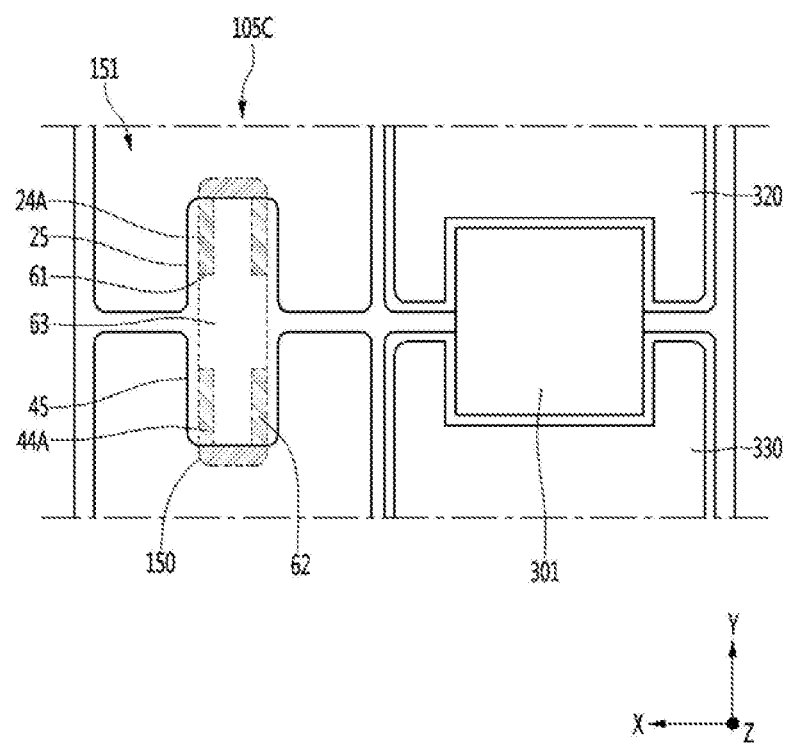

[FIG. 46]
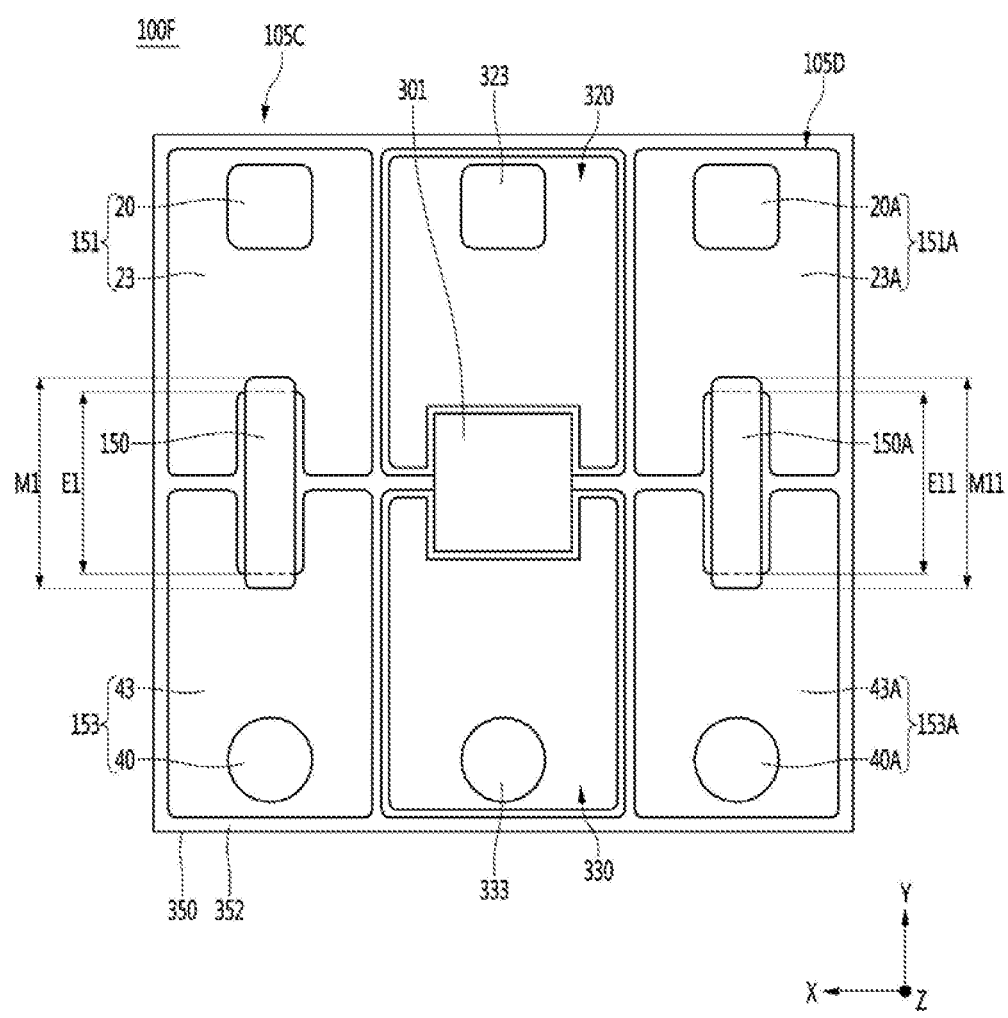

[FIG. 47]
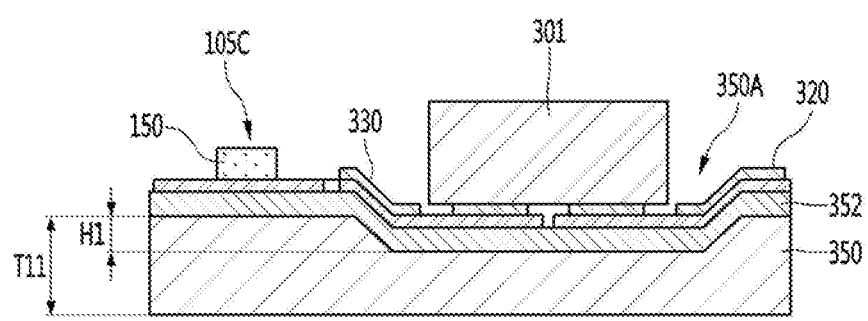
[FIG. 48]
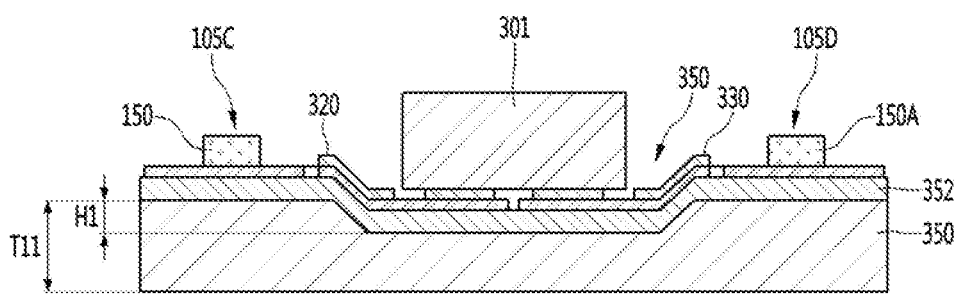

[FIG. 49]
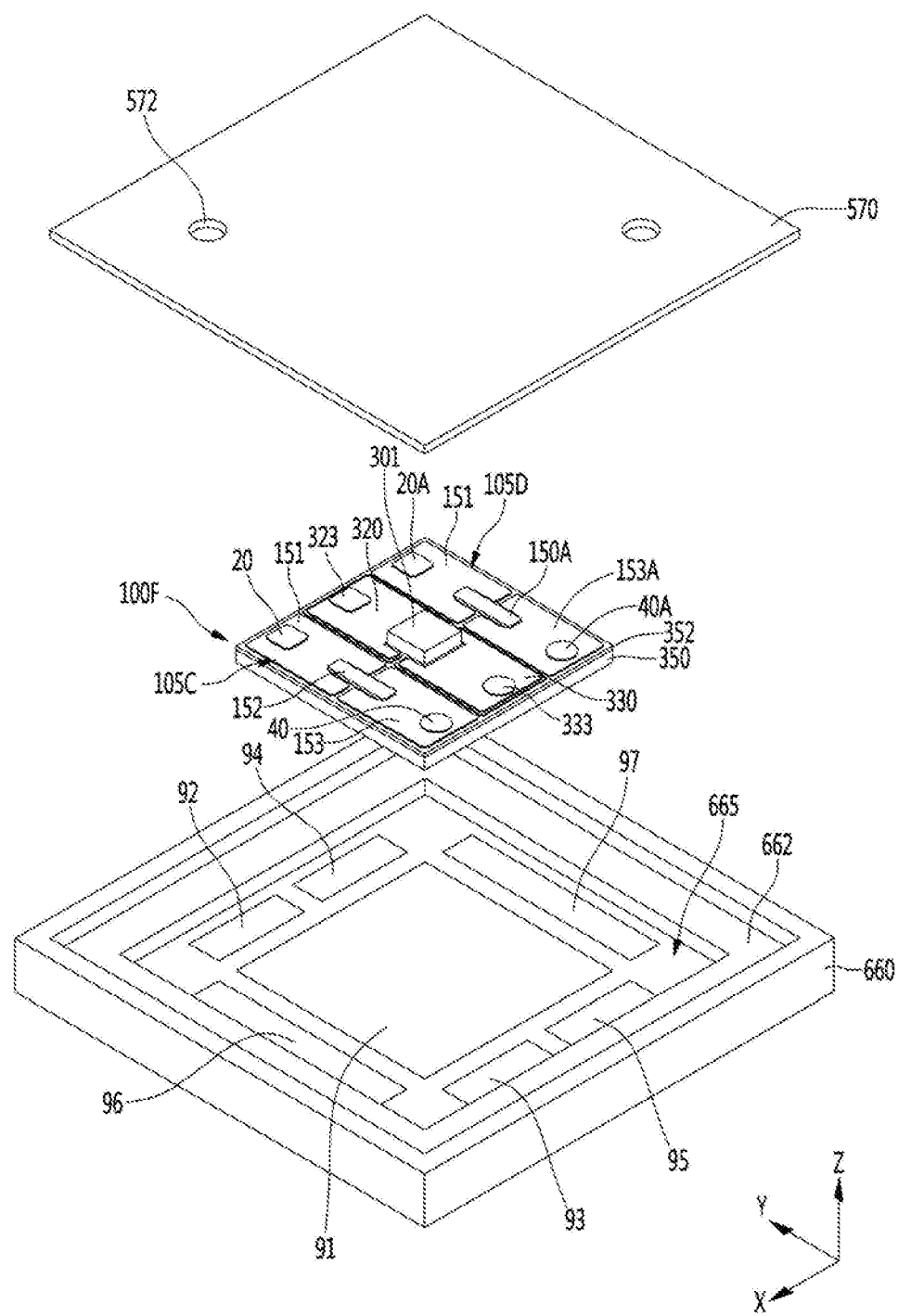

【FIG. 50】
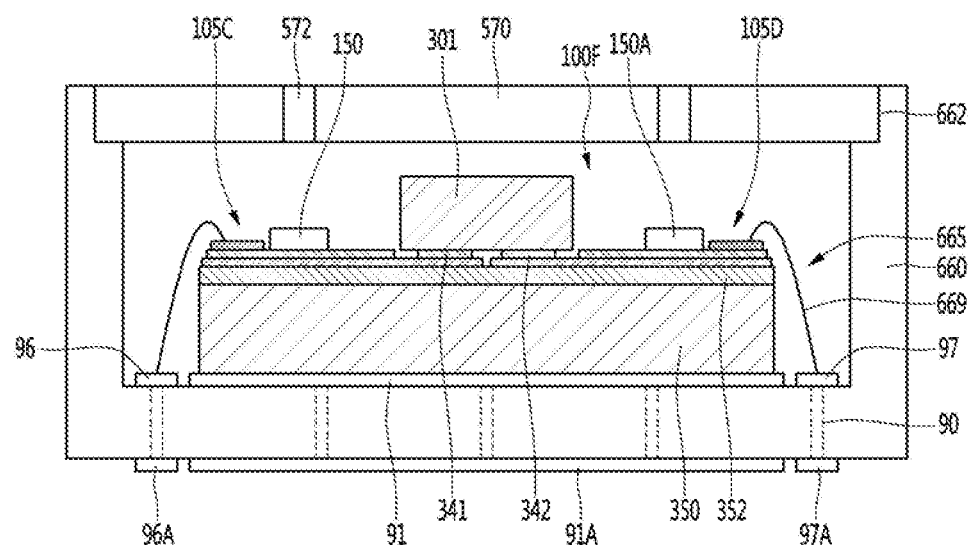
【FIG. 51】
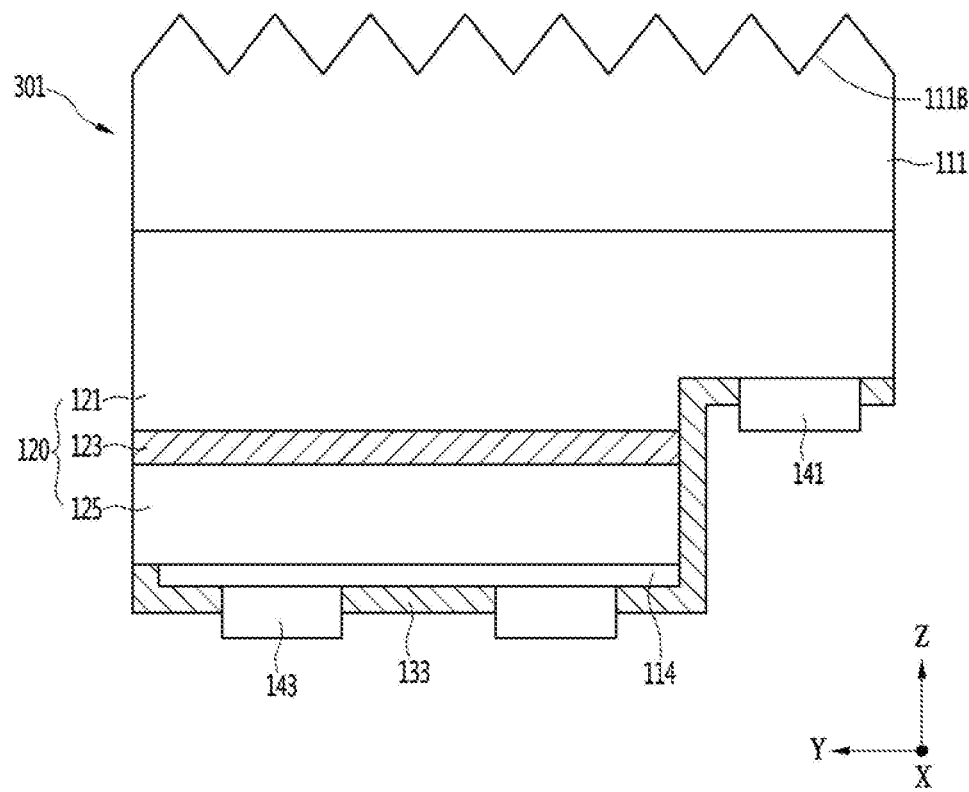

【FIG. 52】
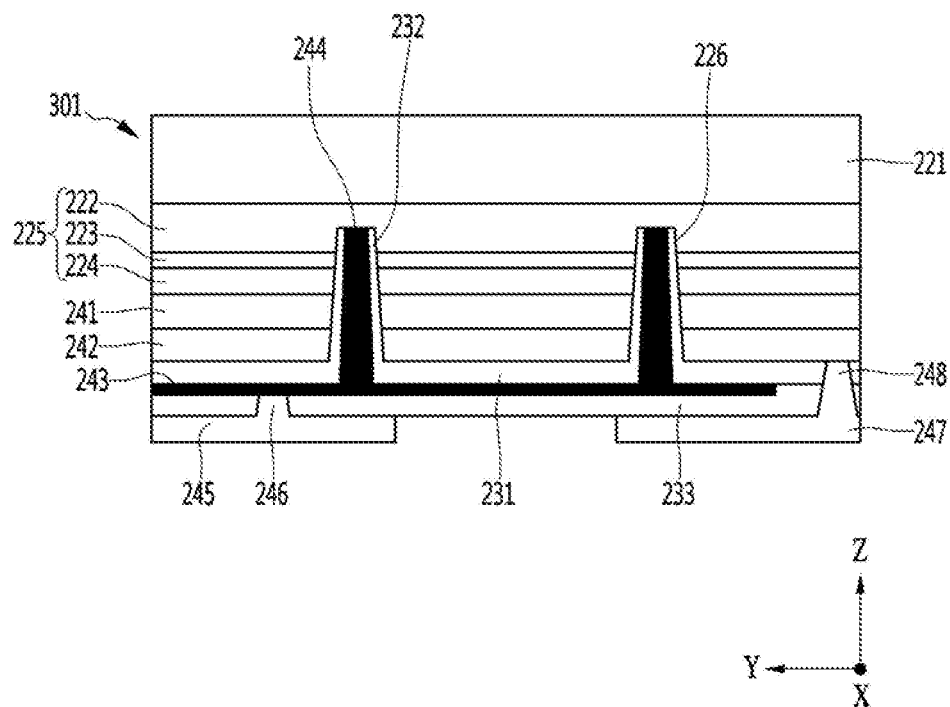
【FIG. 53】
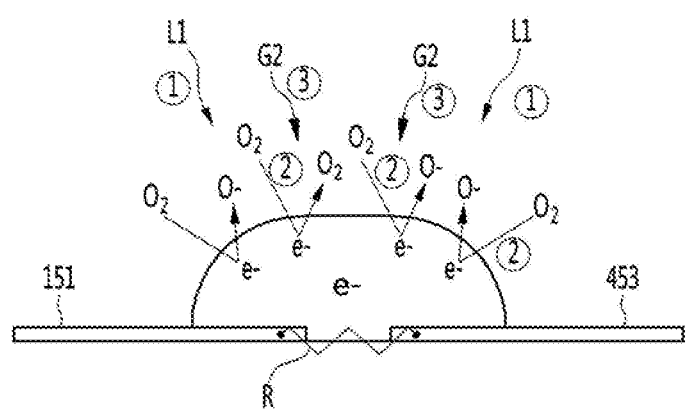

[FIG. 54]
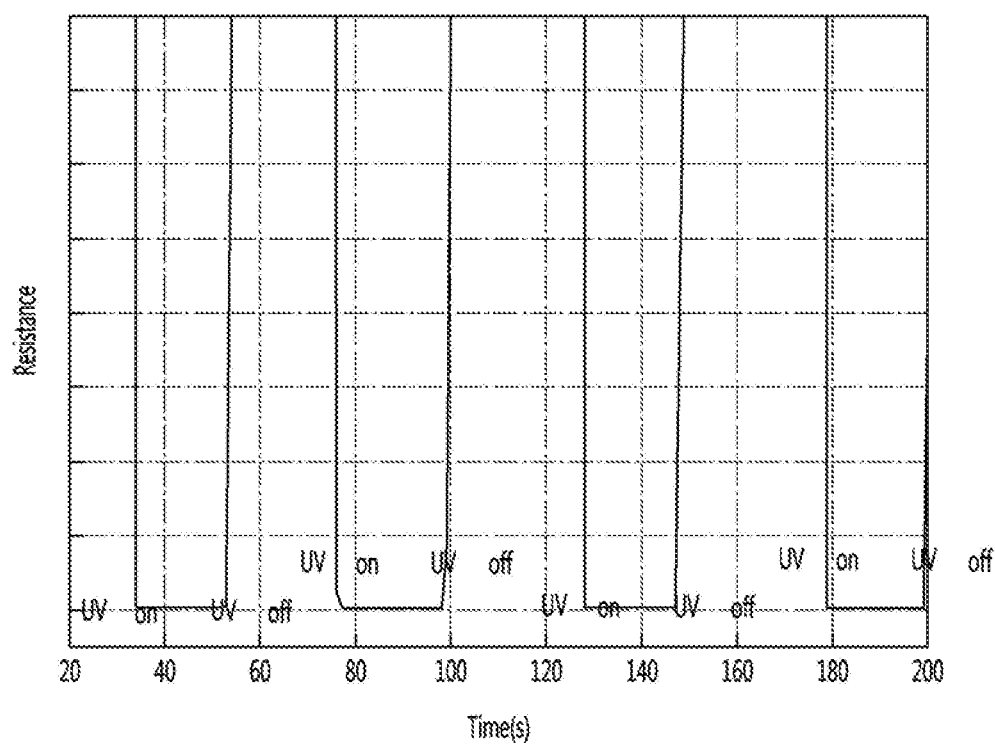

SEMICONDUCTOR ELEMENT AND SENSING DEVICE HAVING A LIGHT EMITTING UNIT AND A SENSOR UNIT

CROSS REFERENCE TO RELATED APPLICATIONS

This application is the National Phase of PCT International Application No. PCT/KR2017/014100, filed on Dec. 4, 2017, which claims priority under 35 U.S.C. 119(a) to Patent Application No. 10-2016-0164316, filed in the Republic of Korea on Dec. 5, 2016, Patent Application No. 10-2016-01.64313, filed in the Republic of Korea on Dec. 5, 2016, and to Patent Application No. 10-2016-0171887, filed in the Republic of Korea on Dec. 15, 2016, all of which are hereby expressly incorporated by reference into the present application.

TECHNICAL FIELD

Embodiment relates to a semiconductor device.

Embodiment relates to a semiconductor device having a light emitting unit and a sensor unit.

Embodiment relates to a semiconductor device for a gas sensing.

Embodiment relates to a sensing device having a sensor for a gas sensing.

Embodiment relates to a semiconductor device having a light emitting unit and a sensor unit for a gas sensing.

Embodiment relates to a semiconductor type device and a sensing device for detecting a gas.

Embodiment relates to a gas sensing apparatus and a sensing method.

BACKGROUND ART

There are many kinds of gases in our living environment. Problems such as gas accidents in general homes, businesses, construction sites, explosion accidents in petroleum Kombinat, mines, chemical plants, and pollution are continuing. Human sensory organs can't quantitatively determine a concentration of a hazardous gas or can hardly distinguish the type of the gas. In order to cope with this problem, a gas sensor using physical properties or chemical properties of a material has been developed and used for leakage detection, concentration measurement and alarm for gas.

Such gas sensors have been studied for a long time, and there are currently many types of commercially available gas sensors. When a gas component is adsorbed on a surface of a semiconductor or reacted with an adsorbing gas such as oxygen etc., which has been adsorbed or pre-adsorbed, a gas sensor using a semiconductor causes electron exchange between the adsorbing molecules and the surface of the semiconductor, which changes a conductivity of the semiconductor and a surface potential, and the like, which are the principle for detecting such changes.

Semiconductor gas sensors are simpler in structure, easier to process, smaller in size and lower in power consumption than optical gas sensors or electrochemical gas sensors through measurement of conductivity by a spectrum or an ion mobility of the measurement atmosphere.

DISCLOSURE

Technical Problem

An embodiment of the invention provides a semiconductor device for gas sensing and a method of manufacturing the same.

An embodiment of the invention provides a semiconductor device having a sensor unit that detects a gas in response to light emitted from a light emitting unit, and a method of manufacturing the same.

An embodiment of the invention provides a semiconductor device in which a light emitting unit for irradiating ultraviolet light and a sensor unit for detecting gas are disposed in an overlapped region.

An embodiment of the invention provides a semiconductor device in which a sensor unit is disposed on at least one of a semiconductor layer and a substrate of a light emitting unit.

An embodiment of the invention provides a semiconductor device in which a sensor unit is disposed in a region vertically overlapped with a light emitting unit.

Embodiments of the invention provide a semiconductor device for sensing a change in resistance by a sensing material and a method of manufacturing the same.

An embodiment of the invention provides a semiconductor device for detecting a change in resistance in an electrode portion continuously connected between two pad portions and a sensing material disposed on the electrode portion, and a manufacturing method thereof.

An embodiment of the invention provides a semiconductor device having a sensing material that detects a gas in response to light emitted from a light emitting unit, and a method of manufacturing the same.

An embodiment of the invention provides a semiconductor device having a light emitting unit for irradiating ultraviolet light and a sensor unit for detecting gas.

An embodiment of the invention provides a semiconductor device in which a sensor unit is disposed on at least one of a semiconductor layer and a substrate of a light emitting unit.

An embodiment of the invention provides a semiconductor device in which a sensor unit is disposed in a region adjacent to a light emitting unit.

An embodiment of the invention provides a semiconductor device having a light emitting unit for irradiating light and a sensor unit for sensing gas onto different regions of a substrate.

An embodiment of the invention provides a semiconductor device in which one or a plurality of sensor units are disposed to a region corresponding to at least one side of a sides of a light emitting unit and a light emitting unit on a substrate.

An embodiment of the invention provides a sensing device having a semiconductor device for a gas sensor.

Technical Solution

A semiconductor device according to an embodiment of the invention comprises: a light emitting unit including a first conductivity type semiconductor layer, a second conductivity type semiconductor layer, and a light emitting structure layer having an active layer between the first conductivity type semiconductor layer and the second conductivity type semiconductor layer; and a sensor unit disposed on the light emitting unit, wherein the sensor unit includes: a sensing material of which resistance is changed by light emitted from the light emitting unit; a first sensor electrode including a first pad portion and a first extension part extending from the first pad portion and contacting to the sensing material; and a second sensor electrode including a second pad portion and a second extension part extending from the second pad portion toward the first extension part and contacting to the sensing material, the first extension part is spaced apart from the second extension part, the sensing material is disposed on the first extension part and the second extension part, and the sensing material includes a first region overlapped with at least one of the first and second extension parts in a vertical direction and a second region not overlapped with the first and second extension parts in the vertical direction.

A sensing apparatus according to an embodiment of the invention comprises: a circuit board; a package body disposed on the circuit board and including a cavity, a sensor unit disposed in the cavity, a light emitting unit disposed between the sensor unit and the substrate; and a reflective plate having an opening part on the sensor unit, wherein the light emitting unit includes a first conductivity type semiconductor layer, a second conductivity type semiconductor layer, and a second conductivity type semiconductor layer between the first conductivity type semiconductor layer and the second conductivity type semiconductor layer, wherein the sensor unit comprises: a sensing material of which resistance is changed by light emitted from the light emitting unit; a first sensor electrode including a first pad portion and a first extension part extending from the first pad portion and contacting to the sensing material; and a second sensor electrode including a second pad portion and a second extension part extending from the second pad portion toward the first extension part and contacting to the sensing material, the first extension part is spaced apart from the second extension part, the sensing material is disposed on the first extension part and the second extension part, and the sensing material may include a first region overlapped with at least one of the first and second extension parts in a vertical direction and a second region not overlapped with the first and second extension parts in the vertical direction.

A semiconductor device according to an embodiment of the invention comprises: a substrate; a light emitting unit disposed on the substrate; and a sensor unit disposed on at least one of the substrate and the light emitting unit, wherein the light emitting unit includes: a first conductivity type semiconductor layer; a second conductivity type semiconductor layer; an active layer disposed between the first conductivity type semiconductor layer and the second conductivity type semiconductor layer; a first electrode electrically connected to the first conductivity type semiconductor layer; and a second electrode electrically connected to the second conductivity type semiconductor layer, the sensor unit includes a first pad portion, a second pad portion spaced apart from the first pad portion, an electrode portion extending from the first pad portion and connected to the second pad portion, and a sensing material disposed on the electrode portion, the sensing material includes at least one first region overlapped with the electrode portion in a vertical direction and at least one second region not overlapped with the electrode portion in the vertical direction, a surface of the sensing material corresponds to at least one of an upper surface and a side surface of the light emitting unit, and a resistance of the sensing material may be changed by light emitted from the light emitting unit.

A sensing apparatus according to an embodiment of the invention comprises: a circuit board; a semiconductor device including a substrate on the circuit board, a light emitting unit on the substrate, and a sensor unit on the light emitting unit; a package body disposed around the semiconductor device; and a reflective plate on the semiconductor device, a substrate, a light emitting unit disposed on the substrate; and a sensor unit disposed on at least one of the substrate and the light emitting unit, wherein the light emitting unit includes a first conductivity type semiconductor layer, a second conductivity type semiconductor layer, a first conductivity type semiconductor layer, an active layer disposed between the layers; a first electrode electrically connected to the first conductivity type semiconductor layer; and a second electrode electrically connected to the second conductivity type semiconductor layer, wherein the sensor unit includes a first pad portion, a second pad portion spaced apart from the first pad portion, and a second pad portion extending from the first pad portion, and a sensing material disposed on the electrode portion, wherein a sensing material includes at least one first region overlapping the electrode portion in a vertical direction, and at least one first region overlapping the electrode portion in a direction perpendicular to the electrode portion, wherein a surface of the sensing material corresponds to at least one of the upper surface and the side surface of the light emitting unit and a resistance of the sensing material may be changed by the light emitted from the light emitting unit.

A semiconductor device according to an embodiment of the invention comprises: a support member; a light emitting unit on a first region of the support member; and a first sensor unit is disposed on a second region of the support member, wherein the light emitting unit includes a light emitting structure layer having a first conductivity type semiconductor layer, a second conductivity type semiconductor layer, and an active layer between the first conductivity type semiconductor layer and the second conductivity type semiconductor layer, the first sensor unit includes at least one first sensing material activated by light emitted from the light emitting unit, a first sensor electrode including a first electrode portion contacted to the first sensing material, and a second sensor electrode including a second electrode portion contacted to the first sensing material, the first electrode portion is spaced apart from the second electrode portion, the first sensing material is disposed on the first electrode portion and the second electrode portion, and the first sensing material may include a first part overlapped with the first electrode portion in a vertical direction, a second part overlapped with the second electrode portion in the vertical direction, and a third part not overlapped with the first and second electrode portions in the vertical direction between the first and second electrode portions.

A sensing apparatus according to an embodiment of the invention comprises: a package body having a cavity; a semiconductor device disposed in the cavity; and a reflective plate having an opening part disposed on the semiconductor device, the semiconductor device comprising: a support member; a light emitting unit over a first region of the support member; and a first sensor unit disposed on a second region of the support member, wherein the light emitting unit includes a first conductivity type semiconductor layer, a second conductivity type semiconductor layer, and a second conductivity type semiconductor layer, wherein the first sensor unit includes at least one first sensing material activated by light emitted from the light emitting unit; a first sensor electrode including a first electrode portion contacting the first sensing material; and a second sensor electrode including a second electrode portion contacting the first sensing material, wherein the first electrode portion is spaced apart from the second electrode portion, and the first sensing material is separated from the first electrode portion and the second sensing portion, wherein the first sensing material may include a first part overlapping the first electrode portion in a vertical direction, a second part overlapping the second electrode portion in a direction perpendicular to the first electrode portion, and a third part which is not overlapped with the first and second electrode portions in the vertical direction between the first and second electrode portions.

Advantageous Effects

Embodiments of the invention can improve the reliability of a semiconductor device or a gas sensor by providing a sensor unit activated by light emitted from a light emitting unit as a semiconductor device.

Embodiments of the invention can solve the problems of a durability of a heater or a warm-up time of the heater, by implementing the semiconductor device or the gas sensor using the light of the LED without the heater.

According to the embodiment of the invention, a size of the gas sensor can be reduced by disposing the sensor unit on the light emitting unit.

According to the embodiment of the invention, a size of the semiconductor device can be reduced by disposing the sensor unit on the upper or outer side of the light emitting unit.

Embodiments of the invention may implement a semiconductor device or gas sensor in which a sensor unit is disposed on a light emitting unit of a horizontal chip structure.

Embodiments of the invention may implement a semiconductor device or a gas sensor in which a sensor unit is disposed on a light emitting unit of a flip chip structure.

Embodiments of the invention can implement a semiconductor device or a gas sensor in which a sensor unit is disposed on a light emitting unit of a vertical chip structure.

Embodiments of the invention can improve a sensing sensitivity of the gas sensor.

Embodiments of the invention can downsize a semiconductor device having a gas sensor unit.

Embodiments of the invention can reduce a power consumption of the gas sensor unit.

Embodiments of the invention can improve a reliability of a semiconductor device having a gas sensor unit and a sensing device having the same.

DESCRIPTION OF DRAWINGS

FIG. 1 is a perspective view of a semiconductor device according to a first embodiment of the invention.

FIG. 2 is a plan view of the semiconductor device of FIG. 1.

FIG. 3 is an A-A sectional view of the semiconductor device of FIG. 1.

FIG. 4 is a plan view showing another example of the sensor unit as a modification of the semiconductor device of the first embodiment of the invention.

FIG. 5 is a B-B sectional view of the semiconductor device of FIG. 4.

FIG. 6 is a first modification example of the sensor of a semiconductor device according to an embodiment of the invention.

FIG. 7 is a second modified example of a sensor of a semiconductor device according to an embodiment of the invention.

FIG. 8 is a plan view showing another example of the semiconductor device of FIG. 2.

FIG. 9 is a plan view showing another example of the semiconductor device of FIG. 2.

FIG. 10 is a side cross-sectional view showing another example of the semiconductor device of FIG. 3.

FIG. 11 is a cross-sectional side view representing a third modified example of a semiconductor device having a sensor unit according to the first embodiment.

FIG. 12 is a cross-sectional side view representing a fourth modification example of a semiconductor device having a sensor unit according to the first embodiment.

FIG. 13 is a modification example of the semiconductor device of FIG. 12.

FIG. 14 is a cross-sectional side view representing a fifth modified example of the semiconductor device having the sensor unit according to the first embodiment.

FIG. 15 is a cross-sectional side view representing a sixth modification example of a semiconductor device having a sensor unit according to the first embodiment.

FIG. 16 is a first modification example of the semiconductor device of FIG. 15.

FIG. 17 is a second modification example of the semiconductor device of FIG. 15.

FIG. 27 is a modification example of the semiconductor device of FIG. 25.

FIG. 28 is a perspective view of a semiconductor device having a sensor unit, as another example of a second embodiment of the invention.

FIG. 29 is a cross-sectional side view of the semiconductor device having the sensor unit, as another example of the second embodiment of the invention.

FIG. 30 is a cross-sectional side view of the semiconductor device having the sensor unit, as another example of the second embodiment of the invention.

FIG. 31 is a cross-sectional side view of a gas sensing apparatus having a semiconductor device according to the second embodiment of the invention.

FIG. 32 is a cross-sectional side view of a gas sensing apparatus having a semiconductor device of FIG. 26.

FIG. 34 is a diagram showing the resistance change according to a gas sensing in a semiconductor device according to a second embodiment.

FIG. 35 is a perspective view of a semiconductor device according to a third embodiment.

FIG. 36 is a plan view of the semiconductor device of FIG. 35.

FIG. 37 is a partial enlarged view of the semiconductor device of FIG. 36.

FIG. 38 is an A1-A1 sectional view of the semiconductor device of FIG. 36.

FIG. 39 is a B1-B1 sectional view of the semiconductor device of FIG. 36.

FIG. 40 is another example of a light emitting unit of the semiconductor device in FIG. 36.

FIG. 41 is another example of a light emitting unit in the semiconductor device of FIG. 36.

FIG. 42 is a semiconductor device of FIG. 36, a modification of the light emitting part and the sensor unit electrode structure.

FIG. 43 is a first modification example of a sensor electrode, in the semiconductor device of FIG. 36.

FIG. 44 is a second modification example of a sensor electrode, in the semiconductor device of FIG. 36.

FIG. 45 is a third modification example of a sensor electrode, in the semiconductor device of FIG. 36.

FIG. 46 is an example of a semiconductor device having a plurality of sensors, as a modification example of the semiconductor device in FIG. 36.

FIG. 47 is a view showing an example having a recess in a support substrate, in a semiconductor device according to an embodiment.

FIG. 48 is a view showing an example having a recess to a supporting substrate in the semiconductor device of FIG. 46.

FIG. 49 is a perspective view showing a sensing apparatus having the semiconductor device of FIG. 46, as another example of the third embodiment.

FIG. 50 is a cross-sectional side view of the sensor of FIG. 49.

FIG. 51 is an example of the light emitting unit of the semiconductor device according to a third embodiment.

FIG. 52 shows another example the light emitting unit of the semiconductor device according to the third embodiment.

FIG. 53 is a view for explaining an example gas sensing sensor unit in the third embodiment.

FIG. 54 is a graph showing a resistance change in the sensor unit of the semiconductor device according to the first and third embodiments.

BEST MODE

Figure 18:
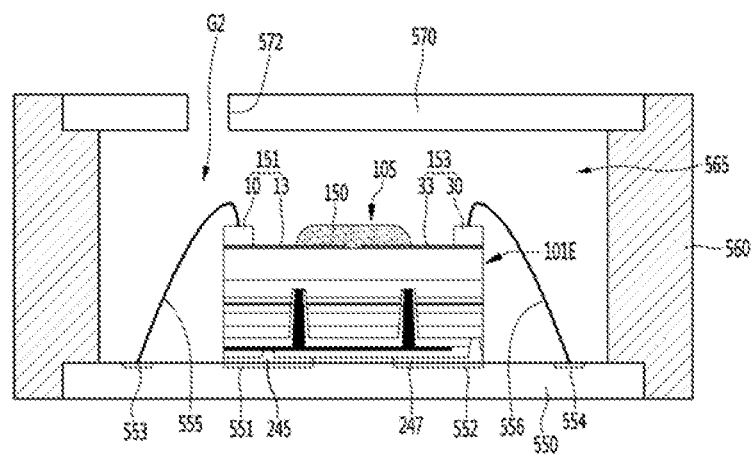
FIG. 18 is a cross-sectional side view representing a detection device having a semiconductor device according to an embodiment.

The embodiments may be modified in other forms or various embodiments may be combined with each other, and the scope of the present invention is not limited to each embodiment described below. Although a description in a particular embodiments is not described in another embodiments, the other embodiments may be understood as being related to the other embodiments unless otherwise described or contradicted by those in the other embodiments. For example, if the features for configuration A are described in a particular embodiment and the features for configuration B are described in another embodiment, even if the embodiment in which configuration A and configuration B are combined is not explicitly described. It is to be understood that they fall within the scope of the invention.

Hereinafter, embodiments of the present invention capable of realizing the above object will be described with reference to the accompanying drawings. In the description of embodiments according to the present invention, in the case of being described as being formed "on or under" of each element, the upper (upper) or lower (lower) or under are all such that two elements are in direct contact with each other or one or more other elements are indirectly formed between the two elements. Also, when expressed as "on or under", it may include not only an upward direction but also a downward direction with respect to one element.

First Embodiment

FIG. 1 is a perspective view of a semiconductor device according to a first embodiment of the invention, FIG. 2 is a plan view of the semiconductor device of FIG. 1, and FIG. 3 is an A-A sectional view of the semiconductor device of FIG. 1.

FIGS. 1 to 3, a semiconductor device according to an embodiment of the invention includes a light emitting unit 101 and a sensor unit 105 on the light emitting unit 101. The semiconductor device may be implemented by the light emitting unit 101 having the sensor unit 105, or by the sensor unit 105 having the light emitting unit 101. The semiconductor device may implement the sensor unit 105 at an overlapped region with the light emitting unit 101 in a vertical direction Z. The light emitting unit 101 in accordance with the embodiment of the invention may be implemented to at least one of a structure of a lateral type chip, a structure of a vertical type chip, a structure of a flip-chip, but the embodiment is not limited thereto. The light emitting unit 101 is, for example, may include a light emitting device. The light emitting device comprises a LED (Light emitting diode), the LED may emit light at least one of ultraviolet, visible or infrared light. The light emitting unit 101 in accordance with the embodiment of the invention may emit an ultraviolet wavelength. In the semiconductor device according to an embodiment of the invention, a distance between the light emitting unit 101 and the sensor unit 105 may be less than or equal to 2 times a thickness of the light emitting unit 101, for example, less than or equal to 1.5 times.

The size of the semiconductor device may be in a range of a breadthwise×lengthwise length of, for example, (300 µm~2500 µm)×(300 µm~2500 µm), (300 µm~5000 µm)×(300 µm~5000 µm) or (300 µm~20000 µm)×(300 µm~20000 µm). A thickness or height of the semiconductor device may be less than or equal to of 500 µm, for example, in a range of 30 µm to 500 µm. A first axial direction is the breadthwise direction or X-axis direction on the plane, a second axial direction may be a length direction or the Y-axis direction perpendicular to the X-axis direction. A three-axis direction is a height or thickness direction, may be the Z-axis direction perpendicular to the first and second axis directions.

The light emitting unit 101 includes a light emitting structure layer 120 having a first conductivity type semiconductor layer 121, active layer 123 and the second conductivity type semiconductor layer 125. The light emitting unit 101 may include a first electrode 141 connected to the first conductivity type semiconductor layer 121 and a second electrode 143 connected to the second conductivity type semiconductor layer 125. The light emitting unit 101 may include a substrate 111. The light emitting structure layer 120 may be disposed on the substrate 111. The sensor unit 105 may correspond to at least one of upper and side surfaces of the light emitting unit 101. The sensor unit 105 may be overlapped with at least one or both the first conductivity type semiconductor layer 121 and the second conductivity type semiconductor layer 125 in the vertical direction. A resistance of the sensor unit 105 may be changed by the light emitted from the light emitting unit 101. The sensor unit 105 may have a conductive or a low resistance by the light emitted from the light emitting unit 101.

The substrate 111 may be a conductive or insulating material. The substrate 111 may be a semiconductor material. The substrate 111 may be a light-transmitting or non-light-transmitting material. The substrate 111 may be selected from the group, such as, a sapphire substrate (Al2O3), GaN, SiC, ZnO, Si, GaP, InP, Ga2O3, or GaAs. The substrate 111 may be formed of a GaN-based semiconductor, for example, GaN semiconductor. The substrate 111 may be a GaN bulk single crystal substrate. The substrate 111 may be used as a support member for supporting the light emitting unit or a semiconductor device.

An upper portion of the substrate 111 may comprise a plurality of protrusions (not shown) protruding toward the light emitting structure layer 120, the protrusion may be formed of a material of the substrate 111, or formed of an insulating material. Side cross-section of the projection may include a semi-spherical shape or a polygonal shape. The protrusions may be improved the light extraction efficiency by changing a critical angle of the light that is incident.

A thickness of the substrate 111 may be in more than 30 μm e.g., in a range of 30 μm to 300 μm, when it is smaller than the thickness of the above range, a handling in manufacturing may be difficult, or it is greater than the thickness of the above range, a size of the light emitting unit is larger. A length of the first axis (X) and a length of the second axis (Y) direction of the substrate 111 may be the same or different. The substrate 111 is, for example, the length of the X-axis direction be greater than the length in the Y-axis direction. The substrate 111 may be removed separately from the light emitting unit 101. The light emitting unit may be provided without the substrate 111, or be removed the substrate.

A semiconductor layer is formed of at least one of a Group III-V semiconductors and Group II-VI compound semiconductors on the substrate 111. The semiconductor layer may be laminated a plurality of layers. Growth equipment of the compound semiconductor layer may be formed by an electron beam evaporator, PVD (physical vapor deposition), CVD (chemical vapor deposition), PLD (plasma laser deposition), thermal deposition of the double type (dual-type thermal evaporator), sputtering, MOCVD (metal organic chemical vapor deposition), but is not limited thereto. A substrate on which the semiconductor layer grown may be a growth substrate or a transparent substrate, a substrate attached additionally on the semiconductor layer may be disposed as a conductive or non-conductive substrate, or light-transmitting or non-light-transmitting material.

Embodiments of the invention may be further disposed a reflective layer under the substrate 111, the reflective may reflects a light traveling in the direction of the substrate to the sensor unit 105. As another example, a concavo-convex structure is disposed on a lower surface of the substrate 111 and/or the reflective layer, and it may be improved light reflection efficiency.

The light emitting structure layer 120 may include a compound semiconductor of group II to VI compound semiconductors e.g., Group II and VI compound semiconductors or a group III and V compound semiconductors. The light emitting structure layer 120 may be disposed on the substrate 111. A lower surface of the light emitting structure layer 120 may be in contact or face the upper surface of the substrate 111. The light emitting structure layer may be further disposed another semiconductor layer between the semiconductor 120 and the substrate 111, but the embodiment is not limited thereto. The light emitting structure layer 120 may include a first conductivity type semiconductor layer 121, active layer 123 and the second conductivity type semiconductor layer 125.

The first conductivity type semiconductor layer 121 may be disposed on the substrate 111. The first conductivity type semiconductor layer 121 comprising dopants of a first conductivity type, for example, include an n-type dopant such as Si, Ge, Sn, Se, or Te. The first conductivity type semiconductor layer 121 comprises a composition formula of $In_xAl_yGa_{1-x-y}N$ ($0 \leq x \leq 1$, $0 \leq y \leq 1$, $0 \leq x+y \leq 1$). The first conductivity type semiconductor layer 121 may be selected from a group III-V compound semiconductors which a first conductivity type dopant is doped, for example, GaN, AlN, AlGaN, InGaN, InN, InAlGaN, AlInN, AlGaAs, GaP, GaAs, GaAsP, or AlGaInP. The first conductivity type semiconductor layer 121 may be formed of a single layer or a multiple layer, but the embodiment is not limited thereto. The first conductivity type semiconductor layer 121 may be each formed of a super-lattice structure in which at least two different layers are alternately disposed. The first conductivity type semiconductor layer 121 may be a contact electrode layer.

The first conductivity type semiconductor layer 121 may have an opening region A1. The opening region A1 may be a region which the active layer 123 and the second conductivity type semiconductor layer 125 is removed in the vertical direction Z.

The active layer 123 may be disposed on the first conductivity type semiconductor layer 121. The active layer 123 may be disposed between the first conductivity type semiconductor layer 121 and the second conductivity type semiconductor layer 125. The active layer 123 is optionally include a single quantum well, a multiple quantum well (MQW), quantum wire, or a quantum dot structure. The active layer 123 includes a cycle of a well layer and a barrier layer. The well layer may comprise a composition formula of $In_xAl_yGa_{1-x-y}N$ ($0 \leq x \leq 1$, $0 \leq y \leq 1$, $0 \leq x+y \leq 1$), and wherein the barrier layer may comprise a composition formula of $In_xAl_yGa_{1-x-y}N$ ($0 \leq x \leq 1$, $0 \leq y \leq 1$, $0 \leq x+y \leq 1$). Period of the well layer/barrier layer may be implemented in, for example, a pair of InGaN/GaN, InGaN/AlGaN, InGaN/InGaN, GaN/AlGaN, InAlGaN/InAlGaN, AlGaN/AlGaN, AlGaAs/GaAs, InGaAs/GaAs, InGaP/GaP, AlInGaP/InGaP, or InP/GaAs. Period of the well layer/barrier layer may be formed in two or more cycles in the pair, and wherein the barrier layer may be formed of a semiconductor material having a wider band gap than the band gap of the well layer. The active layer 123 may be selectively emits light in a wavelength range of from visible light to ultraviolet light, for example, or a peak wavelength of a blue light or a peak wavelength of visible light, but the embodiment is not limited thereto.

The second conductivity type semiconductor layer 125 is disposed on the active layer 123 may include a semiconductor with a dopant of the second conductivity type doping. The second conductivity type semiconductor layer 125 comprises, for example, a composition formula of $In_xAl_yGa_{1-x-y}N$ ($0 \leq x \leq 1$, $0 \leq y \leq 1$, $0 \leq x+y \leq 1$). The second conductivity type semiconductor layer 125 may be formed of at least one semiconductor compound of, such as, GaN, InN, AlN, InGaN, AlGaN, InAlGaN, AlInN, AlGaAs, GaP, GaAs, GaAsP, or AlGaInP. The second conductivity type semiconductor layer 125 is a p-type semiconductor layer, the second conductive dopant may include a p-type dopant of Mg, Zn, Ca, Sr, Ba. The second conductivity type semiconductor layer 125 may be formed of a single layer or a multiple layer, but the embodiment is not limited thereto. The second conductivity type semiconductor layer 125 may be formed of a superlattice structure are alternately disposed at least two layers different from each other. The second conductivity type semiconductor layer 125 may be a contact electrode layer.

As another example of the light emitting structure layer 120, the first and conductivity type semiconductor layer 121 is a p-type semiconductor, and the first may be the second conductivity type semiconductor layer 125 is an n-type semiconductor. The light emitting structure layer 120 may comprise at least one of a p-n junction, n-p junction, n-p-n junction, or p-n-p junction structure according to a junction form. Wherein the p is a p-type semiconductor layer, wherein the n is an n-type semiconductor layer, the n-p junction or p-n junction has an active layer, a region between the n-p-n junction, or p-n-p junction may have at least one active layer in between n-p or p-n.

The light emitting structure layer 120 may further include other layers and/or under of the layer, but the embodiment is not limited thereto. The upper surface area of the light emitting structure layer 120 may be narrower than a lower surface area thereof. The area of the lower surface of the light emitting structure layer 120 may be equal to or smaller than area of the upper surface of the substrate 111. Here, the area may be an area of the X-axis and Y-axis plane. Side surfaces of the light emitting structure layer 120 may be inclined surface relative to the perpendicular axial direction (Z), and the inclined surface may be improved light extraction efficiency.

Electrode structure of the light emitting unit 101 in according to the embodiment of the invention may comprise a first and second electrodes 141 and 143, and a conductive layer 131. The first electrode 141 may be electrically connected to the first conductivity type semiconductor layer 121. The first electrode 141 may be implemented in a pad. The first electrode 141 may be disposed on a portion of the first conductivity type semiconductor layer 121. The first electrode 141 may be disposed at a lower region than the second electrode 143, and may be face a side surface of the active layer 123. The first electrode 141 may be formed of at least one or a selective alloy of a titanium (Ti), copper (Cu), nickel (Ni), gold (Au), chrome (Cr), tantalum (Ta), platinum (Pt), tin (Sn), silver (Ag), aluminum (Al), phosphorous (P), and it may be formed in a single layer or multiple layers.

The second electrode 143 may be disposed on the second conductivity type semiconductor layer 125. The second electrode 143 may be electrically connected to at least one of the conductive layer 131 and the second conductivity type semiconductor layer 125. The second electrode 143 may be implemented in a pad. The second electrode 143 may be formed of at least one or a selective alloy of titanium (Ti), copper (Cu), nickel (Ni), gold (Au), chrome (Cr), tantalum (Ta), platinum (Pt), tin (Sn), silver (Ag), aluminum (Al), phosphorous (P), and it may be formed in a single layer or multiple layers. The first and second electrodes 141 and 143 may be spaced apart in the horizontal direction on the light emitting structure layer 120.

The conductive layer 131 may be disposed on the light emitting structure layer 120. The conductive layer 131 is disposed at least one or both of a region between and the second conductivity type semiconductor layer 125 and the second electrode 143 and a region between the first conductivity type semiconductor layer 121 and the first electrode 141. The conductive layer 131 is disposed, for example, on the second conductivity type semiconductor layer 125, and electrically connected to the second conductivity type semiconductor layer 125 and the second electrode 143.

The conductive layer 131 may be implemented in a transparent layer or a reflective material layer. The conductive layer 131 may include at least one of metal, non-metal or a semiconductor. The conductive layer 131 is metal, for example, it may be formed of a metal or alloy including at least one of Ag, Ni, Al, Rh, Pd, Ir, Ru, Mg, Zn, Pt, Cu, Au, Hf, and may be formed in a single layer or multiple layers. The conductive layer 131 may include an non-metal, e.g., a metal oxide and a metal nitride. The metal oxide or metal nitride may include at least one of a material of ITO (indium tin oxide), ITON (ITO nitride), IZO (indium zinc oxide), IZON (IZO nitride), IZTO (indium zinc tin oxide), IAZO (indium aluminum zinc oxide), IGZO such as (indium gallium zinc oxide), IGTO (indium gallium tin oxide), AZO (aluminum zinc oxide), ATO (antimony tin oxide), GZO (gallium zinc oxide), ZnO, IrOx, RuOx, NiO. The conductive layer 131 may be removed from the light emitting unit 101. When the conductive layer 131 may be a metallic material, it may be for light transmission formed with a thickness of 10 nm or less, for example, 1 nm to 5 nm. As another example, the conductive layer 131 may be removed, in this case, the second electrode 143 may be contacted with the upper surface of the second conductivity type semiconductor layer 125 of multi-layers. The conductive layer 131 may be formed of an AlGaN-based semiconductor to reduce ohmic contact and light absorption loss, but the invention is not limited thereto.

The insulating layer 113 may be disposed between the light emitting unit 101 and the sensor unit 105. The insulating layer 113 may be disposed between the conductive layer 131 and the sensor unit 105. When the conductive 131 is removed, the insulating layer 113 may be disposed between the light emitting structure layer 120 and the sensor unit 105. The insulating layer 113 may be formed of a single layer or a multiple layer by using a dielectric material. The insulating layer 113 may include an insulating material or an insulating resin formed at least one of oxide, a nitride, a fluoride, and a sulfide having at least one of Al, Cr, Si, Ti, Zn, Zr. The insulating layer 113 may be selectively formed of, for example, $SiO_2$, $Si_3N_4$, $Al_2O_3$, $TiO_2$, or MgO. The insulating layer 113 may be disposed around the second electrode 143. Part of the insulating layer 113 and 113A may extend to a periphery of the first electrode 141. The insulating layer 113 may be electrically isolated between the sensor unit 105 and the light emitting unit 101. The upper surface area of the insulating layer 113 may be provided at a larger area than the bottom surface area of the sensor unit 105. The insulating layer 113 may transmit the light emitted from the light emitting unit 101. A thickness of the insulating layer 113 may be equal to less than 5 μm, for example, in a range of 1 μm to 2 μm, when it is smaller than the above range, an interference between the light emitting unit 101 and the sensor 105 occurs, and when it is larger than the above range, the material is waste or a thickness sensor may be increased.

The sensor unit 105 may be electrically separated from the light emitting unit 101. The sensor unit 105 may be a sensor for detecting whether or not the gas in response to the light emitted from the light emitting unit 101. The sensor unit 105 may be disposed on the insulating layer 113. Here, the insulating layer 113 may be a protective layer or a base layer of the sensor unit 105.

The sensor unit 105 includes a plurality of sensor electrodes 151 and 153 and a sensing material 150 connected to the plurality of sensor electrodes 151 and 153.

The plurality of sensor electrodes 151 and 153 may be disposed on the insulating layer 113 disposed on the light emitting structure layer 120. The plurality of sensor electrodes 151 and 153 may include a first sensor electrode 151 and a second sensor electrode 153 separated from each other. The first and second sensor electrodes 151 and 153 may be formed of a metal or alloy including at least one of Ag, Ni, Al, Rh, Pd, Ir, Ru, Mg, Zn, Pt, Cu, Au, Hf, Mo, W, TiN, Cr, and may be formed of a single layer or multiple layers.

The first sensor electrode 151 may include a first pad portion 10 and a first extension part 13 extending in a direction of the sensing material 150 from the first pad portion 10. The first pad portion 10 is electrically connected to the external terminal, for example, may be connected to a wire. The first pad portion 10 is of a thickness greater than a thickness of the first extension part 13, or may further comprise a bonding layer, but the embodiment is not limited thereto.

As shown in FIG. 2, a top view shape of the first pad portion 10 may be formed in a circular shape, an oval shape or a polygonal shape. The upper surface area of the first pad portion 10 may be, for example, equal to or greater than a size which a ball of the wire may be bonded, and may have a greater width than a pattern width of the first extension part 13.

The second sensor electrode 153 may include a second pad portion 30 and a second extension part 33 extending in a direction of the sensing material 150 from the second pad portion 30. The second pad portion 30 is electrically connected to external terminals, such as may be connected to the wire. The second pad portion 30 has a thickness greater than a thickness of the second extension part 33, or may further comprise a bonding layer, but the embodiment is not limited thereto.

Top view shape of the second pad portion 30 may be formed in a circular shape, an oval shape or a polygonal shape. The upper surface area of the second pad portion 30 may be, for example, equal to or greater than the size which the ball (Ball) of the wire may be bonded, and may have a larger width than a pattern width of the second extension part 33.

The first and second extension parts 13 and 33 may be formed to a thickness more than 100 nm, for example, 200 nm thick or more, but the embodiment is not limited thereto. The first and second pad portions 10 and 30 may be disposed thicker than the thickness of the first and second extension parts 13 and 33.

The first extension part 13 may be extending from the first pad portion 10 and may contact the sensing material 150. The second extension part 33 may be extending from the second pad portion 30 in a direction the first extension part 13 and may contact the sensing material 150. The first and second extension parts 13 and 33 may be spaced from each other at a predetermined interval D1. The sensing material 150 may be disposed on the first and the second extension parts 13 and 33. A plurality of first extension parts 13 may extend in a direction of the second extension part 33 or the second pad portion 30. Each of the plurality of second extension parts 33 may be disposed between the first extension parts 13. One or plurality of first extension parts 13 may be extended through a region of the sensing material 150 in the horizontal direction, and one or plurality of the second extension part 33 may be extended through the sensing material 150 in the horizontal direction.

It will be described in detail for the first and the second extension part 13 and 33. The first extension part 13 may include a first branched part 11 extending toward the second axial direction from the first pad portion 10, and a first line pattern 12 extending toward the first axial direction from the first branched part 11. The first line pattern 12 may include a plurality of metal lines, and the first line pattern 12 may be extended at an angle, for example, an angle of 60 degrees to 120 degrees with respect to the first branched part 11. At least two of metal lines of the first line pattern 12 may be spaced apart at a predetermined interval. An interval of metal lines of the first line patterns 12 may be at least twice the interval D1 between adjacent line patterns 12 and 32.

The second extension part 33 may include a second branched part 31 extending toward the second axial direction from the first pad portion 10, and a second line pattern 32 extending toward the first axial direction from the second branched part 31. The second line pattern 32 includes a plurality of metal lines, and the plurality of metal lines may be extended by a predetermined angle, for example, an angle of 60 degrees to 120 degrees with respect to the second branched part 31. At least two of the metal lines of the metal line pattern 32 may be spaced apart at a predetermined interval. An interval between the second line patterns 32 may be at least twice the interval D1 between adjacent line patterns 12 and 32.

An extending direction of the first branch portions 11 of the first sensor electrode 151 and an extending direction of the second branch portions 31 of the second sensor electrode 153 may be disposed in parallel with each other along the second axis direction Y. The first line pattern 12 and the second line pattern 32 may be disposed in parallel with each other along the first axis direction. The metal line of the first line pattern 12 and the metal line of the second line pattern 32 may be disposed alternately, for example, when a first metal line may be the metal lines of the first line pattern 12 and a second metal may be the metal lines of the second line pattern 32, and a form of the first metal line/the second metal line/the first metal line/the second metal lines may be arranged.

Line widths D2 and D3 of the first and second the line pattern 12 and 32 may be, for example, more than 5 μm e.g., range from 5 μm to 100 μm. When the line widths D2 and D3 of the first and second line patterns 12 and 32 is less than the above range, a sensing sensitivity reduction may be lowered and a resistance value may be increased.

The Interval D1 between the first and second line patterns 12 and 32 may be in more than 5 μm for example, range from 5 μm 200 μm. When the interval D1 between the first and second line patterns 12 and 32 is smaller than the range, the reliability of the sensor due to the interference between adjacent patterns than, when the interval D1 is greater than the range, a size of the sensor unit 105 is increased and a sensing sensitivity may be lowered. The resistance value for the gas measurement may be determined according to the interval D1 between the first and second line patterns 12 and 32, the resistance value decreases as the interval D1 between the first and second line patterns 12 and 32 decreases.

The first and second sensor electrodes 151 and 153 may include a material such as a nanopowder, nanowire, nanorod, carbon nanotubes (CNTs), and graphene, and the embodiment is not limited thereto.

The sensing material 150 may be disposed a region between the first and second pad portions 10 and 30. The sensing material 150 may be disposed to be overlapped with the first and second extension parts 13 and 33 in a vertical direction z.

The sensing material 150 may be connected to the first and second sensor electrodes 151 and 153. The sensing material 150 may be in contact with the first and second sensor electrodes 151 and 153. The sensing material 150 may be in contact with the insulating layer 113. The sensing material 150 may be physically separated from the light emitting structure layer 120.

The sensing material 150 may be disposed on the first extension part 13 of the first sensor electrode 151, and the second extension part 33 of the second sensor electrode 153. The sensing material 150 may be a resistance change by the light emitted from the light emitting unit 101. The sensing material 150 may have a lower resistance or conductivity by the light emitted from the light emitting unit 101.

As shown in FIG. 2 and FIG. 3, the sensing material 150 may be disposed on the first and the second extension part 13 and 33. The sensing material 150 includes a first region R1 overlapped with at least one of the first and the second extension parts 13 and 33 in the vertical direction, and a second region R2 that is not overlapped with at least one of the first and second extension parts 13 and 33 in the vertical direction. The second region R2 may be projected in a direction of the light emitting structure layer 120, or/and a direction of the substrate. The second region R2 may be disposed between the first and the second extension part 13 and 33. The first and second regions R1 and R2 may be alternately arranged to have a predetermined length. A portion of the second region R2 has the same width as the interval D1 between the first and the second extension part 13 and 33. The second region R2 may be extended to have a long length in one direction, and the extending direction of the second region R2 is arranged in parallel with the extending direction of the first and second extension parts 13 and 33. The interval D1 between the first and the second extension part 13 and 33 may be 5 µm or more, for example, in a range from 5 µm to 200 µm. When the interval D1 of the first and second extension parts 13 and 33 is less than the above range, the reliability of the sensor may be lowered by the interference between the adjacent extensions 13 and 33, when the interval D1 is greater than the above range, a size of the sensor unit 105 increases or a sensing sensitivity may be lowered. The resistance value for the gas measurement may be determined according to the interval D1 between these first and second extension parts 13 and 33, and as the interval D1 between the first and the second extension part 13 and 33 becomes closer to each other, the resistance value of the sensing material 150 may be lowered.

The sensing material 150 may be in contact with the first and the second extension part 13 and 33 at a region between the first and the second extension part 13 and 33. Since the sensing material 150 has a low resistance or conductivity due to the light L1 emitted from the light emitting unit 101, and the sensing material 150 may electrically connect between adjacent first and second extension parts 13 and 33. The sensing material 150 may have a first resistance by the incident light from the light emitting unit 101, and may be changed to a second resistance lower than the first resistance when an external gas G2 is introduced. Accordingly, the sensing material 150 is lowered to give an electrical resistance between the first and the second extension part 13 and 33 by the light L1 and the gas G2, and may electrically connect the first and second extension parts 13 and 33 through the second region R2. Since the first and second extension parts 13 and 33 are electrically connected by the sensing material 150, and the resistance between the first and the second extension part 13 and 33 is reduced, the resistance may be detected by the first and second sensors electrode 151 and 153. The change in the detection resistance may measure the presence or absence of the gas by the semiconductor device.

The first and second regions R1 and R2 of the sensing material 150 may be overlapped with the light emitting structure layer 120 in the vertical direction. The first and second region R1 and R2 of the sensing material 150 may be overlapped with the active layer 123 in the vertical direction.

The sensing material 150 may be disposed on the first line pattern 12 of the first extension part 13 and the second line pattern 32 of the second extension part 33. A bottom of the sensing material 150 may be disposed to a region of the upper surface of the first and second line patterns 12 and 32 and a region between the first and second line patterns 12 and 32. The sensing material 150 may disposed on formed on the upper surface of the upper surface of the insulating layer 113 or the upper surface of the light emitting unit 101 in a region excluding the second electrode 143 and the first and second pad portions 10 and 30, but is not limited thereto.

A bottom length of the sensing material 150 in the second axial direction Y may be greater or smaller than a distance between the outermost first and second line patterns 12 and 32 of the first and second extending portions 13 and 33 in the Y axis direction. The bottom length of the sensing material 150 in the first axis direction X may be longer or smaller than the length of each line pattern 12 and 32 in the X-axis direction. Since the gas sensing is possible even if the sensing material 150 is disposed in the region between the adjacent pair of line patterns 12 and 32, the amount and position of the sensing material 150 may be adjusted.

The extending directions of the first and second line patterns 12 and 32 may be arranged in a direction parallel to the direction of a virtual straight line connecting the first and second electrodes 141 and 143. Accordingly, since the center region between the first and second electrodes 141 and 143 and the sensing material 150 overlap in the vertical direction, The amount of light emitted through the light emitting structure layer 120 and incident in the sensing material 150 may be increased.

The sensing material 150 may be formed of a metal oxide material. The sensing material 150 may include a main sensing material and a catalyst. The main sensing material comprises a metal oxide material, the catalyst may comprise a metal. The main sensing material may include, for example, at least one or two or more of $SnO_2$, $CuO$, $TiO_2$, $In_2O_3$, $ZnO$, $V_2O_5$, $RuO_2$, $WO_3$, $ZrO_2$, $MoO_3$, $NiO$, $CoO$, $Fe_2O_3$, and $AB_2O_4$, and may be formed of various materials not limited to this. The catalyst of the sensing material 150 may include, for example, at least one or two or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), Ruthenium (Ru), rhodium (Rh), silver (Ag), hafnium (Hf), tantalum (Ta), tungsten (W), rhenium (Re), iridium (Ir). The catalyst material may be a doping material in the sensing material 150, and mixed with the main sensing material. The sensing material 150 may include a material that may have both of sensing and catalytic properties. The material of the sensing material 150 in accordance with an embodiment of the invention may optionally be mixed with materials of the main sensing material and the catalyst according to the type of gas to be detected. The detection by the sensor unit 105 may mean not only the presence or absence of the measurement gas, but also the change in the concentration of the measurement gas.

The sensing material 150 is in contact with a surface of the first and second sensor electrodes 151 and 153 to reduce an impedance change. The sensing material 150 may be mixed in one type or two or more types of main sensing material, and doped with one or two types of catalyst materials in the mixed material. The catalyst material may be added in an amount of 5 wt % or less, for example, in a range of 1 wt % to 5 wt % of the main sensing material, and the gas sensing sensitivity may be lowered when the catalyst material exceeds the above range. For example, when $SnO_2$ and ZnO are mixed, in the sensing material 150, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt % to 3 wt % of the main sensing material. Here, since $SnO_2$ has a band gap of about 3.6 eV, a photo current may be formed when light emitted from the light emitting unit 101 is 340 nm. A particle size of the main sensing material is 30 nm or more, for example, in a range of 30 nm to 60 nm. When the particle size is small, characteristics may be improved, but costs may be increased, and when the particle size is larger than the above range, surface energy becomes small, and thus oxygen vacancies may not be formed.

Figure 19:
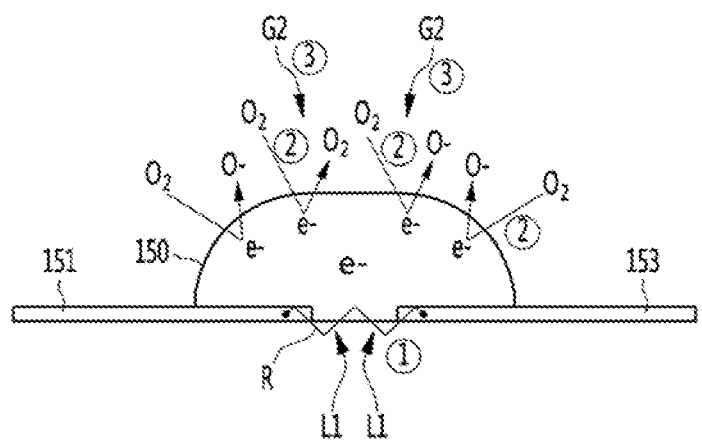
FIG. 19 is a view for explaining an example of a gas sensing of the sensor unit in the first embodiment.

The sensor unit 105 according to an embodiment of the invention as shown in FIGS. 3 and 19, when the light L1 is irradiated from the light emitting member 101 (Step ①), electronic (e-) by the sensing material 150 occurs (Step ②), and at this time, the sensing material 150 may be firstly reacted with nitrogen or oxygen which occupies the largest composition ration in the atmosphere (Step ③). The nitrogen does not react with the sensing material 150 of the semiconductor device as an inert gas, and oxygen is adsorbed on the surface of the sensing material 150 to exist in the form of oxide ions such as O2-, O2-, and O—. At this time, the oxide ions and the gas G2 react with each other to move electrons. At this time, a very large change in impedance, that is, a high sensitivity characteristic, may occur depending on the electron movement on the surface of the sensing material 150. That is, the sensing material 150 generates oxidized ions by the reaction of the electrons generated in response to the light L1 and oxygen, and the generated oxidized ions react with the gas G2 to form the sensing material 150, so that the electrons may be moved. The movement of electrons in the sensing material 150 may reduce the resistance changing the resistance R between the first and second sensor electrodes 151 and 153, and the change in resistance of the sensing material 150 may be detected by the sensor electrodes 41 and 43. The sensing material 150 may have conductivity by the light L1 and the conductive property may be further improved when the gas G2 is sensed. For example, the resistance of the sensing material 150 may be lowered. The first and second sensor electrodes 151 and 153 may be electrically connected to each other by the sensing material 150. As shown in FIG. 54, the sensing resistance level of the semiconductor device can be changed to low/high according to ON/OFF of the ultraviolet UV rays. The gas may include $H_2$, $CO_2$, CO, HCl, $Cl_2$, $H_2S$, HCN, $NH_3$, $C_3H_8$, $C_4H_{10}$, $CH_4$, and the like. The sensing material 150 may be a semiconductor ceramic material and may have resistance values ranging from several hundreds of kW to several tens of MW through process and heat treatment.

The sensor unit 105 according to an embodiment of the invention is overlapped with the light emitting unit 101 in the Z-axis direction, the light incidence efficiency of the sensor unit 105 may be increased. Accordingly, the operational reliability of the sensor unit 105 may be improved.

Since the sensor unit 105 according to an embodiment of the invention disposed in a region adjacent to light emitting unit 101 or to the active layer 123 of the light emitting unit, it is possible to provide a light intensity to be irradiated with a stable. Since a distance between the sensor unit 105 and the active layer 123 may have 7 µm or less, for example, in a range of 2 µm to 7 µm, a decrease in an amount of light and the intensity of the irradiated light may be minimized and the reliability of the semiconductor device may be improved.

The sensing material 150 of the sensor unit 105 according to the embodiment of the invention may change the resistance between the first and second line patterns 12 and 32 of the first and second sensor electrodes 151 and 153, and it is possible to detect whether or not gas is detected by the second sensor electrodes 151 and 153. For example, when gas is detected in the sensing material 150, the resistance value is lowered and the resistance value may be detected by the first and second sensor electrodes 151 and 153 having the first and second line patterns 12 and 32. Or if the sensing material 150 is free of gas, the sensing material 150 may be an insulation resistance. When the change in the resistance value of the sensing material 150 is changed by about 2%, the first and second sensor electrodes 151 and 153 may detect the gas sensing.

Since the semiconductor device according to an embodiment of the invention uses the light of the light emitting unit 101, a price can be lowered, the reliability of the thermal shock may be prevented without using a heater, and a complexity problem of other MEMS (Microelectromechanical systems) processes or packaging in the membrane structure may be reduced. The semiconductor device according to the first embodiment of the invention may not be provides with separate support substrate in the semiconductor device, since the sensor unit 105 for gas sensing is disposed on the LED, for example, the light emitting unit 101 having the substrate.

The sensing material 150 of sensor unit 105 according to an embodiment of the invention may be implemented with an area of 0.5% or more with respect to the upper surface area of the active layer 123. This may be even arranged only in the region between sensing material 150 are in contact at least a pair of first and second line patterns 12 and 32 which detects a resistance change due to the sensing material 150.

When the light emitting unit 101 in accordance with an embodiment of the invention that emits ultraviolet light, an ultraviolet LED chip has a characteristic that the light output of the corner region is lower than the center region. Accordingly, the sensing material 150 may be disposed on the center region rather than the peripheral region of the light emitting unit 101. The peripheral region may include a region adjacent to each edge of the light emitting unit 101.

Since the first and second sensor electrodes 151 and 153 are disposed on the light emitting unit 101, the first and second pad portions 10 and 30 may be freely disposed on the edge region of the light emitting unit 101.

FIG. 4 is a modification of the first embodiment of the invention and is another modification of the sensor unit of FIG. 2, FIG. 5 is a B-B cross-sectional view of the semiconductor device of FIG. 4. In describing these modified examples, the configuration of the modification example is the same as that of the above configuration, and the configuration of the above embodiment can be selectively used with reference to the above description.

As shown in FIGS. 4 and 5, the sensor unit 105 includes first and second sensor electrodes 151 and 153 and a sensing material 150.

The first sensor electrode 151 includes a first pad portion 10 and the first extension part 13, and the second sensor electrode 153 includes the second pad portion 30 and the second extension part 33.

The sensing material 150 may be a resistance change by the light emitted from the light emitting unit 101. The sensing material 150 may have a lower resistance or conductivity by the light emitted from the light emitting unit 101. The sensing material 150 may be disposed on the first and the second extension part 13 and 33. The sensing material 150 may include a first region R1 overlapped with at least one of the first and the second extension part 13 and 33 in the vertical direction Z, and a second region R2 that is not overlapped with the first and second extension parts 13 and 33 in the vertical direction. The second region R2 may be projected in a direction of the light emitting structure layer 120, or/and a direction of the substrate. The second region R2 may be disposed between the first and the second extension part 13 and 33. A portion of the second region R2 has the same width as an interval D1 between the first and the second extension parts 13 and 33. The second region R2 may be extended to have a long length in one direction, and the extending direction of the second region R2 is arranged in parallel with the extending direction of the first and second extension parts 13 and 33. The interval D1 between the first and the second extension part 13 and 33 may be 5 μm or more, for example, in a range from 5 μm to 200 μm. When the interval D1 of the first and second extension parts 13 and 33 is less than the above range, the reliability of the sensor may be lowered by the interference between the adjacent extensions 13 and 33, when the interval D1 is greater than the above range, a size of the sensor unit 105 increases or a sensing sensitivity may be lowered. The resistance value for the gas measurement may be determined according to the interval D1 between these first and second extension parts 13 and 33, and as the interval D1 between the first and the second extension part 13 and 33 becomes closer to each other, the resistance value of the sensing material 150 may be lowered.

The sensing material 150 may be in contact with the first and the second extension part 13 and 33 at a region between the first and the second extension part 13 and 33. Since the sensing material 150 has a low resistance or conductivity due to the light L1 emitted from the light emitting unit 101, and the sensing material 150 may electrically connect between adjacent first and second extension parts 13 and 33. The sensing material 150 may have a first resistance by the incident light from the light emitting unit 101, and may be changed to a second resistance lower than the first resistance when an external gas G2 is introduced. Accordingly, the sensing material 150 is lowered to give an electrical resistance between the first and the second extension part 13 and 33 by the light L1 and the gas G2, and may electrically connect the first and second extension parts 13 and 33 through the second region R2. Since the first and second extension parts 13 and 33 are electrically connected by the sensing material 150, and the resistance between the first and the second extension part 13 and 33 is reduced, the resistance may be detected by the first and second sensors electrode 151 and 153. The change in the detection resistance may measure the presence or absence of the gas by the semiconductor device.

The first and second regions R1 and R2 of the sensing material 150 may be overlapped with the light emitting structure layer 120 in the vertical direction. The first and second region R1 and R2 of the sensing material 150 may be overlapped with the active layer 123 in the vertical direction.

The first and second pad portions 10 and 30 may be disposed at both sides of the sensing material 150. The length of the first axial direction X on the bottom surface of the detected member 150 may be greater or smaller than the distance between the outermost first and second line patterns 12 and 32 of the first and second extension parts 13 and 33. The length of the second axial direction Y in the bottom surface of the sensing material 150 may be longer or smaller than the length of the Y-axis direction of each line patterns 12 and 32. Since the gas sensing is possible even if the sensing material 150 is disposed in the region between the adjacent pair of line patterns 12 and 32, the amount and position of the sensing material 150 may be adjusted.

A bottom shape of the sensing material 150 may be a circular shape, a polygonal shape, or elliptical shape, the side cross-section may be a semi-spherical shape, a polygonal shape, or elliptical shape.

The first pad portion 10 may be connected to the center region of the first extension part 13, and the second pad portion 30 may be connected to the center region of the second extension part 33. The first and second pad portions 10 and 30 may be disposed in the same straight line in the Y-axis direction, but the embodiment is not limited thereto.

The first and second extension parts 13 and 33 are disposed such that the first and second line patterns 12 and 32 are alternately arranged in a tooth structure, and a portion of the sensing material 150 is disposed on the first and second line patterns and may be disposed between the first and second line patterns. Accordingly, when the light of the light emitting unit is irradiated to the sensing material 150, the resistance value depending on whether the external gas is sensed may be changed. The change of the resistance value may electrically connect the first and second line patterns 12 and 32 that are in contact with the sensing material 150.

A virtual straight line connecting the first and second pad portions 10 and 30 of the first and second sensor electrodes 151 and 153 is disposed in a direction orthogonal to the direction of a virtual straight line connecting the first and second electrodes 141 and 143. The extending directions of the first and second line patterns 12 and 32 may be arranged in a direction parallel to the direction of a virtual straight line connecting the first and second electrodes 141 and 143. Accordingly, since the center region between the first and second electrodes 141 and 143 and the sensing material 150 overlap in the vertical direction. The amount of light emitted through the light emitting structure layer 120 and incident in the sensing material 150 may be increased.

In the embodiment, a reflective layer may be further disposed under the substrate 111 to reflect light traveling toward the substrate to the sensor unit 105. As another example, the substrate 111 may be disposed on the lower surface of the substrate 111 and/or the concavo-convex structure of the reflective layer to improve the light reflection efficiency.

As shown in FIG. 6, the sensor unit 105 includes a first and second sensor electrodes 151 and 153 and a sensing material 150.

The first sensor electrode 151 includes a first pad portion 10 and a first extension part 13, and the second sensor electrode 153 includes a second pad portion 30 and a second extension part 33. The sensing material 150 may cover more than 80% of the first and second extension parts 13 and 33. The sensing material 150 may be disposed in form to cover the first and second line patterns 12 and 32 of the first and second extension parts 13 and 33. The sensing material 150 may be disposed in a center region of the light emitting unit and may transmit a change in resistance value according to gas sensing through the first and second sensor electrodes 151 and 153 in response to the incident light. Although the embodiment does not show the first and second electrodes of the light emitting unit as shown in FIG. 2, the configuration of the embodiment can be selectively used.

FIG. 7 is a modification of the sensor unit 105 according to the embodiment, and a size of the first and second sensor electrodes 151 and 153 are modified.

As shown in FIG. 7, the sensor unit 105 includes first and second sensor electrodes 151A and 153A and a sensing material 150.

The first sensor electrode 151A may be disposed in a 20% or more, for example, in a range from 25% to 40% of the upper surface area of the light emitting unit. The second sensor electrode 153A may be formed of 20% or more, for example, in a range from 25% to 40% of the upper surface area of the light emitting unit. The first sensor electrode 151A and the second sensor electrode 153A may be formed in a symmetrical shape.

The first and second sensor electrodes 151A and 153A are spaced apart by a predetermined interval D4 from the first and second sensor electrodes 151A and 153A without extending portions such as the line pattern described above. The sensing material 150 is disposed on the sensor electrodes 151A and 153A. The interval D4 may be in a range of 100 μm or more, for example, 100 μm to 200 μm. The gas type and the resistance value may be determined according to the interval D4 and the components of the sensing material 150. A portion of the sensing material 150 may be disposed in a region between the first and second sensor electrodes 151A and 153A. The first and second sensor electrodes 151A and 153A may be disposed on the insulating layer 113. A predetermined region of the first and second sensor electrodes 151A and 153A may be used as a pad region or may be formed a separate pad region, but the embodiment is not limited thereto.

A region between the first and second sensor electrodes 151A and 153A may be disposed to have a length in one direction. A direction between the first and second sensor electrodes 151A and 153A may be a direction corresponding to at least one or both of the first and second electrodes 141 and 143. Accordingly, when light is incident from the light emitting unit through the region between the first and second sensor electrodes 151A and 153A, the resistance value of the sensing material 150 is changed, and the first and second sensor electrodes 151A and 153A may detect a change of the resistance value by the first and second sensor electrodes 151A and 153A. Thus, the presence or absence of gas by the semiconductor device may be detected.

FIG. 8 is a modification example of FIG. 2, and a second electrode 143 may include a branch electrode 143A. The branch electrode 143A may be disposed in one or plural. The branch electrode 143A may extend in a direction of a first electrode 141 with respect to the second electrode 143. The branch electrode 143A may be disposed between the insulating layer 113 and the light emitting structure layer 120. The branch electrode 143A may be disposed between the insulating layer 113 and the conductive layer (131 of FIG. 3).

The sensor unit 105 may include first and second sensor electrodes 151 and 153 and a sensing material 150.

The first and second sensor electrodes 151 and 153 include first and second line patterns 12 and 32, and the first and second line patterns 12 and 32 may be arranged in plural. The first and second line patterns 12 and 32 may be arranged in parallel with each other. At least one or both of the first and second line patterns 12 and 32 may be disposed in parallel with the branch electrode 143A.

At least one of the plurality of first line patterns 12 may be disposed to be overlapped with the branch electrode 143A of the second electrode 143. For example, the first line patterns 12 may include a pattern 12A overlapped with the branch electrode 143A, and a pattern 12B disposed between the branch electrodes 143A and not overlapped with the branch electrodes 143A. Accordingly, reflection or absorption loss of light emitted from the light emitting unit may be reduced, and an amount of light incident in the sensing material 150 may be improved. Intervals between the first and second line patterns may be equal to each other, but the invention is not limited thereto. As another example, although an example in which a part of the first line pattern 12 is overlapped with the branch electrode 143A of the second electrode 143 has been described, a part of the second line pattern 32 may be overlapped with the branch electrode 143A of the second electrode 143.

FIG. 9 is another example of FIG. 8, and a second electrode 143 may include one or a plurality of branch electrodes 143A. A sensor unit 105 may include first and second sensor electrodes 151 and 153 and a sensing material 150.

The branch electrode 143A may extend at a predetermined length in a direction of a first electrode 141 with respect to the second electrode 143. The branch electrode 143A may be disposed between the insulating layer 113 and the light emitting structure layer 120. The branch electrode 143A may be disposed between the insulating layer 113 and the conductive layer (131 of FIG. 3).

The second electrode 143 and the sensor unit 105 may be disposed on the insulating layer 113. The sensor unit 105 includes the first and second sensor electrodes 151 and 153 and the sensing material 150. The first sensor electrode 151 includes a first pad portion 10 and a first extension part 13, and the second sensor electrode 153 includes a second pad portion 30 and a second extension part 33. The first and second extension parts 13 and 33 may include first and second line patterns 12 and 32 disclosed in an embodiment.

The branch electrode 143A of the second electrode 143 may be disposed to be overlapped with a part of the first and second line patterns 12 and 32 in the vertical direction. Accordingly, the sensing material 150 may be disposed on the first and second line patterns 12 and 32 and in a region between the first and second line patterns 12 and 32. An operation of the sensor unit 105 will be described with reference to the above-disclosed description. Since the first and second line patterns 12 and 32 may include a pattern overlapped with the branch electrode 143A and a pattern not overlapped with the branch electrode 143A, an amount of incident light is increased, but an influence on operating characteristics of the sensing material 150 may be minimized.

FIG. 10 is a side cross-sectional view showing another example of the semiconductor device of FIG. 3. In describing this example, the same configuration as the above will be described with reference to the above description, and some configurations may be selectively used.

Referring to FIG. 10, a first part A1 of a light emitting unit 101 may be a region in which a first electrode 141 is disposed, and may be a stepped region lower than an upper surface of the light emitting unit 101. A second part A2 of the light emitting unit 101 may be a stepped region lower than the upper surface of the light emitting unit 101. The first and second parts A1 and A2 of the light emitting unit 101 may be disposed in different regions or may be disposed in adjacent regions. One side of a first conductivity type semiconductor layer 121 may be exposed in the first part A1 of the light emitting unit 101, and may be electrically connected to the first electrode 141.

An insulating layer 113 is disposed along an upper surface and a side surface of the light emitting structure layer 120, and parts 131A and 131B are disposed on the first and second parts A1 and A2, and thus electrical contact with another material layer may be blocked. Here, a depth T1 of the first and second parts A1 and A2 may be a depth in the Z-axis direction on the upper surface of the light emitting unit 101, and may be equal to each other.

The other side of the first conductivity type semiconductor layer 121 may be disposed in the second part A2 of the light emitting unit 101, and a sensor unit 105 may be disposed on the other side of the first conductivity type semiconductor layer 121. The sensor unit 105 includes first and second sensor electrodes and a sensing material 150 disclosed in an embodiment. At least one example of the configurations disclosed above may be applied to the first and second sensor electrodes.

The sensor unit 105 may correspond to a side surface of the active layer 123. The sensor unit 105 may be disposed in a region not overlapped with the active layer 123 in the vertical direction. Here, the sensor unit 105 is disposed on the side surface of the light emitting structure layer 120, and thus an amount of incident light may be reduced as compared with the structure of FIG. 1. For this, a reflective layer may be further disposed under the substrate 111 to reflect light traveling toward the substrate to the sensor unit 105. As another example, a lower surface of the substrate 111 and/or the reflective layer may be disposed in a concave-convex structure to improve reflection efficiency of light.

A second electrode 143 may be disposed in a region overlapped with the light emitting structure layer 120, and may be electrically connected to the conductive layer 131 and/or a second conductivity type semiconductor layer 125. The conductive layer 131 may be formed of a reflective material to reflect incident light. The first and second sensor electrodes of the sensor unit 105 may be disposed on different planes from the second electrode 143.

FIG. 11 is a third modification example according to the first embodiment of the invention, and is an example in which a substrate 111A of a light emitting unit 101B disclosed above is a conductive material.

The conductive substrate 111A may include a semiconductor material or a silicon material. A light emitting structure layer 120 may be disposed on the substrate 111A, a conductive layer 131 may be disposed on the light emitting structure layer 120, and an insulating layer 113 may be disposed on the conductive layer 131. A sensor unit 105 may be disposed on the insulating layer 113. The sensor unit 105 includes first and second sensor electrodes 151 and 153 and a sensing material 150. The sensor unit 105 refers to the configuration disclosed in an embodiment, and may be applied selectively.

A first electrode 141 may be disposed under the substrate 111A, and the first electrode 141 may be electrically connected to the conductive substrate and a first conductivity type semiconductor layer 121. The first electrode 141 may be bonded to a circuit board and may reflect incident light. A mesa etching process for the first electrode 141 region may not be performed by growing the light emitting structure layer 120 having semiconductor layers on the substrate 111A. The sensor unit 105 may detect presence or absence of gas through a resistance change when the sensor unit 105 reacts with light emitted from the light emitting unit 101B and senses gas. A detailed configuration of the sensor unit 105 will be described with reference to the above-disclosed description.

FIG. 12 is a side cross-sectional view showing a fourth modification example of the semiconductor device having the sensor unit according to the first embodiment of the invention. In describing the fourth modification example, the same configuration as that of the above-disclosed embodiment refers to the configuration of the above embodiment, and the configuration disclosed above may be selectively included in an embodiment of the invention.

Referring to FIG. 12, a semiconductor device may include a light emitting unit 101C and a sensor unit 105 on the light emitting unit 101C. An insulating layer 113 may be disposed between the light emitting unit 101C and the sensor unit 105.

The light emitting unit 101C may include a light emitting structure layer 120, and an upper surface of the light emitting structure layer 120 may be formed with a concave-convex structure 121B. A branch electrode 141C of a first electrode 141 may extend in a partial region of the concave-convex structure 121B, but the invention is not limited thereto. The branch electrode 141C may be a transparent conductive layer or a metal material.

The sensor unit 105 is disposed on the light emitting unit 101C. The insulating layer 113 may be disposed between the light emitting unit 101C and the sensor unit 105. The insulating layer 113 may extend from an upper surface of the light emitting unit 101C toward a side surface of the light emitting structure layer 120.

The sensor unit 105 may include first and second sensor electrodes 151 and 153 and a sensing material 150 disclosed in an embodiment, and a detailed configuration refers to the configuration disclosed above. The first and second sensor electrodes 151 and 153 may include pad portions 10 and 30 and extension parts 13 and 33, and the configurations of the embodiments disclosed above may be selectively applied.

The first and second pad portions 10 and 30 of the first and second sensor electrodes 151 and 153 may be disposed on the light emitting structure layer 120. The first and second extension parts 13 and 33 connected to the first and second pad portions 10 and 30 may extend in a direction of the sensing material 150, and may be in contact with the sensing material 150. The first and second pad portions 10 and 30 may have a lower surface having a concave-convex structure. The first and second extension parts 13 and 33 may have a line pattern shape, and may have a concave-convex shape and extend along the concave-convex structure 121B of the upper surface of the light emitting structure layer 120. Since the first and second extension parts 13 and 33 in the concave-convex shape have a large surface area, a contact area with the sensing material 150 may be increased. At least one or both of the first and second sensor electrodes may be disposed to be overlapped with the branch electrode 141C in the vertical direction, thereby reducing light loss.

The light emitting unit 101C includes a first electrode 141B on the first conductivity type semiconductor layer 121 and a second electrode 143B having a plurality of conductive layers 146, 147, 148 and 149 under the second conductivity type semiconductor layer 125. A position of the first electrode 141B may be selectively applied in the above-described embodiment.

The second electrode 143B is disposed under the second conductivity semiconductor layer 125 and includes a contact layer 146, a reflective layer 147, a bonding layer 148, and a support member 149. The contact layer 146 is in contact with the semiconductor layer, for example, the second conductivity type semiconductor layer 125. The contact layer 146 may be a low conductive material such as ITO, IZO, IZTO, IAZO, IGZO, IGTO, AZO, ATO, or may be a metal of Ni or Ag. A reflective layer 147 is disposed under the contact layer 146 and the reflective layer 147 may formed of a structure including at least one layer made of a material selected from the group consisting of Ag, Ni, Al, Rh, Pd, Ir, Ru, Mg, Zn, Pt, Au, and combination thereof. The reflective layer 147 may be in contact with the second conductivity type semiconductor layer 125, but the present invention is not limited thereto.

The bonding layer 148 is disposed under the reflective layer 147 and may be a barrier metal or a bonding metal. A material of the bonding layer 148 may include, for example, at least one of Ti, Au, Sn, Ni, Cr, Ga, In, Bi, Cu, Ag, and Ta and a selected alloy thereof.

A protective layer 183 and a current blocking layer 185 are disposed between the second conductivity type semiconductor layer 125 and the second electrode. The insulating layer 113 may extend to an upper surface of an outer side of the protective layer 183. The protective layer 183 may be formed along a bottom edge of the second conductivity type semiconductor layer 125 and may be formed in a ring shape, a loop shape, or a frame shape having an open region. The protective layer 183 may include a transparent conductive material or an insulating material, for example, at least one of ITO, IZO, IZTO, IAZO, IGZO, IGTO, AZO, ATO, $SiO_2$, $SiO_x$, $SiO_xN_y$, $Si_3N_4$, $Al_2O_3$, and $TiO_2$. An inner side part of the protective layer 183 is disposed below the second conductivity type semiconductor layer 125 and an outer side part of the passivation layer 183 is located further outward than a side surface of the light emitting structure layer 120. The current blocking layer 185 may be disposed between the second conductivity type semiconductor layer 125 and the contact layer 146 or/and the reflective layer 147. The current blocking layer 185 may include at least one of $SiO_2$, $SiO_x$, $SiO_xN_y$, $Si_3N_4$, $Al_2O_3$, or $TiO_2$. As another example, the current blocking layer 185 may also be formed of a metal for Schottky contact. The current blocking layer 185 is disposed to overlap the first electrode 181 disposed on the light emitting structure layer 120 and the light emitting structure layer 120 in a thickness direction. The current blocking layer 185 may diffuse the current supplied from the second electrode 170 to another path. The current blocking layer 185 may be arranged in one or plural regions, and at least a part or all regions of the current blocking layer 185 may be overlapped with the first electrode 141B in the vertical direction.

The support member 149 is formed under the bonding layer 148 and may be formed of a conductive material such as copper-copper, gold-gold, nickel (Ni), molybdenum (Mo), copper-tungsten (Cu—W), and carrier wafers (e.g., Si, Ge, GaAs, ZnO, SiC and the like). As another example, the support member 149 may be embodied as a conductive sheet. Here, the substrate of FIG. 1 may be removed. The substrate may be removed by a physical method such as laser lift off or chemical method such as wet etching to expose the first conductivity type semiconductor layer 121. The first electrode 141B is formed on the first conductivity type semiconductor layer 121 by performing the isolation etching through the direction in which the substrate is removed.

FIG. 13 is a modification example of the sensor unit in the semiconductor device of FIG. 12. In describing such a modification example, the same configuration as that of the above-described embodiment refers to the configuration of the above embodiment, and the configuration disclosed above may be selectively included in this example.

Referring to FIG. 13, some configurations of a sensor unit 105 may be disposed on a plane different from each other. The sensor unit 105 may be disposed such that some configurations are lower or higher than other configurations. In the sensor unit 105, a part of sensor electrodes 151 and 153 may be disposed at a plane or a height different from that of a sensing material 150.

The sensor unit 105 may include the first and second sensor electrodes 151 and 153 and the sensing material 150. The first and second sensor electrodes 151 and 153 include first and second line patterns described in an embodiment, and the first and second line patterns may be disposed on a light emitting structure layer 120 in plural. The first and second line patterns may be arranged parallel to each other. Such first and second line patterns refers to the configuration and description of the embodiments disclosed above.

The first sensor electrode 151 includes a first pad portion 10 and a first extension part 13, and the second sensor electrode 153 includes a second pad portion 30 and a second extension part 33.

The first pad portion 10 may be disposed outside a first side surface S1 of the light emitting structure layer 120, and may be disposed to be overlapped with a first outer side region of a second electrode 141B in the vertical direction. The second pad portion 30 may be disposed outside a second side surface S2 of the light emitting structure layer 120, and may be disposed to be overlapped with a second outer side region of the second electrode 141B in the vertical direction. The first and second side surfaces S1 and S2 may be disposed on opposite sides of the light emitting structure layer 120. The first outer side region of the second electrode 141B may extend further outward than the first side surface S1 and the second outer side region of the second electrode 141B may extend further outward than the second side surface S2.

The first extension part 13 may extend from the first pad portion 10 to the first side surface S1 and an upper surface of the light emitting structure layer 120. The first extension part 13 connects the first pad portion 10 and the sensing material 150. The first extension part 13 may include a first connection pattern 13A connected to the first pad portion 10 on the first outer side region of the second electrode 143B, and a second connection pattern 13B disposed on the first side surface S1 of the light emitting structure layer 120 and connected to the first connection pattern 13A. The first extension part 13 and the first pad portion 10 may be connected to each other by the first and second connection patterns 13A and 13B.

The second extension part 33 may extend from the second pad portion 30 to the second side surface S2 and the upper surface of the light emitting structure layer 120. The second extension part 33 connects the second pad portion 30 and the sensing material 150. The second extension part 33 may include a third connection pattern 33A connected to the second pad portion 30 on the second outer side region of the second electrode 143B, and a fourth connection pattern 33B disposed on the first side surface S1 of the light emitting structure layer 120 and connected to the third connection pattern 33A. The second extension part 33 and the second pad portion 30 may be connected to each other by the third and fourth connection patterns 33A and 33B. At least one or both of the first and second sensor electrodes 151 and 153 may be disposed to be overlapped with the protective layer 183 in the vertical direction. A part of at least one or both of the first and second extension parts 13 and 33 may be disposed to be overlapped with the protective layer 183 in the vertical direction. The sensing material 150 is disposed in a region overlapped with the light emitting structure layer 120 in the vertical direction, and reacts with light emitted from the light emitting structure layer 120. The first and second sensor electrodes 151 and 153 may detect a change in resistance, and check the presence or absence of the sensing material 150 depending on whether the sensing material 150 reacts. In the embodiment, the first and second pad portions 10 and 30 of the first and second sensor electrodes 151 and 153 may be disposed in regions not overlapped with the light emitting structure layer 120 in the vertical direction to reduce light loss. In this case, a surface area of the sensing material 150 of the sensor unit 105 may be further increased.

When the sensor unit 105 is applied on the vertical type light emitting unit, an amount of light incident on the sensing material 150 may be maximized, and a gas contact area in the sensing material 150 may be maximized. In addition, heat dissipation efficiency may be maximized by a vertical chip structure.

FIGS. 12 and 13 show a configuration in which the sensor unit 105 is disposed on the light emitting unit having a vertical chip in an embodiment of the invention. FIG. 14 shows a configuration in which the sensor unit 105 is disposed on the light emitting unit of a flip chip structure in an embodiment of the invention.

Referring to FIG. 14, in a light emitting unit 101D, a substrate 111 is disposed on a light emitting structure layer 120. The substrate 111 may be an insulating material, a semiconductor material, or a transparent material. The substrate 111 may include a material through which light emitted from the light emitting structure layer 120 is transmitted. An upper surface of the substrate 111 may be formed with a concave-convex structure 111B.

A sensor unit 105 is disposed on the substrate 111 made of an insulating material. In this case, the insulating layer 113 shown in FIG. 3 may be removed. The sensor unit 105 may include first and second sensor electrodes 151 and 153 and a sensing material 150 disclosed in an embodiment, and a detailed configuration refers to the above-disclosed configuration. The first and second sensor electrodes 151 and 153 may include pad portions 10 and 30 and extension parts 13 and 33, and the configurations of the embodiments disclosed above may be applied selectively.

The first and second sensor electrodes 151 and 153 and the sensing material 150 may be disposed on the substrate 111. Lower surfaces of the first and second pad portions 10 and 30 of the first and second sensor electrodes 151 and 153 may be disposed along a concave-convex structure 111B of the substrate 111 as a concave-convex surface. The first and second extension parts 13 and 33 connected to the first and second pad portions 10 and 30 may extend in the direction of the sensing material 150, and may be in contact with the sensing material 150. The first and second extension parts 13 and 33 may have a line pattern shape, and may extend to have a concavo-convex shape along the concave-convex structure 111B of the upper surface of the substrate 111. Since the first and second extension parts 13 and 33 having such a concavo-convex shape have a large surface area, a contact area with the sensing material 150 may be increased.

The light emitting structure layer 120 may include a first conductivity type semiconductor layer 121, an active layer 123, and a second conductivity type semiconductor layer 125 under the substrate 111. A protective layer 133 may be disposed under the light emitting structure layer 120. The protective layer 133 may be formed of an insulating material. A first electrode 141 may be disposed under the first conductivity type semiconductor layer 121. A second electrode 143 may be disposed under the second conductivity type semiconductor layer 125, and may be electrically connected.

A conductive layer 114 may be disposed between the second conductivity type semiconductor layer 125 and the protective layer 133. The conductive layer 114 may be formed of a metal of a reflective material. The conductive layer may include at least one of a material selected from the group consisting of Ag, Ni, Al, Rh, Pd, Ir, Ru, Mg, Zn, Pt, Au, Hf, Cr, Ti, Cu, and a combination thereof. In the conductive layer 114, a transparent material layer and a reflective material layer may be stacked. The conductive layer 114 may be connected to the second electrode 143. The second electrode 143 may be disposed in one or plural.

In such a flip chip structure, the first and second electrodes 141 and 143 of the light emitting unit 101D and the first and second sensor electrodes 151 and 153 of the sensor unit 105 may be separated. The first and second electrodes 141 and 143 may be disposed under the light emitting unit 101D, and the first and second sensor electrodes 151 and 153 may be disposed over the light emitting unit 101D. The sensing material 150 may be applied to an entire region of the upper surface of the substrate 111, thereby increasing a surface area of the sensing material 150.

FIG. 15 is a side cross-sectional view showing a sixth modification example of the semiconductor device according to the first embodiment of the invention. A light emitting unit of the semiconductor device of FIG. 15 is a modification example of a flip chip structure, and a detailed description refers to the description of FIG. 14.

Referring to FIG. 15, the semiconductor device includes a light emitting unit 101E and a sensor unit 105 disposed on the light emitting unit 101E. A transparent material substrate 221 may be disposed on the uppermost layer of the light emitting unit 101E. Since the sensor unit 105 is disposed on the substrate 221, a separate insulating layer may not be provided between the light emitting unit 101E and the sensor unit 105.

The sensor unit 105 refers to the configuration disclosed in an embodiment, for example, and may include first and second sensor electrodes 151 and 153 and a sensing material 150. The first and second sensor electrodes 151 and 153 include first and second line patterns, and the first and second line patterns may be arranged in plural. The first and second line patterns may be disposed parallel with each other. The recess 226 may be disposed to be overlapped with the sensing material 150 in the vertical direction. As another example, the recess 226 may be misaligned in the vertical direction with respect to the sensing material 150, or may be disposed to overlap an outer side portion of the sensing material 150. The detailed configuration of the sensor unit 105 refers to the configuration of the above-described embodiment, and can be selectively applied to the embodiments of the invention.

The light emitting unit 101E includes a substrate 221 and a light emitting structure layer 225. The substrate 221 is disposed on the light emitting structure layer 225. The light emitting structure layer 210 is disposed on first and second electrodes 245 and 247. Each configuration of the light emitting unit 101E will be described with reference to the above-described description.

The substrate 221 may be, for example, a translucent, conductive substrate or an insulating substrate. A plurality of protrusions (not shown) may be formed on an upper surface and/or a lower surface of the substrate 221, and a side sectional surface of each of the plurality of protrusions may include a hemispherical shape, a polygonal shape, and may be arranged in a stripe form or a matrix form. The protrusions can improve a light extraction efficiency. A semiconductor layer such as a buffer layer (not shown) may be disposed between the substrate 221 and the first conductivity type semiconductor layer 222, but the present invention is not limited thereto. The substrate 221 may be removed, but is not limited thereto.

The light emitting structure layer 225 includes a first conductivity type semiconductor layer 222, a second conductivity type semiconductor layer 224 and an active layer 223 between the first and second conductivity semiconductor layers 222 and 224. Other semiconductor layers may be disposed above and/or under the active layer 223, but the present invention is not limited thereto. Such the light emitting structure layer 225 will be described with reference to the description of the embodiments disclosed above.

The first and second electrodes 245 and 247 may be disposed under the light emitting structure layer 225. The first electrode 245 is in contact with and electrically connected to the first conductivity type semiconductor layer 222, and the second electrode 247 is in contact with and electrically connected to the second conductivity type semiconductor layer 224. The first electrode 245 and the second electrode 247 may be made of a metal having properties of an ohmic contact, an adhesive layer, and a bonding layer, and may not be transparent. The first and second electrodes 245 and 247 may have a polygonal or circular bottom shape.

The light emitting unit 101E includes first and second electrode layers 241 and 242, a third electrode layer 243, and dielectric layers 231 and 233. Each of the first and second electrode layers 241 and 242 may be formed as a single layer or a multilayer, and may function as a current diffusion layer. The first and second electrode layers 241 and 242 include a first electrode layer 241 disposed under the light emitting structure layer 225, and the second electrode layer 242 disposed under the first electrode layer 241. The first electrode layer 241 diffuses a current, and the second electrode layer 242 reflects incident light. Here, the recess 226 exposes a part of the light emitting structure layer 225 through the first and second electrode layers 241 and 242. A portion of the light emitting structure layer 225 may be a region of the first conductivity type semiconductor layer 222.

The first and second electrode layers 241 and 242 may be formed of different materials. The first electrode layer 241 may be formed of a light-transmitting material, for example, a metal oxide or a metal nitride. The first electrode layer 241 may be selectively formed of, for example, indium tin oxide (ITO), ITO nitride, indium zinc oxide (IZO), indium zinc oxide (IZO), Indium gallium zinc oxide (IGZO), indium gallium tin oxide (IGTO), aluminum zinc oxide (AZO), antimony tin oxide (ATO) and gallium zinc oxide (GZO). The second electrode layer 242 may contact the lower surface of the first electrode layer 241 and function as a reflective electrode layer. The second electrode layer 242 includes a metal such as Ag, Au, or Al. The second electrode layer 242 may partially contact the lower surface of the second conductivity type semiconductor layer 224 when a portion of the first electrode layer 241 is removed. As another example, structures of the first and second electrode layers 241 and 242 may be stacked in an Omni Directional Reflector layer (ODR) structure. The ODR structure may have a stacked structure of a first electrode layer 241 having a low refractive index and a second electrode layer 242 having a highly reflective metal material and contacted with the first electrode layer 241. The electrode layers 241 and 242 may have a laminated structure of, for example, ITO/Ag. A total reflection angle at an interface between the first electrode layer 241 and the second electrode layer 242 may be improved.

As another example, the second electrode layer 242 may be removed and formed of a reflective layer of another material. The reflective layer may be formed of a distributed Bragg reflector (DBR) structure. The distributed Bragg reflector structure includes a structure in which two dielectric layers having different refractive indices are alternately arranged. For example, the two dielectric layers may include different layers selected from a $SiO_2$ layer, a $Si_3N_4$ layer, a $TiO_2$ layer, an $Al_2O_3$ layer, and a MgO layer.

As another example, the electrode layers 241 and 242 may include both a dispersed Bragg reflection structure and an ODR structure. In this case, a light emitting chip having a light reflectance of 98% or more may be provided. Since the light emitted from the second electrode layer 242 is emitted through the substrate 311, the light emitting chip mounted in the flip-type can emit most of the light in the vertical direction. The third electrode layer 243 is disposed under the second electrode layer 242 and is electrically insulated from the first and second electrode layers 241 and 242.

The third electrode layer 243 may be formed of a metal such as titanium (Ti), copper (Cu), nickel (Ni), gold (Au), chromium (Cr), tantalum (Ta), platinum (Pt), tin (Sn), Silver (Ag), and phosphorus (P). The first electrode 245 and the second electrode 247 are disposed under the third electrode layer 243.

The dielectric layers 231 and 233 prevent unnecessary contact among the first and second electrode layers 241 and 242, the third electrode layer 243, the first and second electrodes 245 and 247, and the light emitting structure layer 225. The dielectric layers 231 and 233 include first and second dielectric layers 231 and 233. The first dielectric layer 231 is disposed between the third electrode layer 243 and the second electrode layer 242. The second dielectric layer 233 is disposed between the third electrode layer 243 and the first and second electrodes 245 and 247.

The third electrode layer 243 is connected to the first conductive semiconductor layer 222. The connection portion 244 of the third electrode layer 243 protrudes from the first and second electrode layers 241 and 242 and the recess 226 of the light emitting structure layer 225 and is electrically connected to the first conductivity semiconductor layer 222. Here, the recess 226 may have a gradually narrower width as it is adjacent to the substrate 221. The recess 226 may provide a sloped surface. A plurality of the recesses 226 may be disposed apart from each other. The connection portion 244 may be disposed in each of the recesses 226. The recesses 226 may extend through the second conductivity type semiconductor layer 224 and the active layer 223 to a portion of the first conductivity type semiconductor layer 222. A portion 232 of the first dielectric layer 231 extends around the connection portion 244 of the third electrode layer 243 to form the third electrode layer 243 and the first and second electrode layers 241 and 242, and an electrical connection between the conductive semiconductor layer 224 and the active layer 223 blocks. An insulating layer may be disposed on the side surface of the light emitting structure layer 225 for lateral protection, but the present invention is not limited thereto.

The second electrode 247 is disposed under the second dielectric layer 233 and contacts or is electrically connected to at least one of the first and second electrode layers 241 and 242 through open regions of the first dielectric layer 231 and the second dielectric layer 233. The first electrode 245 is disposed under the second dielectric layer 233 and is connected to the third electrode layer 243 through an open region of the second dielectric layer 233. The protrusion 248 of the second electrode 247 is electrically connected to the second conductivity type semiconductor layer 224 through the first and second electrode layers 241 and 242 and the protrusion 246 of the first electrode 245 and is electrically connected to the first conductivity type semiconductor layer 222 through the third electrode layer 243.

A plurality of connection portions 246 connected to the first electrode 245 may be disposed to improve current diffusion. The first and second electrodes 245 and 247 may be provided under the light emitting structure layer 225 in a large area. The lower surfaces of the first and second electrodes 245 and 247 may be provided on the same horizontal surface in a larger area, so that the bonding area with the bonding member can be improved. Accordingly, the efficiency of bonding the first and second electrodes 245 and 247 to the joining member may be improved.

FIG. 16 is a first modification example of the semiconductor device of FIG. 15.

Referring to FIG. 16, the semiconductor device has a sensor unit 105 disposed on a light emitting unit 101E. The light emitting unit 101E may be provided with a concave portion 261B at an upper portion thereof, and at least a part of the sensor unit 105 may be disposed in the concave portion 261B. The concave portion 261B may be disposed in a central region of the light emitting unit 101E. The central region may be a region spaced apart from edges of the upper surface of the light emitting unit 101E.

A depth T2 of the concave portion 261B may be formed in a depth of 1/10 or more of a thickness of the light emitting unit 101E, for example, in a depth of 1/10 or more to 8/10. The depth T2 of the concave portion 261B shows a depth in the Z-axis direction on an upper surface of the substrate 221. The depth T2 of the concave portion 261B may be disposed to be equal to or smaller than a thickness of the sensing material 150 to improve incidence efficiency of light through a surface of the sensing material 150. When the depth T2 of the concave portion 261B is deeper than the thickness of the sensing material 150, a gas sensing function on the surface of the sensing material 150 may be deteriorated. A side surface 261A of the concave portion 261B may include an inclined surface or a curved surface, but the invention is not limited thereto.

FIG. 17 is a second modification example of the semiconductor device of FIG. 15.

Referring to FIG. 17, the semiconductor device has a sensor unit 105 disposed on a light emitting unit 101E. The light emitting unit 101E may be provided with recesses 271A and 271B at an upper portion thereof, and at least a part of the sensor unit 105 may be disposed at the recesses 271A and 271B. The recesses 271A and 271B may include at least one or both of a first recess 271A adjacent to a first side S1 of the light emitting unit 101E and a second recess 271B adjacent to a second side S2.

A part of a first sensor electrode 151 of the sensor unit 105 may be disposed at the first recess 271A, and a part of a second sensor electrode 153 of the sensor unit 105 may be disposed at the second recess 271B. A first pad portion 10 of the first sensor electrode 151 is disposed at the first recess 271A, and a first extension part 13 extends in a direction of a sensing material 150. A second pad portion 30 of the second sensor electrode 153 is disposed at the second recess 271B, and a second extension part 33 extends in the direction of the sensing material 150. The first and second recesses 271A and 271B may be disposed at an upper portion of a substrate 221, respectively.

A central region of the substrate 221 of the light emitting unit 101E may protrude upward therefrom, and the first and second recesses 271A and 271B may be disposed in regions opposite to each other. An upper surface of the central region of the substrate 221 of the light emitting unit 101E may be disposed higher than lower surfaces of the first and second pad portions 10 and 30. The sensing material 150 of the light emitting unit 101E may be disposed on the upper surface of the central region of the substrate 221 of the light emitting unit 101E. The central region of the substrate 221 may have a gradually wider width as approaching the sensing material 150. Accordingly, circumferential surfaces S3 and S4 of the central region of the substrate 221 may provide inclined surfaces, and thus it is possible to reflect or emit light in another direction.

The sensing material 150 may be disposed on the central region of the substrate 221. The central region may be a region spaced apart from each side surface of the substrate 221. A depth T3 of the recesses 271A and 271B may be 70% or less of a thickness of the substrate 221. When the depth T3 of the recesses 271A and 271B exceeds 70%, a problem in processing and a problem that the first and second extension parts 13 and 33 of the first and second sensor electrodes 151 and 153 may be cut may occur, and thus electrical reliability may be deteriorated. Since the first and second pad portions 10 and 30 of the first and second sensor electrodes 151 and 153 are disposed at the recesses 271A and 271B, the depth T3 is lowered and a height of a wire is lowered, and thus external impact transmitted to the wire may be reduced.

FIG. 18 is a side cross-sectional view of a sensing device having a semiconductor device according to an embodiment. In description of FIG. 18, the above-disclosed configuration refers to the above description, and may be selectively applied in this example. The semiconductor device of the sensing device of FIG. 18 will be described as an example of the semiconductor device of FIG. 15.

Referring to FIG. 18, a gas sensing device may include a circuit board 550, a semiconductor device having a light emitting unit 101E and a sensor unit 105 on the circuit board 550, a package body 560 around the semiconductor device, and a reflective plate 570 disposed on the semiconductor device and disposed on the package body 560.

The circuit board 550 may include at least one of a resin PCB, a metal core PCB (MCPCB), and a flexible PCB (FPCB), but the invention is not limited thereto. The circuit board 550 may include a ceramic material.

The circuit board 550 may include a plurality of electrode patterns 551, 552, 553 and 554 on an upper surface thereof, and the plurality of electrode patterns 551, 552, 553 and 554 may be electrically connected to the sensor unit 105 and the light emitting unit 101E. For example, first and second electrodes 245 and 247 of the light emitting unit 101E may be bonded to the first and second electrode patterns 551 and 552 disposed under the light emitting unit 101E with a bonding member. First and second pad portions 10 and 30 of the sensor unit 105 may be connected to the third and fourth electrode patterns 553 and 354 with wires 555 and 556.

The light emitting unit 101E may be disposed between the sensor unit 105 and the circuit board 550.

The package body 560 may be a ceramic material. The package body 560 may be formed of the same ceramic material as a material of a body of the circuit board 550. Such a ceramic material may effectively reflect light emitted from the light emitting unit 101E.

An inside of the package body 560 has a cavity 565 or a recessed structure, and the sensor unit 105 and the light emitting unit 101E may be disposed therein. A reflective plate 570 is disposed on the package body 560, and the reflective plate 570 may reflect light to prevent leakage of light. A stepped structure may be disposed around an upper portion of the package body 560, and the reflective plate 570 may be closely coupled on the stepped structure. The reflective plate 570 may be in contact with the package body 560 with an adhesive (not shown). The sensor unit 105 may sense a gas exposing by light emitted from the light emitting unit 101E and gas G2 introduced through an opening part 572 of the reflective plate 570, for example, a harmful gas.

The light emitting unit 101E and the sensor unit 105 are overlapped on the circuit board 550, and a configuration of another embodiment disclosed above may be applied selectively.

In an embodiment, any one of first and second sensor electrodes of the sensor unit may be commonly connected to the light emitting unit, for example, the first sensor electrode and a first electrode may be connected in common, but the invention is not limited thereto.

According to an embodiment of the invention, an active layer of the light emitting unit may be overlapped with first and second regions of the sensing material in the vertical direction. The sensing material may have conductivity by light emitted from the active layer. The second region of the sensing material may be disposed between the first extension part and the second extension part. The first extension part may be a plurality and the second extension part may be a plurality, and each of the second extension parts may be disposed between the first extension parts, respectively. The light emitting unit includes a first electrode connected to the first conductivity type semiconductor layer and a second electrode connected to the second conductivity type semiconductor layer, and the first and second sensor electrodes may be electrically separated from the first and second electrodes. At least one of the first and second electrodes may include a region overlapped with at least one of the first extension part and the second extension part in a vertical direction. An insulating layer may be included between the light emitting unit and the sensor unit. A conductive layer may be included between the insulating layer and the light emitting structure layer. First and second extension parts of the sensor unit may be disposed between the sensing material and the second conductivity type semiconductor layer, and the second conductivity type semiconductor layer may be disposed between the sensor unit and the active layer. The sensor unit may be disposed on the first conductivity type semiconductor layer, and the insulating layer may be disposed between the first conductivity type semiconductor layer and the sensor unit.

According to an embodiment of the invention, in the light emitting structure layer, the active layer and the first conductivity type semiconductor layer are disposed on the second conductivity type semiconductor layer, and the light emitting unit may include a recess passing through the second conductivity type semiconductor layer and the active layer and disposed to a partial region of the first conductivity type semiconductor layer, and at least a part of the sensing material may be vertically overlapped with the recess. The light emitting unit includes a transparent material substrate between the light emitting structure layer and the sensor unit, and the sensing material may be overlapped with the transparent material substrate in a vertical direction. It is possible to include a second electrode having a reflective layer under the light emitting structure layer and a protective layer disposed on an outer circumference between the light emitting structure layer and the second electrode, and the protective layer may be vertically overlapped with at least one of the first sensor electrode and the second sensor electrode. The substrate may be included under the light emitting structure layer, and the substrate may include a conductive or insulating material.

The first conductivity type semiconductor layer of the light emitting structure layer may have a concave-convex structure on a surface of a region corresponding to the gas sensor unit.

According to an embodiment of the invention, at least one of the first and second electrodes may include a region overlapped with at least one of the first extension part and the second extension part in the vertical direction. According to an embodiment of the invention, the light emitting unit may include an insulating or metallic reflective layer under thereof. An upper surface of the light emitting unit is formed in a concave-convex structure, and lower surfaces of the first and second extension parts of the first and second sensor electrodes are disposed to correspond to the upper surface of the concave-convex structure, and the first and second sensor electrodes may be vertically overlapped with a region of the concave-convex structure of the light emitting unit.

According to an embodiment of the invention, the light emitting unit may include a second electrode having a reflective layer under the light emitting structure layer, and the extension part of the first and second sensor electrodes may be vertically overlapped with the second electrode.

According to an embodiment of the invention, the first extension part may include a plurality of first line patterns extending in a direction of the sensing material, and the second extension part may include a plurality of second line patterns extending in a direction adjacent to the first line pattern, and the second line pattern may be disposed at a predetermined interval between the plurality of first line patterns, and the sensing material may contact between the first and second line patterns, and may be disposed to be overlapped with the light emitting structure layer in the vertical direction.

According to an embodiment of the invention, the extending directions of the first and second line patterns may be disposed in a direction orthogonal to a virtual straight line connecting the first and second electrodes.

According to an embodiment of the invention, the second electrode may include a plurality of branch electrodes extending in a direction of the first electrode, and at least one of the branch electrodes may be disposed to be overlapped with at least one of the first and second line patterns in the vertical direction.

Exemplary Embodiment 2

Figure 20:
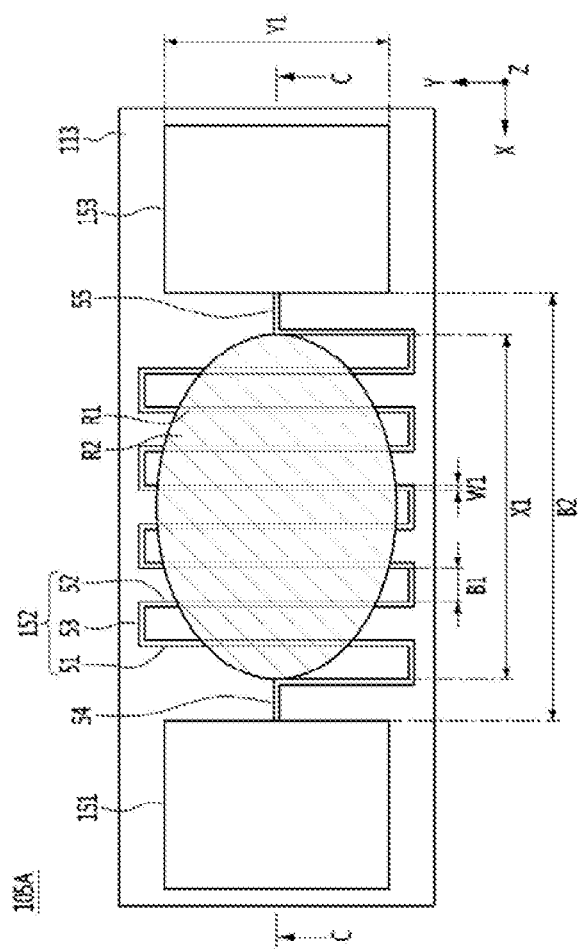
FIG. 20 is a plan view of a semiconductor device according to a second embodiment of the invention.
Figure 21:
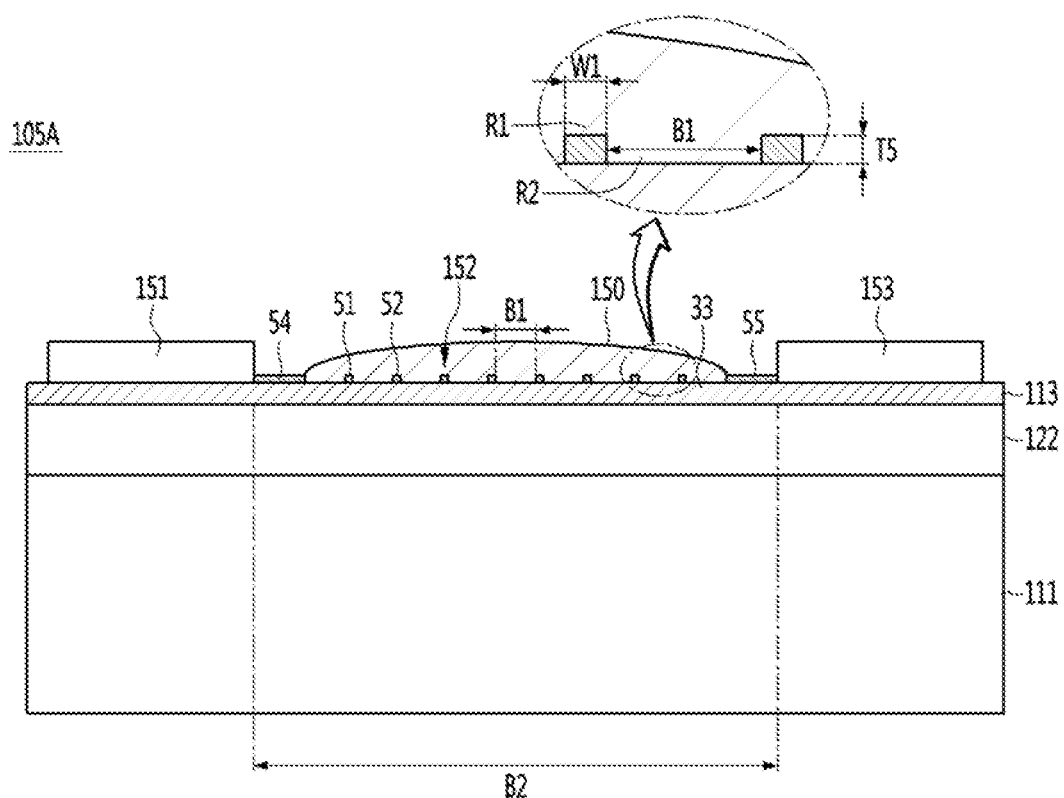
FIG. 21 is a C-C sectional view of the semiconductor device of FIG. 1.

FIG. 20 is a plan view of a semiconductor device according to a second embodiment of the invention, and FIG. 21 is a cross-sectional view of the semiconductor device taken along a line C-C of FIG. 20.

Referring to FIGS. 20 and 21, the semiconductor device may include a sensor unit 105A. The sensor unit 105A may include sensor electrodes 151 and 153, an electrode portion 152 connected to the sensor electrodes 151 and 153, and a sensing material 150 disposed on the electrode portion 152. The sensing material 150 and the electrode portion 152 may be disposed on an insulating layer 113. The insulating layer 113 may be disposed on at least one of a substrate 111 and a semiconductor layer.

The substrate 111 may be a conductive or insulating material. The substrate 111 may be a semiconductor substrate or a non-semiconductor substrate. The substrate 111 may be a light-transmitting or non-light-transmitting substrate. The substrate 111 may be selected from the group consisting of a sapphire substrate ($Al_2O_3$), GaN, SiC, ZnO, Si, GaP, InP, $Ga_2O_3$, GaAs, and the like. The substrate 11 may be formed of a GaN-based semiconductor, for example, a GaN semiconductor. The substrate 111 may be a bulk GaN single crystal substrate. The substrate 111 may be used as a support member for supporting the sensor unit 105A.

A thickness of the substrate 111 may be in a range of 30 μm or more, for example, 30 μm to 3000 μm. When the thickness of the substrate 111 is smaller than that of the above range, handling during manufacture may be difficult, and when the thickness of the substrate 111 is larger than that of the above range, a size of the sensor unit 105A may be increased. In the substrate 111, a length in a first axis X direction and a length in a second axis Y direction may be the same or different. For example, the length of the substrate 111 in the X-axis direction may be greater than that in the Y-axis direction. The sensor unit 105A may be provided by removing the substrate 111 or may be provided without the substrate.

As another example, the substrate 111 may be a circuit board. When the substrate 111 is a circuit board having a circuit pattern, at least one or both of the semiconductor layer and the insulating layer 113 may be removed. The circuit board may include at least one of a resin PCB, a metal core PCB (MCPCB), and a flexible PCB (FPCB), but the invention is not limited thereto. The circuit board may include a ceramic material.

The semiconductor layer 122 may be disposed of a compound semiconductor of Group II to VI elements. The semiconductor layer 122 may include at least one of Group II-VI compound semiconductors and Group III-V compound semiconductors.

When the semiconductor layer 122 is conductive, the insulating layer 113 may be disposed between the semiconductor layer and the sensor electrodes 151 and 153 and the electrode portion 152. When the semiconductor layer is insulating, the insulating layer 113 may be removed or provided thinner. When the semiconductor layer 122 is conductive, it may be an n-type semiconductor layer having an n-type dopant, or a p-type semiconductor layer having a p-type dopant.

The semiconductor layer 122 may be formed of at least one of GaN, AlN, AlGaN, InGaN, InN, InAlGaN, AlInN, AlGaAs, GaP, GaAs, GaAsP, AlGaInP, and ZnO. The semiconductor layer 122 may include a compositional formula of $In_xAl_yGa_{1-x-y}N$ (0≤x≤1, 0≤y≤1, 0≤x+y≤1). The semiconductor layer 122 may be a single layer or multiple layers, and may include a semiconductor layer different from each other in case of the multiple layers.

A buffer layer (not shown) may be disposed between the semiconductor layer 122 and the substrate 111. The buffer layer may be disposed of a compound semiconductor of Group II to VI elements. The buffer layer may include at least one of Group II-VI compound semiconductors and Group III-V compound semiconductors. The buffer layer may be formed of at least one of GaN, AlN, AlGaN, InGaN, InN, InAlGaN, AlInN, AlGaAs, GaP, GaAs, GaAsP, AlGaInP and ZnO. The semiconductor layer 122 may include a compositional formula of $In_xAl_yGa_{1-x-y}N$ (0≤x≤1, 0≤y≤1, 0≤x+y≤1). The buffer layer may be a doped semiconductor or an unintentional doped semiconductor.

The semiconductor layer 122 may be a light emitting structure layer, for example, and may include at least one or both of a first conductivity type semiconductor layer, an active layer, and a second conductivity type semiconductor layer. The first conductivity type semiconductor layer may include an n-type semiconductor layer disposed on the substrate 111 and the second conductivity type semiconductor layer may include a p-type semiconductor layer on the active layer. As another example, the first conductivity type semiconductor layer may include a p-type semiconductor layer and the second conductivity type semiconductor layer may include an n-type semiconductor layer. The active layer may selectively emit light within a wavelength range from ultraviolet light to visible light or infrared light, for example, and may emit light having a peak wavelength of ultraviolet light or light having a peak wavelength of blue, but the invention is not limited thereto.

The insulating layer 113 may be an insulating sheet or a layer, but is not limited thereto. The insulating layer 113 may include, for example, a nitride or an oxide-based insulating material, and may be, for example, formed of at least one of $Si_xN_y$ (x>0, y>0) including at least one of $SiN_2$, $SiN_4$ and $Si_3N_4$, $SiO_x$ (x>0) including $SiO_2$, $SiO_xN_y$ (x>0, y>0) including $SiO_3N_4$, and $Al_xO_y$ (x>0, y>0) including $Al_2O_3$. When the insulating layer 113 is $Si_xN_y$, it may be formed using the same equipment used to form the semiconductor layer 122. As another example, the insulating layer 113 may be formed as a single layer or multiple layers. A thickness of the insulating layer 113 may be formed to be thinner than that of the substrate 111. The thickness of the insulating layer 113 may be thinner or thicker than that of the semiconductor layer 122. The thickness of the insulating layer 113 may be in a range of 200 nm or more, for example, 500 nm to 10000 nm. When the thickness of the insulating layer 113 is less than the above range, electrical interference may occur, and when the thickness of the insulating layer 113 exceeds the above range, the stress between the insulating layer 113 and the semiconductor layer 122 becomes too large, and thus reliability of the sensor may be lowered, or when the semiconductor layer 122 is a light emitting structure layer, a wavelength of light emitted from the semiconductor layer may be different from a designed wavelength.

The sensing material 150, the sensor electrodes 151 and 153, and the electrode portion 152 may be disposed on an upper surface of the insulating layer 113. The insulating layer 113 may be overlapped with the sensing material 150 and the electrode portion 152 in the z-axis direction. The insulating layer 113 on the sensor unit 105A may be removed. A removal process of the insulating layer 113 may be performed after forming the sensing material 150.

In an embodiment, the sensor unit 150, the sensor electrodes 151 and 153, and the electrode portion 152 may be defined as a sensor unit. The sensor unit 105A of the embodiment may further include the insulating layer 113. The sensor unit 105A may include at least one of a substrate 111 and a semiconductor layer 122 as a support member under the insulating layer 113.

The sensing material 150 may include a material that is activated at a predetermined wavelength. The sensing material 150 may be activated by light emitted from a light emitting unit. Here, the activation may include a change in resistance of the sensing material 150. The sensing material 150 may be disposed in a direction in which light emitted from the light emitting unit travels, or may be disposed on a path directly irradiated with light or a path indirectly irradiated.

The sensing material 150 may be disposed between the first and second sensor electrodes 151 and 153, and may be disposed on the electrode portion 152. The sensing material 150 may be disposed in a region between patterns of the electrode portion 152, and may be in contact with surfaces of the patterns. The sensing material 150 may be activated by the irradiated light to change a resistance of the electrode portion 152.

As shown in FIG. 21, the sensing material 150 may include a plurality of first regions R1 overlapped with different regions of the electrode portion 152 in the vertical direction and a second region R2 not overlapped with the electrode portion 152. The second region R2 of the sensing material 150 may be a region protruding toward a substrate 111 or a bottom direction between the plurality of first regions R1. Resistance of the sensing material 150 may be changed by light. The sensing material 150 may have its resistance lowered by incident light or may have conductivity. The sensing material 150 may be disposed on the electrode portion 152. The second region R2 may be disposed between neighboring patterns of the electrode portion 152. The first and second regions R1 and R2 may have a predetermined length and may be disposed alternately. A portion of the second region R2 may be the same width as an interval B1 between the patterns of the electrode portions 152. The second region R2 may extend in one direction with a long length, and an extension direction of the second region R2 may be disposed parallel to the extension direction of the pattern of the electrode portion 152. The interval B1 between the first electrode portions 152 may be in a range of 50 μm or more, for example, 50 μm to 500 μm. A resistance value for measuring gas may be determined according to the interval B1 between the electrode portions 152. As the interval B1 between the electrode portions 152 is closer, the resistance value of the sensing material 150 may be lower. Accordingly, the neighboring patterns of the electrode portion 152 may be electrically connected.

The sensing material 150 may be in contact with the electrode portion 152 in a region between the patterns of the electrode portion 152. Since the sensing material 150 has a low resistance or conductivity due to incident light, it is possible to electrically connect the patterns of the adjacent electrode portions 152. The sensing material 150 may have a first resistance due to incident light, and may be changed to a second resistance lower than the first resistance when an external gas is introduced. Accordingly, the sensing material 150 may reduce the electrical resistance between the patterns of the electrode portion 152 by light and gas, and it is possible to electrically connect the patterns of the electrode portion 152 through the second region R2. The electrode portion 152 is electrically connected by the sensing material 150, and the resistance between the electrode portions 152 is lowered so that the resistance may be detected by the first and second pad portions 151 and 152. A change in the detected resistance may measure the presence or absence of gas by the semiconductor device.

The sensing material 150 may be formed of a metal oxide material. The sensing material 150 may include a main sensing material and a catalyst. The main sensing material may include a metal oxide material, and the catalyst may include a metal. The main sensing material may include at least one or more of $SnO_2$, CuO, $TiO_2$, $In_2O_3$, ZnO, $V_2O_5$, $RuO_2$, $WO_3$, $ZrO_2$, $MoO_3$, NiO, CoO, $Fe_2O_3$, and $AB_2O_4$, and may be formed of various materials which are not limited thereto. For example, the catalyst of the sensing material 150 may include at least one or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), ruthenium (Ru), rhodium (Rh), silver (Ag), hafnium (Hf), tantalum (Ta), tungsten (W), rhenium (Re), and iridium (Ir). The catalyst material may be mixed with the main sensing material as a doping material in the sensing material 150. The sensing material 150 may include materials that may have both sensing and catalytic properties. The material of the sensing material 150 according to an embodiment may be selectively mixed in the main sensing material and the catalyst according to the type of gas to be sensed.

The sensing material 150 may contain grains and may be the same or different size. The size of the grain may be in the range of 2 nm to 20 nm, for example, when the grain is less than 2 nm, a role of the sensing material 150 may be insignificant, and when the grain is greater than the range, a sensitivity of the sensing may be reduced.

In the sensing material 150, one or more kinds of main sensing materials may be mixed, and the mixed material may be doped with one or two kinds of catalyst materials. The main sensing material may be in a range of 25 mol % to 75 mol % by a mixture of one or two kinds, and may be set to a range capable of responding to a specific gas and a gas sensing property. The catalyst material may be added at 5 wt % or less of the main sensing material, for example, in a range of 1 wt % to 5 wt %, and the gas sensing sensitivity may be lowered when the catalyst material exceeds the above range. For example, when $SnO_2$ and ZnO are mixed, in the sensing material 150, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt % to 3 wt % of the main sensing material.

A shape of the bottom surface of the sensing material 150 may be a circular shape, an elliptical shape, or a polygonal shape, or may be a polygonal shape in which a corner portion is a curve. A width X1 or Y1 in any one of a first direction or a second direction of the sensing material 150 may be 3 mm or less. For example, when an outer shape of the sensing material 150 is a circular or an elliptical shape, a diameter may be 3 m or less. A bottom area of the sensing material 150 may be 10 $mm^2$ or less. The width X1 or Y1 in any one direction of the sensing material 150 may range from 0.5 mm to 3 mm. When the width is smaller than the above range, a change in resistance is insignificant, and when the width is larger than the above range, an improvement in sensing sensitivity may be insignificant. The sensing material 150 may be disposed in a central region of the electrode portion 152, or may cover the electrode portion 152 with a length longer than one direction of a line pattern of the electrode portion 152. The maximum thickness of the sensing material 150 may be more than a thickness of the electrode portion 152. When the maximum thickness of the sensing material 150 is smaller than the thickness of the electrode portion 152, the sensing sensitivity of the sensing material 150 may be insignificant.

The sensing material 150 may be in contact with the surface of the electrode portion 152 to change the resistance. Here, as shown in FIG. 34, as compared with a comparative example, it can be seen that resistance of a sensing device of an embodiment decreases as a gas sensing time passes. Such resistance change may be detected to check the presence or absence of gas.

An electrode structure of the sensor unit 105A in the second embodiment of the invention may include a pattern structure capable of contacting the sensing material 150 and detecting a change in resistance from the sensing material 150. The electrode structure may include a plurality of sensor electrodes 151 and 153 and an electrode portion 152 connected to the plurality of sensor electrodes 151 and 153.

The plurality of sensor electrodes 151 and 153 are pads for bonding wires, and may be formed as a single layer or multiple layers by using a metal material, for example, at least one of Au, Pt, Pd, Al, Mo, Ag, Ti, Tn, W, Ru, Ir, and Cu, an alloy thereof, or different materials.

The plurality of sensor electrodes 151 and 153 include first and second sensor electrodes 151 and 153, which may be spaced apart from each other. The first and second sensor electrodes 151 and 153 may be disposed on both sides of the sensing material 150 or on any one side of the sensing material 150. The first and second sensor electrodes 151 and 153 may be disposed on opposite sides with respect to the sensing material 150. Thicknesses of the first and second sensor electrodes 151 and 153 may be thicker than the thickness of the electrode portion 152, and external impact may be alleviated when bonding the wire. The first and second sensor electrodes 151 and 153 may be electrically connected to each other.

A top view shape of the first pad portion 151 may include at least one of a circular shape, an elliptical shape, a polygonal shape, and a hemispherical shape. The second pad portion 153 may have the same shape as the first pad portion or may have a different shape, and may include at least one of a shape, an ellipse shape, a polygonal shape, and a hemispherical shape.

The electrode portion 152 is a conducting wire connected to the plurality of sensor electrodes 151 and 153. The electrode portion 152 may be formed of as a single layer or multiple layers by using at least one of gold (Au), platinum (Pt), tungsten (W), zinc (Zn), cobalt (Co), palladium (Pd), aluminum (Al), molybdenum (Mo), silver (Ag), titanium (Ti), tin (Sn), zirconium (Zr), magnesium (Mg), iron (Fe), titan nitride (TiN), nichrome (Nb—Cr alloy), rubidium (Rb), thorium (Th), platinum-rhodium (Pt—Rh), copper (Cu), strontium (Sr), thallium (T1), chrome (Cr), ruthenium (Ru), iridium (Ir), nickel (Ni), chromel (Ni—Cr), mercury (Hg), and alumel (Ni—Al), an alloy thereof, or different materials. Since the electrode portion 152 is exposed to the outside, an oxidation prevention layer may be included. The electrode portion 152 may include a material having a high resistivity, for example, a resistivity of 20 or more. The Nichrome may have a resistivity of 108.3.

The electrode portion 152 may be connected between the plurality of sensor electrodes 151 and 153, for example, the first and second sensor electrodes 151 and 153. The electrode portions 152 may be disposed, for example, as an extended electrode connected in series. The extended electrode may include a linear shape, a curved shape, a bent shape, and a line shape extending in different directions. The electrode portion 152 may include a plurality of line patterns 51 and 52 parallel to each other in the first direction and a connection pattern 53 connecting one end or the other end of the plurality of line patterns 51 and 52. The line patterns 51 and 52 may be defined as first and second line patterns 51 and 52 spaced apart from a predetermined interval B1. The line patterns 51 and 52 may be arranged in parallel or non-parallel to each other. The first and second sensor electrodes 151 and 153 may be connected to each other by the electrode pattern 152 by connecting different ends of the first and second line patterns 51 and 52 to the connection patterns 53. The electrode portion 152 may be formed in a continuous line pattern between the first and second sensor electrodes 151 and 153. The electrode portion 152 may be arranged in a single continuous line connected to the first and second sensor electrodes 151 and 153. The electrode portions 152 may be arranged so as to overlap each other on a horizontal plane between the first and second sensor electrodes 151 and 153, for example, in the X-axis direction or the Y-axis direction.

A width W1 of the electrode portion 152 may be at least 2 μm or more, for example, in a range of 2 μm to 5 μm. When the width W1 is smaller than the above range, discrimination of resistance may be deteriorated, and when the width W1 is larger than the above range, an improvement in sensitivity to a change in the resistance may be insignificant. A thickness T5 of the electrode portion 152 may be 5 nm or more, for example, in a range of 5 nm to 1000 nm. The thickness T5 of the electrode portion 152 may be smaller than the width W1 of the electrode portion 152, and is not limited thereto.

The interval B1 between the line patterns 51 and 52 of the electrode portion 152 may be larger than the width W1 of the line patterns 51 and 52. The interval B1 between the line patterns 51 and 52 may be five times or more the width W1 of the line patterns 51 and 52. The interval B1 between the line patterns 51 and 52 of the electrode portion 152 may be 50 μm or more, for example, in a range of 50 μm to 500 μm. When the interval B1 is less than the above range, sensing sensitivity is lowered, and when the interval B1 is larger than the above range, a reaction rate may be lowered or eliminated. The interval B1 between the line patterns 51 and 52 of the electrode portion 152 may affect the sensing sensitivity according to the sensing material 150.

An entire length of the electrode portion 152 may be determined according to a length of the first and second line patterns 51 and 52 and a number of times the first and second line patterns 51 and 52 are repeated. The number of times the line patterns 51 and 52 are bent may be four times or more. The number of times of bending is a case in which the portion bent from the first line pattern 51 to the connection pattern 53 and the portion bent from the connecting pattern 53 to the second line pattern 52 is one circuit.

The electrode portion 152 may detect whether gas is sensed through initial resistance applied to both ends of the electrode portion 152 and a change in a sensing resistance changed by the sensor unit 150. In order to provide such initial resistance, the electrode portion 152 may be provided with a predetermined length or more. To this end, the entire length of the electrode portion 152 may be determined according to the length of the first and second line patterns 51 and 52 and the interval B1 between the first and second line patterns 51 and 52. The entire length of the electrode portion 152 may be 150 μm or more, for example, in a range of 150 μm to 15000 μm, as an entire length. The distance B2 between the first and second sensor electrodes 151 and 153 may be 100 μm or more, for example, in the range of 100 μm to 12,000 μm. The distance B2 between the first and second sensor electrodes 151 and 153 may be smaller than the entire length of the electrode portion 152. The width X1 in the X-axis direction of the sensing material 150 may be 50% or more of the distance B2 between the first and second sensor electrodes 151 and 153.

Electrical resistance applied to both ends of the electrode portion 152 may be obtained by (resistivity×length of material)/cross-sectional area. The resistance applied to both ends of the electrode portion 152 may be in the range of 1 Mohm to 10 Mohm, and when it is out of the range, it may be out of a detection range of an integrated circuit (ASIC). The resistance of the electrode portion 152 may be changed depending on the thickness T5, the width W1, and the length of the line patterns 51 and 52. For example, when a material of the electrode portion 152 is Nichrome, the width of the line pattern of the electrode portion 152 is 5 μm, and the entire length is 5 cm, the resistance of both ends of the electrode portion 152 may be implemented as 4 Mohm.

A first end portion 54 of the electrode portion 152 may be connected to the first pad portion 151 and a second end portion 55 may be connected to the second pad portion 153. The first end portion 54 may extend from the first pad portion 151 toward the line patterns 51 and 52, and the second end portion 55 may extend from the second pad portion 153 toward the line patterns 51 and 52. The extending direction of the first and second line patterns 51 and 52 of the electrode portion 152 may be the Y-axis direction, and may be a direction orthogonal to the linear direction X connecting the first and second sensor electrodes 151 and 153. The first and second end portions 54 and 55 may extend in the X-axis direction, and may be connected to any one of the first and second line patterns 51 and 52. A length in the Y-axis direction of the first and second line patterns 51 and 52 may be greater than a length in the Y-axis direction of the first and second sensor electrodes 151 and 153.

As shown in FIG. 21, the sensing material 150 may include at least one first region R1 overlapped with different regions of the electrode portion 152 in the vertical direction and at least one a second region R2 not overlapped with the electrode portion 152. A plurality of spaced apart first regions R1 may be disposed, and a plurality of spaced apart second regions R2 may be disposed. The resistance of the sensing material 150 may be lowered by incident light or may have conductivity. The sensing material 150 may be disposed on the electrode portion 152. The second region R2 may be disposed between neighboring line patterns 51 and 52 of the electrode portion 152. The first and second regions R1 and R2 may have a predetermined length and may be alternately disposed. A portion of the second region R2 may be the same width as the interval B1 between the line patterns 51 and 52 of the electrode portion 152. The second region R2 may extend in one direction with a long length, and an extension direction of the second region R2 may be disposed parallel to the extension direction of the line patterns 51 and 52 of the electrode portion 152. The interval B1 between the first electrode portions 152 may be 50 μm or more, for example, in a range of 50 μm to 500 μm. A resistance value for measuring gas may be determined according to the interval B1 between the electrode portions 152. As the interval B1 between the electrode portions 152 is closer, the resistance value of the sensing material 150 may be lower. Accordingly, the neighboring line patterns 51 and 52 of the electrode portion 152 may be electrically connected.

The sensing material 150 may be in contact with the electrode portion 152 in a region between the line patterns 51 and 52 of the electrode portion 152. Since the sensing material 150 has a low resistance or conductivity due to light, it is possible to electrically connect the line patterns 51 and 52 of the adjacent electrode portions 152. The sensing material 150 may have a first resistance due to incident light, and may be changed to a second resistance lower than the first resistance when an external gas is introduced. Accordingly, the sensing material 150 may reduce the electrical resistance between the line patterns 51 and 52 of the electrode portion 152 by light and gas, and may electrically connect the line patterns 51 and 52 of the electrode portion 152 through the second region R2. The electrode portion 152 is electrically connected by the sensing material 150, and the resistance between the electrode portions 152 is lowered, and thus the resistance may be detected by the first and second pad portions 151 and 152. A change in the detected resistance may measure the presence or absence of gas by a semiconductor device.

The sensing material 150 may be disposed on the upper surface of the electrode portion 152 and in a region between the line patterns 51 and 52. When light and gas of a predetermined wavelength are input, the sensing material 150 may itself change the resistance of the electrode portion 152.

As another example, the electrode portion 152 may include materials such as nanopowder, nanowires, nanorods, carbon nanotubes (CNTs), and graphene, but is not limited thereto.

The second embodiment of the invention provides the electrode portion 152 connected between the first and second sensor electrodes 151 and 153 by the continuous line patterns 51 and 52, and thus initial resistance applied to the first and second sensor electrodes 151 and 153 may be determined. The sensing material 150 reacting to light having an arbitrary wavelength is disposed on the electrode portion 152, and the resistance applied to the electrode portion 152 is changed, thereby detecting whether gas is sensed or not. For example, when a resistance lower than the initial resistance applied to the first and second sensor electrodes 151 and 153 is detected, it is possible to detect a gas sensing state. Accordingly, the sensor unit 105A according to the embodiment may detect the presence or absence of gas leakage by light having the predetermined wavelength.

The embodiment may reduce a size and a thickness of the sensor unit 105A. That is, it is possible to solve problems such as durability of a heater, an increase in the size by the heater, and a time-consuming problem such as a warm-up time by implementing the sensor unit 105A by using light of an LED without the heater.

Figure 22:
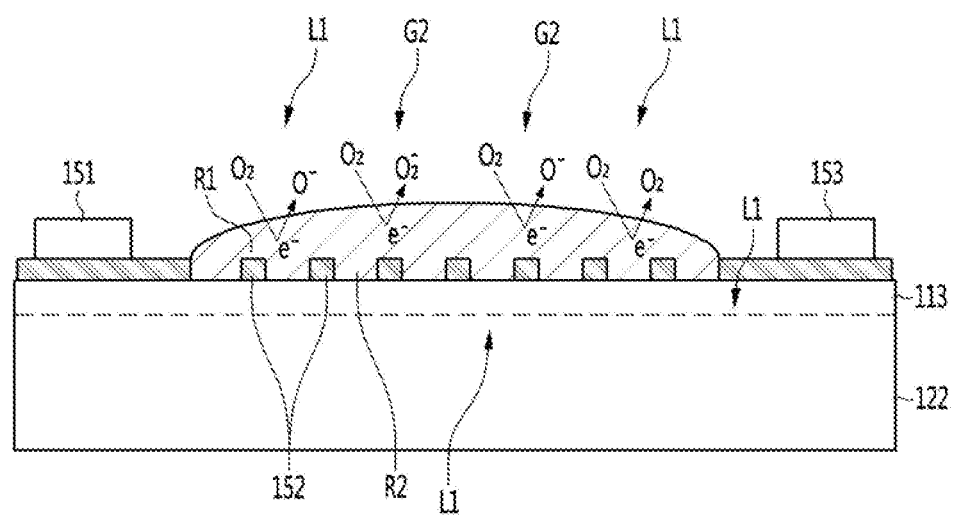
FIG. 22 is a view for explaining the operation of the semiconductor device of FIG. 20.

As shown in FIG. 22, in the sensor unit 105A according to an embodiment, electrons (e⁻) are generated when light L1 generated from the light emitting unit is emitted, and the sensing material 150 may react first with nitrogen or oxygen which occupies the largest composition ratio in the atmosphere. The nitrogen does not react with the sensing material 150 in the sensor unit 105A as an inert gas, and oxygen is adsorbed on a surface of the sensing material 150 to be present in a form of oxide ions such as $O^{2-}$, $O_2^-$, and $O^-$. At this time, the oxide ions and the gas G2 may react with each other to move electrons. At this time, a very large change in impedance, that is, a high sensitivity characteristic, may be shown according to movement of electrons on the surface of the sensing material 150. That is, the sensing material 150 generates the oxide ions by the reaction of the electrons and oxygen generated in the reaction with the light L1, and the oxide ions may react with the gas to move the electrons through the sensing material 150. The movement of the electrons in the sensing material 150 may connect neighboring line patterns 51 and 52 of the electrode portion 152, and may change the resistance of the electrode portion 152, and the change in the resistance of the sensing material 150 may be detected by a signal detection circuit through the first and second sensor electrodes 151 and 153. The gas may include $H_2$, $CO_2$, CO, HCl, $Cl_2$, $H_2S$, $H_2$, HCN, and the like. The sensing material 150 may have an impedance value in a range of several hundreds of KΩ to several tens of MΩ through a process and heat treatment as a semiconductor ceramic material.

The light L1 may be incident through a surface or/and a bottom surface of the sensing material 150. The light L1 may be light emitted from the light emitting unit. The light emitting unit may include an LED, and the LED may include at least one of ultraviolet light, visible light, and infrared light. The LED may include ultraviolet light. The sensing material 150 generates electrons at the surface of the sensing material 150 when the ultraviolet light L1 is emitted. A wavelength of the ultraviolet rays may be in a range of 390 nm or less, for example, 200 nm to 390 nm. The wavelength of the ultraviolet rays may be different according to a band gap of a main sensing material. For example, a band gap of $SnO_2$ may be about 3.6 eV. As shown in FIG. 22, when ultraviolet (UV) light is emitted to the sensing material 150, for example, in the case of 254 nm or 365 nm, it can be seen that a photo current flows. The embodiment may improve the reliability of the sensor unit 105A by providing the sensor unit 105A that generates electrons by using the light of the LED. The embodiment may solve problems such as durability of a heater and a time-consuming problem such as a warm-up time by implementing the sensor unit 105A by using light of an LED without the heater.

As shown in FIG. 34, when ultraviolet light is emitted to a sensing material 150 and external nitrogen dioxide ($NO_2$) is introduced therein, initial resistance of a sensing electrode may be further lowered according to a change in resistance of the sensing material 150. It is possible to determine whether gas is sensed according to a change rate in the resistance. At this time, a level of sensing sensitivity may become the initial resistance again when light of a predetermined wavelength is turned off. A comparative example is a change rate in resistance in a sensor unit having a heater.

Figure 23:
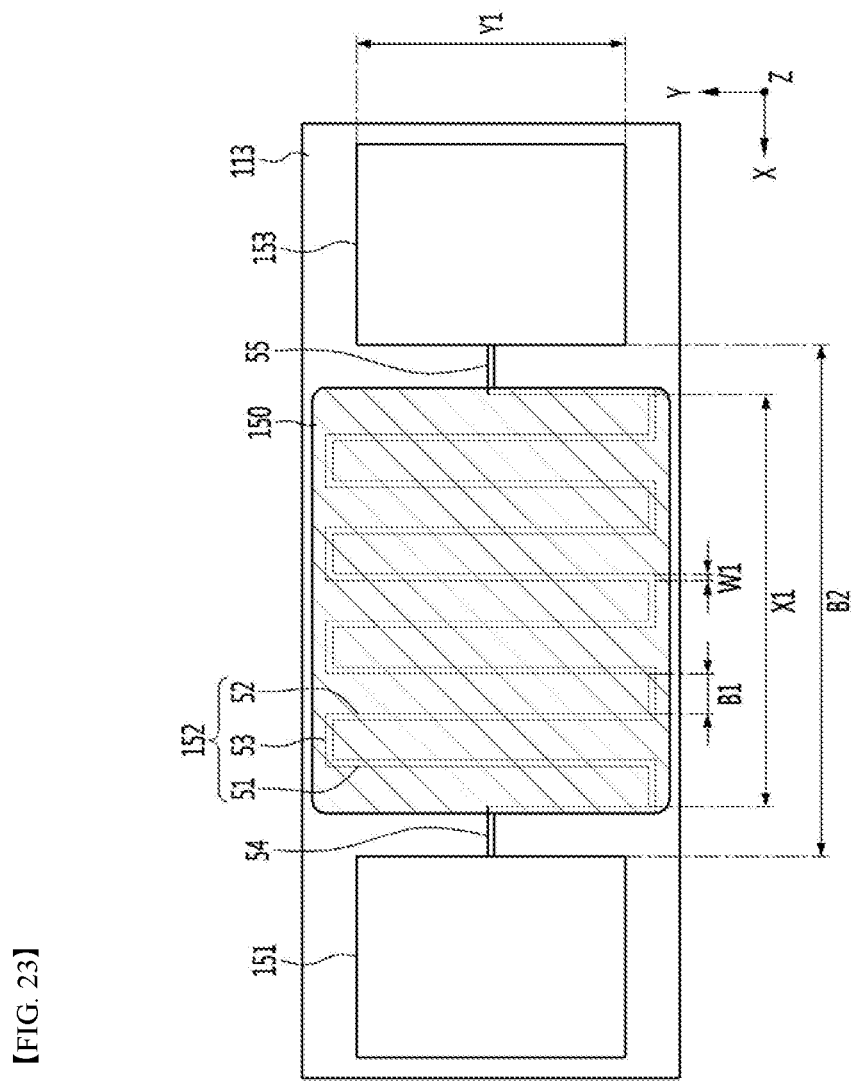
FIG. 23 is a first modification example of the semiconductor device of FIG. 20.

FIG. 23 is a first modification example of the semiconductor device of FIG. 20. In the configuration of FIG. 23, the configuration and description described above will be used selectively, and different portions will be described.

Referring to FIG. 23, a sensor unit 105A may include first and second sensor electrodes 151 and 153, an electrode portion 152, and a sensing material 150 on an insulating layer 113.

The sensing material 150 may be provided to cover both first and second line patterns 51 and 52 and a connection pattern 53 of the electrode portion 152. Since the sensing material 150 covers all of the patterns 51, 52 and 53, oxidation of the patterns 51, 52 and 53 of the electrode portion 152 may be suppressed and sensing sensitivity may be improved.

For example, a length Y1 in the Y-axis direction of the sensing material 150 may be greater than a length in the Y-axis direction of the line patterns 51 and 52. A width X1 in the X-axis direction of the sensing material 150 may be 80% or more of a distance B2 between the first and second sensor electrodes 151 and 153. The width X1 in the X-axis direction of the sensing material 150 may be equal to or greater than a distance between first and second end portions 54 and 55.

Figure 24:
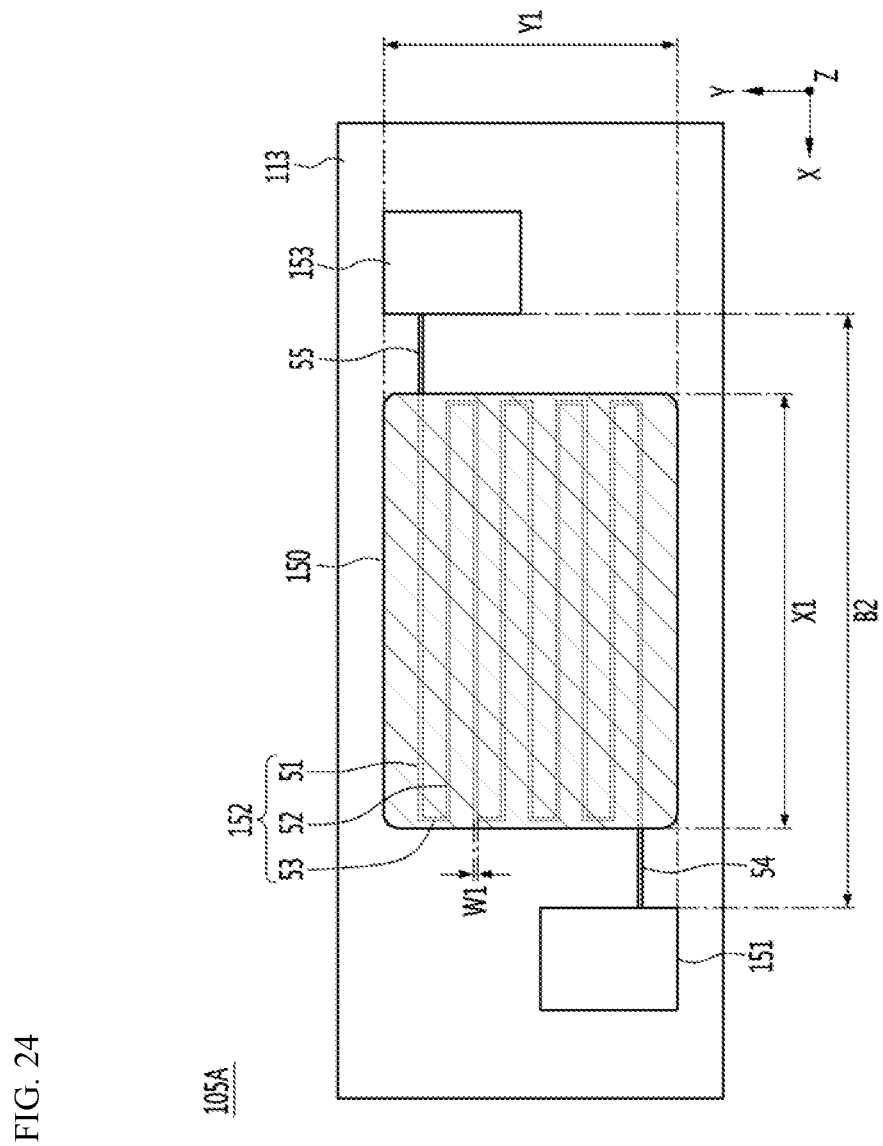
FIG. 24 is a second modification example of the semiconductor device of FIG. 20.

FIG. 24 is a second modification example of the semiconductor device of FIG. 20. In the configuration of FIG. 24, the configuration and description described above will be used selectively, and different portions will be described.

Referring to FIG. 24, a sensor unit 105A may include first and second sensor electrodes 151 and 153, an electrode portion 152 and a sensing material 150 on an insulating layer 113.

The first and second sensor electrodes 151 and 153 of the sensor unit 105A may be disposed on regions that are not facing each other. A distance between the first and second sensor electrodes 151 and 153 may be disposed to be longer than a width (or length) in the X-axis direction of the sensing material 150. The sensing material 150 may have a bottom area covering line patterns 51 and 52 of the electrode portion 152, and may be disposed on the electrode portion 152.

The electrode portion 152 may include the line patterns 51 and 52 disposed in the X-axis direction, and a connection pattern 53 connecting both ends of the line patterns 51 and 52 at different positions. The line patterns 51 and 52 may be arranged with a long length in the X-axis direction, and may be spaced apart from each other in the Y-axis direction. Here, the Y-axis directions of the line patterns 51 and 52 may be spaced apart at a predetermined interval. A longitudinal direction X of the line patterns 51 and 52 of the electrode portion 152 may be a direction orthogonal to the Y-axis direction. When light and gas of a predetermined wavelength are sensed, initial resistance according to a change in resistance of the sensing material 150 is changed, and thus the electrode 152 may sense the presence or absence of the gas.

Figure 25:
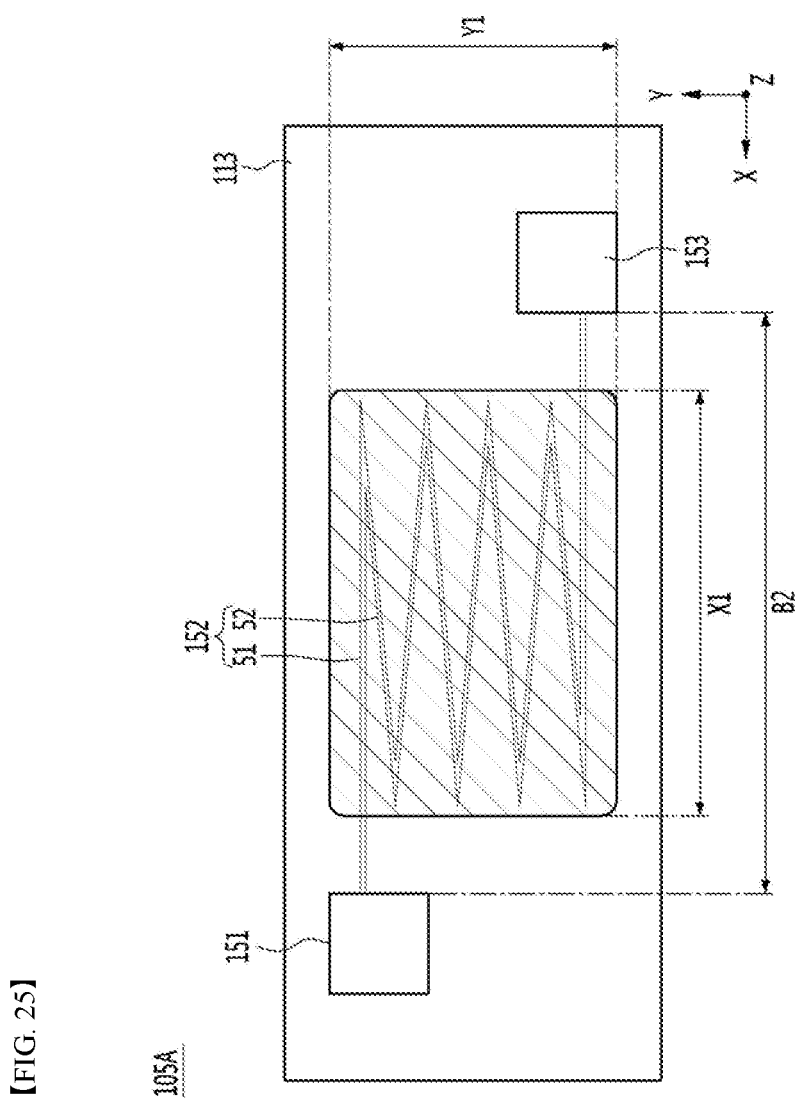
FIG. 25 is a third modification example of the semiconductor device of FIG. 20.

FIG. 25 is a third modification example of the semiconductor device of FIG. 20. In the configuration of FIG. 25, the configuration and description described above will be used selectively, and different portions will be described.

Referring to FIG. 25, a sensor unit 105A may include first and second sensor electrodes 151 and 153, an electrode portion 152 and a sensing material 150 on an insulating layer 113.

The electrode portion 152 may include a first line pattern 51 parallel to the X-axis direction and a second line pattern 52 having a zigzag shape from the first line pattern 51. The second line patterns 52 may be bent at an angle of 1 degree or more, for example, 10 degrees to 80 degrees or less. In the electrode portion 152, two adjacent line patterns 51 and 52 may be connected continuously in a triangle shape. An interval between the two line patterns 51 and 52 may be gradually narrower toward an intersection of the two line patterns. The interval between two line patterns 51 and 52 may be gradually narrower as it goes away from the intersection of the two line patterns. In the electrode portion 152, initial resistance may become a different resistance, for example, lowered according to a change in resistance of the sensing material 150, and it is possible to detect whether gas is sensed by detecting a change in the resistance.

Figure 26:
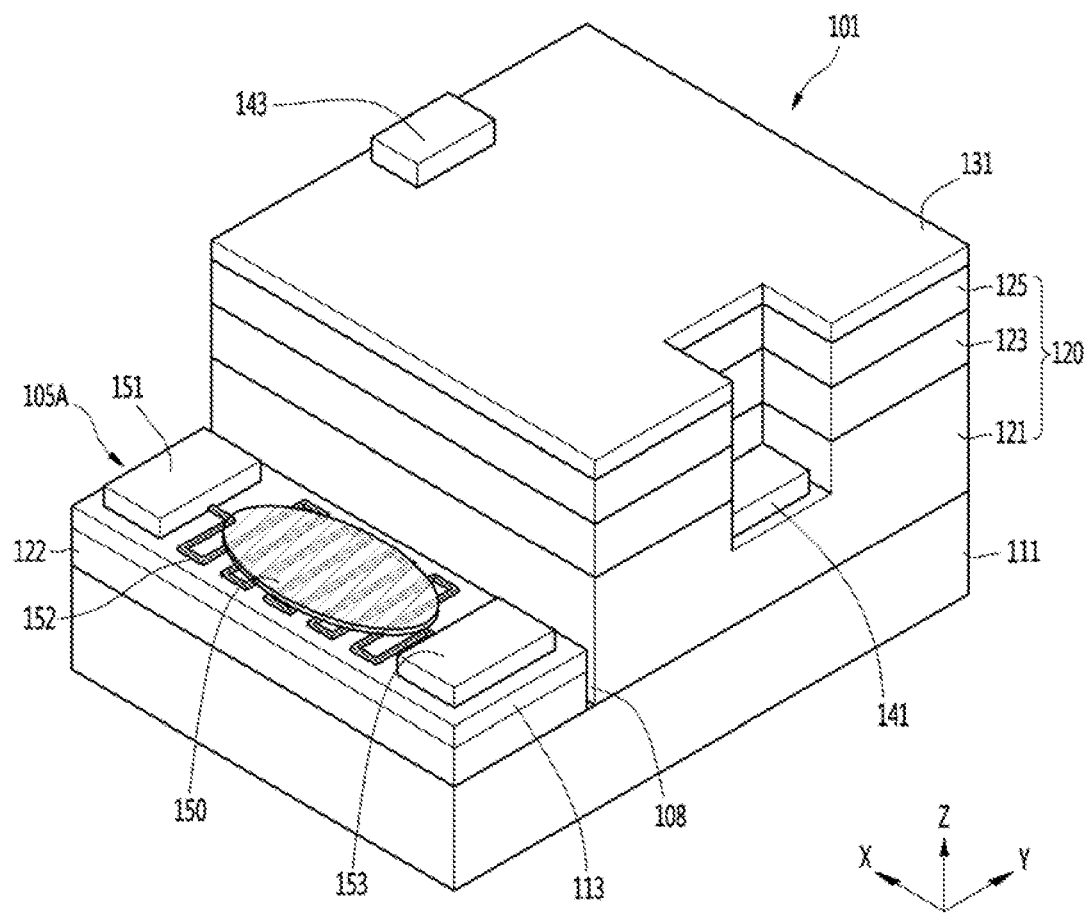
FIG. 26 is perspective view of a semiconductor device having a sensor unit, as another example of the second embodiment of the invention.

FIG. 26 is another example of the second embodiment. The semiconductor device disclosed in FIG. 26 is a configuration including the semiconductor device and the light emitting unit disclosed above. The same configuration as the configuration disclosed above will be described with reference to the configuration described above, and different portions will be described. The configurations disclosed above may be selectively applied to or combined with embodiments of the invention.

Referring to FIG. 26, the semiconductor device includes a light emitting unit 101 and a sensor unit 105A on the light emitting unit 101. The semiconductor device may be implemented as the light emitting unit 101 having the sensor unit 105A, or the sensor unit 105A having the light emitting unit 101. The semiconductor device may implement the sensor unit 105A in a region overlapped with at least a part of the light emitting unit 101 in a vertical direction Z. The semiconductor device may include a substrate 111 and the light emitting unit 101 disposed on a first region of the substrate 111, and the sensor unit 105A disposed on a second region.

The sensor unit 105A includes first and second sensor electrodes 151 and 153, an electrode portion 152, and a sensing material 150 disposed on the electrode portion 152. A detailed configuration of the sensor unit 105A will be described with reference to the configuration of the embodiment disclosed above. The sensor unit 105A may be disposed to be overlapped with the substrate 111 in the vertical direction, and may be spaced apart from the light emitting unit 101. The sensor unit 105A may be disposed adjacent to or facing at least one of the side surfaces of the light emitting unit 101. At least a part of the sensor unit 105A may be disposed to be overlapped with a part of a light emitting structure layer 120 of the light emitting unit in a horizontal direction of the X-axis and/or the Y-axis. When the sensing material 150 is activated by light emitted from the light emitting unit 101 and external gas is introduced into the sensor unit 105A, resistance of the electrode portion 152 is changed by the sensing material 150, thereby detecting whether gas is sensed or not.

The light emitting unit 101 according to an embodiment may be implemented by at least one of a horizontal chip structure, a vertical chip structure, and a flip chip structure, but is not limited thereto. The light emitting unit 101 may include, for example, a light-emitting element. The light-emitting element may include a light-emitting diode (LED), and the LED may emit at least one of ultraviolet light, visible light, and infrared light. The light emitting unit 101 according to the embodiment may emit light having an ultraviolet wavelength. In the semiconductor device according to the embodiment, a distance between the light emitting unit 101 and the sensor unit 105A may be equal to or less than twice a thickness of the light emitting unit 101, for example, 1.5 times or less.

In a size of the semiconductor device, the horizontal length×the longitudinal length may be, for example, in a range of 300 µm to 300,000 µm×300 µm to 30,000 µm. A thickness or a height of the semiconductor device may be 500 µm or less, for example, in a range of 30 µm to 500 µm. A first axis direction on a plane may be a lateral direction or the X-axis direction, and the second axis direction may be a longitudinal direction or the Y-axis direction orthogonal to the X-axis direction. A third axis direction may be a height or a thickness direction, or may be the Z-axis direction orthogonal to the first and second axis directions.

The light emitting unit 101 includes a light emitting structure layer 120 having a first conductivity type semiconductor layer 121, an active layer 123, and a second conductivity type semiconductor layer 125. The light emitting unit 101 may include a first electrode 141 connected to the first conductivity type semiconductor layer 121 and a second electrode 143 connected to the second conductivity type semiconductor layer 125. The light emitting unit 101 may include a substrate 111. The light emitting structure layer 120 may be disposed on the substrate 111. The substrate 111 may be a part of the configuration of the semiconductor device, or a part of the configuration of the light emitting unit 101 and/or the sensor unit 105A.

The light emitting unit 101 may be disposed in a region not overlapped with the sensor unit 105A in the vertical direction. The light emitting unit 101 may be disposed on a region different from the sensor unit 105A on the substrate 111. A part of light generated from the light emitting unit 101 may travel in a direction of the sensing material 150.

A configuration of the substrate 111, the light emitting structure layer 120, the first electrode 141, and the second electrode 143 of the light emitting unit 101 will be described with reference to the description of the first embodiment, and it may be selectively applied to the second embodiment.

The light emitting unit 101 includes a conductive layer 131, and the conductive layer 131 may be disposed on the light emitting structure layer 120. The conductive layer 131 may be disposed in at least one or both of a region between the second conductivity type semiconductor layer 125 and the second electrode 143 and a region between the first conductivity type semiconductor layer 121 and the first electrode 141. For example, the conductive layer 131 may be disposed on the second conductivity type semiconductor layer 125, and may be electrically connected to the second conductivity type semiconductor layer 125 and the second electrode 143. A material of the conductive layer 131 will be described with reference to the above description. The conductive layer 131 may be removed from the light emitting unit 101. When the conductive layer 131 is a metal material, it may be formed to a thickness of 10 nm or less, for example, 1 nm to 5 nm, for transmission of light. As another example, the conductive layer 131 may be removed, in this case, the second electrode 143 may be in contact with an upper surface of the multi-layered second conductivity type semiconductor layer 125. The conductive layer 131 may be formed of an AlGaN-based semiconductor so as to improve an ohmic contact and reduce light absorption loss, but the invention is not limited thereto.

The sensor unit 105A may include a configuration of the sensor unit disclosed in FIGS. 20 to 25. The sensor unit 105A includes first and second sensor electrodes 151 and 153, an electrode portion 152, and a sensing material 150. The sensor unit 105A may be disposed on an insulating layer 113, or may include the insulating layer 113.

The insulating layer 113 includes an insulating material or an insulating resin formed of at least one of an oxide, a nitride, a fluoride, and a sulfide having at least one of Al, Cr, Si, Ti, Zn and Zr. For example, the insulating layer 113 may be selectively formed of $SiO_2$, $Si_3N_4$, $Al_2O_3$, $TiO_2$, or MgO.

The insulating layer 113 may be disposed between the electrode portion 152 and the sensing material 150 and the semiconductor layer or the substrate 111. The insulating layer 113 may be disposed on a semiconductor layer 122. The semiconductor layer 122 may be the first conductivity type semiconductor layer, a buffer layer, or an unintentional doped semiconductor. The semiconductor layer 122 may be equal to or thinner than a thickness of the first conductivity type semiconductor layer.

The sensor unit 105A may be disposed on the substrate 111. The substrate 111 may extend under the sensor unit 105A. Accordingly, the light emitting unit 101 may be disposed on a first region of the substrate 111, and the sensor unit 105A may be disposed on a second region. The sensor unit 105A may be integrally formed with or separated from the light emitting unit 101. The sensor unit 105A may be disposed adjacent to at least one of the side surfaces of the light emitting unit 101. The sensing material 150 of the sensor unit 105A may be disposed in a region corresponding to a side surface of the active layer 123 of the light emitting unit, thereby improving incident efficiency of light.

The light emitting unit 101 according to an embodiment may emit ultraviolet light, visible light or infrared light, and for example, may emit ultraviolet light. The light emitting unit 101 may include various electronic elements such as an LED and a light receiving element, and the LED and the light receiving element may include a first conductivity type semiconductor layer, an active layer, and a second conductivity type semiconductor layer. The light emitting unit 101 according to the embodiment of the invention may be an LED.

The light emitting unit 101 may emit light when power is supplied to first and second electrodes 141 and 143. Light emitted through an upper surface, a lower surface, and side surfaces of the light emitting unit 101 may be irradiated to the sensing material 150 of the adjacent sensor unit 105A. The first and second sensor electrodes 151 and 153 may detect a change in resistance of the sensing material 150 through the electrode portion 152 when light is irradiated from the light emitting unit 101 and external gas is sensed. An operation of the sensor unit will be described with reference to the above description.

A groove 108 may be disposed between the sensor unit 105A and the light emitting unit 101. The insulating layer 113 may extend into the groove 108 to separate the semiconductor device 101 therefrom.

The sensing material 150 may be formed of a metal oxide material. The sensing material 150 may include a main sensing material and a catalyst. The main sensing material may include a metal oxide material, and the catalyst may include a metal. The main sensing material may include at least one or more of $SnO_2$, $CuO$, $TiO_2$, $In_2O_3$, $ZnO$, $V_2O_5$, $RuO_2$, $WO_3$, $ZrO_2$, $MoO_3$, $NiO$, $CoO$, $Fe_2O_3$, and $AB_2O_4$, and may be formed of various materials which are not limited thereto. For example, the catalyst of the sensing material 150 may include at least one or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), ruthenium (Ru), rhodium (Rh), silver (Ag), hafnium (Hf), tantalum (Ta), tungsten (W), rhenium (Re), and iridium (Ir). The catalyst material may be mixed with the main sensing material as a doping material in the sensing material 150. The sensing material 150 may include materials that may have both sensing and catalytic properties. The material of the sensing material 150 according to an embodiment may be selectively mixed in the main sensing material and the catalyst according to the type of gas to be sensed. The meaning of sensing by the sensor unit 105A may mean not only the presence or absence of a measurement gas, but also a change in concentration of the measurement gas.

The sensing material 150 may be in contact with a surface of the electrode portion 152 to change resistance. In the sensing material 150, one or more kinds of main sensing materials may be mixed, and the mixed material may be doped with one or two kinds of catalyst materials. The catalyst material may be added at 5 wt % or less of the main sensing material, for example, in a range of 1 wt % to 5 wt %, and the gas sensing sensitivity may be lowered when the catalyst material exceeds the above range. For example, when $SnO_2$ and ZnO are mixed, in the sensing material 150, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt to 3 wt % of the main sensing material. Here, since $SnO_2$ has a band gap of about 3.6 eV, a photo current may be formed when light emitted from the light emitting unit 101 is 340 nm. A particle size of the main sensing material is 30 nm or more, for example, in a range of 30 nm to 60 nm. When the particle size is small, characteristics may be improved, but costs may be increased, and when the particle size is larger than the above range, surface energy becomes small, and thus oxygen vacancies may not be formed.

FIG. 27 is a modification example of the semiconductor device of FIG. 26.

Referring to FIG. 27, a reflective plate 570 may be disposed on the semiconductor device of FIG. 26. The reflective plate 570 may include at least one of a metal material such as Ag, Ni, Al, Rh, Pd, Ir, Ru, Mg, Zn, Pt, Cu, Au and Hf.

The reflective plate 570 may be disposed on a light emitting unit 101. The reflective plate 570 may be spaced apart from the light emitting unit 101, and may reflect light emitted from the light emitting unit 101. For example, ultraviolet light may be reflected. The reflective plate 570 may have an opening part 572 therein, and the opening part 572 may be an opening through which gas according to an embodiment is introduced. The opening part 572 may have a minimum size such that light emitted from the light emitting unit 101 is not leaked to the outside. One or more opening parts 572 may be included, and may be disposed to partially overlap with the sensing material 150.

A side wall for preventing light leakage may be disposed around an outer circumference of the light emitting unit 101 and the sensor unit 105A. A circuit board for supplying power may be disposed under the semiconductor device 101 and the sensor unit 105A FIG. 28 is another example of the second embodiment, and is a configuration including the semiconductor device and the light emitting unit disclosed above. The same configuration as the configuration disclosed above will be described with reference to the configuration described above, and different portions will be described. The configurations disclosed above may be selectively applied to or combined with embodiments of the invention Referring to FIG. 28, a semiconductor device 100 may include a light emitting unit 101 and the above-disclosed sensor unit 105A on the light emitting unit 101. The sensor unit 105A may include first and second sensor electrodes 151 and 153, an electrode portion 152, and a sensing material 150.

An insulating layer 113 may be disposed between the sensor unit 105A and the light emitting unit 101. The insulating layer 113 may be disposed between the sensing material 150 and a conductive layer 131. The insulating layer 113 may be disposed between the electrode portion 152 and the light emitting structure layer 120 or the conductive layer 131. The insulating layer 113 may electrically insulate between the sensor unit 105A and the light emitting unit 101.

In an embodiment, a part or all of the configuration of the sensor unit 105A may be disposed to be overlapped with at least a part of the light emitting unit 101 in the vertical direction. In the embodiment, a part or all of the configuration of the sensor unit 105A may be disposed to be overlapped with at least a part of the light emitting structure layer 120 in the vertical direction. The sensing material 150 may be disposed to be overlapped with at least one of a first conductivity type semiconductor layer 121 and a second conductivity type semiconductor layer 125 in a vertical direction. The sensing material 150 may be disposed to be overlapped with an active layer 123 in the vertical direction. The first and second sensor electrodes 151 and 153 and the electrode portion 152 may be disposed to be overlapped with at least one of the first conductivity type semiconductor layer 121 and the second conductivity type semiconductor layer 125 in the vertical direction. The first and second sensor electrodes 151 and 153 and the electrode portion 152 may be disposed to be overlapped with the active layer 123 in the vertical direction.

As shown in FIG. 21, the sensing material 150 may include a plurality of first regions R1 overlapped with different regions of the electrode portion 152 in the vertical direction, and a second region R2 protruding toward a substrate 111 or a bottom direction between the plurality of first regions R1. The electrode portions 152 may be a single line pattern connected in series.

The sensing material 150 may be disposed above the active layer 123 to improve incident efficiency of light emitted through the active layer 123. Layers between the sensing material 150 and the active layer 123 may be formed of a material transmitting light emitted through the active layer 123. The sensing material 150 may be disposed to be separated from a surface of at least one layer of the light emitting structure layer 120 to prevent electrical interference.

The sensing material 150 may be formed of a metal oxide material. The sensing material 150 may include a main sensing material and a catalyst. The main sensing material may include a metal oxide material, and the catalyst may include a metal. The main sensing material may include at least one or more of $SnO_2$, CuO, $TiO_2$, $In_2O_3$, ZnO, $V_2O_5$, $RuO_2$, $WO_3$, $ZrO_2$, $MoO_3$, NiO, CoO, $Fe_2O_3$, and $AB_2O_4$, and may be formed of various materials which are not limited thereto. For example, the catalyst of the sensing material 150 may include at least one or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), ruthenium (Ru), rhodium (Rh), silver (Ag), hafnium (Hf), tantalum (Ta), tungsten (W), rhenium (Re), and iridium (Ir). The catalyst material may be mixed with the main sensing material as a doping material in the sensing material 150. The sensing material 150 may include materials that may have both sensing and catalytic properties. The material of the sensing material 150 according to an embodiment may be selectively mixed in the main sensing material and the catalyst according to the type of gas to be sensed. The meaning of sensing by the sensor unit 105A may mean not only the presence or absence of a measurement gas, but also a change in concentration of the measurement gas.

The sensing material 150 may be in contact with a surface of the electrode portion 152 to change resistance. In the sensing material 150, one or more kinds of main sensing materials may be mixed, and the mixed material may be doped with one or two kinds of catalyst materials. The catalyst material may be added at 5 wt % or less of the main sensing material, for example, in a range of 1 wt % to 5 wt %, and the gas sensing sensitivity may be lowered when the catalyst material exceeds the above range. For example, when $SnO_2$ and ZnO are mixed, in the sensing material 150, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt % to 3 wt % of the main sensing material. Here, since $SnO_2$ has a band gap of about 3.6 eV, a photo current may be formed when light emitted from the light emitting unit 101 is 340 nm. A particle size of the main sensing material is 30 nm or more, for example, in a range of 30 nm to 60 nm. When the particle size is small, characteristics may be improved, but costs may be increased, and when the particle size is larger than the above range, surface energy becomes small, and thus oxygen vacancies may not be formed.

The line patterns (51 and 52 in FIG. 20) of the electrode portion 152 have a long length in one direction, and a length direction of the line pattern may be the same direction as an imaginary straight line connecting first and second electrodes 141 and 143 of the light emitting unit, for example, the X-axis direction. The line patterns of the electrode portion 152 may be continuously connected at a predetermined interval in the Y-axis direction. As another example, the length direction of the line patterns of the electrode portion 152 in the sensor unit 105A may be arranged in a direction orthogonal to a direction of the imaginary straight line connecting the first and second electrodes 141 and 143. Structures of the first and second sensor electrodes 151 and 153, the sensing material 150, and the electrode portion 152 of the sensor unit 105A according to an embodiment may be selectively applied to the configurations of FIGS. 20 to 25, and are not limited thereto.

The sensor unit 105A according to an embodiment may be disposed to correspond to at least one of an upper surface and a side surface of the light emitting unit 101 emitting light as shown in FIGS. 23 and 28. For example, the sensing material 150 of the sensor unit 105A may correspond to or face at least one of the upper surface and the side surface of the light emitting unit 101. The sensing material 150 may be a region exposed such that light emitted from the light emitting unit 101 is incident.

The sensor unit 105A may be disposed on a region overlapped with the light emitting structure layer 120 in the vertical direction. Accordingly, in the sensing material 150, incidence efficiency of light emitted from the light emitting unit 101 may be improved.

Since the sensor unit 105A is disposed on the light emitting structure layer 120, a light-emitting area of the active layer 123 may not be reduced or the light-emitting area may be increased.

Since the sensor unit 105A is disposed on the light emitting structure layer 120, external gas sensing sensitivity may be improved.

Since the sensor unit 105A is disposed on the light emitting structure layer 120, a sensing device having the semiconductor device may be downsized.

As another example, the substrate 111 of the light emitting unit 101 may be a conductive substrate, and in this case, the first electrode 141 may not be formed separately. As another example, a reflective layer may be further disposed under the substrate 111 of the light emitting unit 101 to improve light emission efficiency.

FIG. 29 is another example of the second embodiment of the invention. The same configuration as that of the above-disclosed embodiment refers to the configuration of the above embodiment, and the configuration disclosed above may be selectively applied to an embodiment of the invention.

Referring to FIG. 29, a semiconductor device may include a light emitting unit 101C and a sensor unit 105A on the light emitting unit 101C. An insulating layer 113 may be disposed between the light emitting unit 101C and the sensor unit 105A.

The light emitting unit 101C may include a light emitting structure layer 120, and an upper surface of the light emitting structure layer 120 may be formed with a concave-convex structure 121B. A branch electrode 141C of a first electrode 141 may extend in a partial region of the concave-convex structure 121B, but the invention is not limited thereto. The branch electrode 141C may be a transparent conductive layer or a metal material.

The sensor unit 105A is disposed on the light emitting unit 101C. The insulating layer 113 may be disposed between the light emitting unit 101C and the sensor unit 105A. The insulating layer 113 may extend from an upper surface of the light emitting unit 101C toward a side surface of the light emitting structure layer 120.

The sensor unit 105A may include first and second sensor electrodes 151 and 153, an electrode portion 152, and a sensing material 150 disclosed in an embodiment, and a detailed configuration refers to the configuration disclosed above. The first and second sensor electrodes 151 and 153 and the electrode portion 152 may be disposed on the light emitting structure layer 120. The sensing material 150 may be in contact with the electrode portion 152. A lower surface of the sensing material 150 and the electrode portion 152 may have a concave-convex shape along the concave-convex structure 121B. Since the electrode portion 152 in the concave-convex shape has a large surface area, a contact area with the sensing material 150 may be increased. Accordingly, a length and width of the electrode portion 152 may be reduced.

As shown in FIG. 21, the sensing material 150 may include a plurality of first regions R1 overlapped with different regions of the electrode portion 152 in a vertical direction, and a second region R2 protruding toward a substrate 111 or a bottom direction between the plurality of first regions R1. The electrode portion 152 may be a single line pattern connected in series.

The light emitting unit 101C includes a first electrode 141B on a first conductivity type semiconductor layer 121 and a second electrode 143B having a plurality of conductive layers 146, 147, 148, and 149 under a second conductivity type semiconductor layer 125. A position of the first electrode 141B may be selectively applied in the above-disclosed embodiment.

The second electrode 143B is disposed under the second conductivity type semiconductor layer 125, and includes a contact layer 146, a reflective layer 147, a bonding layer 148, and a support member 149. The contact layer 146 is in contact with a semiconductor layer, for example, the second conductivity type semiconductor layer 125. The contact layer 146 may be a low conductive material such as ITO, IZO, IZTO, IAZO, IGZO, IGTO, AZO, ATO, or a metal of Ni or Ag may be used. The reflective layer 147 is disposed under the contact layer 146, and the reflective layer 147 is formed as a structure including at least one layer of a material selected from the group consisting of Ag, Ni, Al, Rh, Pd, Ir, Ru, Mg, Zn, Pt, Au, Hf, and combinations thereof. The reflective layer 147 may be in contact with the second conductivity type semiconductor layer 125, but the invention is not limited thereto.

The bonding layer 148 may be disposed under the reflective layer 147, and may be used as a barrier metal or a bonding metal, and the material may include, for example, at least one of Ti, Au, Sn, Ni, Cr, Ga, In, Bi, Cu, Ag, and Ta, and selective alloys thereof.

A protective layer 183 and a current blocking layer 185 are disposed between the second conductivity type semiconductor layer 125 and the second electrode. The insulating layer 113 may extend to an upper surface of an outer side portion of the protective layer 183. The protective layer 183 may be formed along an edge of a lower surface of the second conductivity type semiconductor layer 125, and may be formed in a ring shape, a loop shape, or a frame shape having an open inside. The protective layer 183 may include a transparent conductive material or an insulating material, and may include, for example, at least one of ITO, IZO, IZTO, IAZO, IGZO, IGTO, AZO, ATO, $SiO_2$, $SiO_x$, $SiO_xN_y$, $Si_3N_4$, $Al_2O_3$, and $TiO_2$. The inner side portion of the protective layer 183 is disposed under the second conductivity type semiconductor layer 125, and the outer side portion of the protective layer 183 is disposed further outward than a side surface of the light emitting structure layer 120. The current blocking layer 185 may be disposed between the second conductivity type semiconductor layer 125 and the contact layer 146 and/or the reflective layer 147. The current blocking layer 185 may include at least one of $SiO_2$, $SiO_x$, $SiO_xN_y$, $Si_3N_4$, $Al_2O_3$, and $TiO_2$. As another example, the current blocking layer 185 may also be formed of a metal for a Schottky contact. The current blocking layer 185 is disposed to be overlapped with a first electrode 141B disposed on the light emitting structure layer 120 in a thickness direction of the light emitting structure layer 120. The current blocking layer 185 may diffuse a current supplied from the second electrode 170 to another path. One or a plurality of current blocking layers 185 may be disposed, and at least a part or all regions may be overlapped with the first electrode 141B in the vertical direction.

The support member 149 is formed under the bonding layer 148, and the support member 149 may be formed as a conductive member, and may be formed of a conductive material such as copper (Cu), gold (Au), nickel (Ni), molybdenum (Mo), copper-tungsten (Cu—W), and carrier wafers (e.g., Si, Ge, GaAs, ZnO, SiC and the like). As another example, the support member 149 may be implemented as a conductive sheet. Here, the substrate of FIG. 1 may be removed. The substrate may be removed by a physical method such as laser lift off or a chemical method such as wet etching to expose the first conductivity type semiconductor layer 121. The first electrode 141B is formed on the first conductivity type semiconductor layer 121 by performing isolation etching through a direction in which the substrate is removed.

When the sensor unit 105A is applied on the light emitting unit of such a vertical chip structure, an amount of light incident on the sensing material 150 may be maximized, and a gas contact area in the sensing material 150 may be maximized. In addition, heat dissipation efficiency may be maximized by the vertical chip structure.

The sensor unit according to an embodiment may be disposed in a region not overlapped with the light emitting structure layer 120 in the vertical direction to reduce light loss. In this case, a surface area of the sensing material 150 of the sensor unit 105A may be further increased.

FIG. 30 is another example of the second embodiment of the invention, and is a configuration in which a sensor unit 105A is disposed on a light emitting unit of a flip chip structure.

Referring to FIG. 30, in a light emitting unit 101D, a substrate 111 is disposed on a light emitting structure layer 120. The substrate 111 may be an insulating material, a semiconductor material, or a transparent material. The substrate 111 may include a material through which light emitted from the light emitting structure layer 120 is transmitted. An upper surface of the substrate 111 may be formed with a concave-convex structure 111B, or a lens shape having a flat surface or a curvature may be disposed in at least one or more.

A sensor unit 105A is disposed on the substrate 111 made of an insulating material. In this case, the insulating layer 113 shown in FIG. 21 may be removed. The sensor unit 105A may include first and second sensor electrodes 151 and 153, an electrode portion 152, and a sensing material 150 disclosed in an embodiment, and a detailed configuration may apply selectively the above-disclosed configuration.

The sensing material 150 of the sensor unit 105A may be disposed on the substrate 111. Lower surfaces of the first and second sensor electrodes 151 and 153 and the electrode portion 152 may be disposed along the concave-convex structure 111B of the substrate 111 as a concave-convex surface. A line pattern of the electrode portion 152 may extend to have a concavo-convex shape along the concave-convex structure 111B of the upper surface of the substrate 111. Since the electrode portion 152 having such a concavo-convex shape have a large surface area, a contact area with the sensing material 150 may be increased.

The light emitting structure layer 120 may include a first conductivity type semiconductor layer 121, an active layer 123, and a second conductivity type semiconductor layer 125 under the substrate 111. A protective layer 133 may be disposed under the light emitting structure layer 120. The protective layer 133 may be formed of an insulating material. A first electrode 141 may be disposed under the first conductivity type semiconductor layer 121. A second electrode 143 may be disposed under the second conductivity type semiconductor layer 125, and may be electrically connected.

A conductive layer 114 may be disposed between the second conductivity type semiconductor layer 125 and the protective layer 133. The conductive layer 114 may be formed of a metal of a reflective material. The conductive layer may include at least one of a material selected from the group consisting of Ag, Ni, Al, Rh, Pd, Ir, Ru, Mg, Zn, Pt, Au, Hf, Cr, Ti, Cu, and a combination thereof. In the conductive layer 114, a transparent material layer and a reflective material layer may be stacked. The conductive layer 114 may be connected to the second electrode 143. The second electrode 143 may be disposed in one or plural.

In such a flip chip structure, the first and second electrodes 141 and 143 of the light emitting unit 101D and the first and second sensor electrodes 151 and 153 of the sensor unit 105A may be separated. The first and second electrodes 141 and 143 may be disposed under the light emitting unit 101D, and the first and second sensor electrodes 151 and 153 may be disposed over the light emitting unit 101D. The sensing material 150 may be applied to an entire region of the upper surface of the substrate 111, thereby increasing a surface area of the sensing material 150.

FIG. 31 is a first modification example of a sensing device having the semiconductor device according to the second embodiment of the invention. In describing FIG. 31, the above-disclosed configuration refers to the above description, and may be selectively applied to the sensing device.

Referring to FIG. 31, a gas sensing device may include a circuit board 550, a sensor unit 105A on the circuit board 550, a light emitting unit 101A on the circuit board 550, a package body 560 surrounding the sensor unit 105A and the light emitting unit 101A, and a reflective plate 570 on the package body 560. Although the sensor unit 105A and the light emitting unit 101A are described as an example separated from each other. It may be implemented by the light emitting unit disclosed in FIGS. 26 to 30 and the semiconductor device spaced apart therefrom, but the invention is not limited thereto.

The circuit board 550 may include at least one of a resin PCB, a metal core PCB (MCPCB), and a flexible PCB (FPCB), but the invention is not limited thereto. The circuit board 550 may include a ceramic material.

The package body 560 may be a ceramic material. The package body 560 may be formed of the same ceramic material as the circuit board 550. The circuit board 550 may include a plurality of circuit patterns (not shown) on an upper surface thereof, and the plurality of circuit patterns may be electrically connected to the sensor unit 105A and the light emitting unit 101A. The circuit pattern may be connected to sensor electrodes 151 and 153 of the sensor unit 105A by wires or other conductive members. The circuit pattern may be connected to electrodes of the semiconductor device through the wires or may be directly bonded.

The sensor unit 105A and the light emitting unit 101A may be disposed inside the package body 560. A reflective plate 570 is disposed on the package body 560, and the reflective plate 570 may reflect light to prevent leakage of light. An inside 565 of the package body 560 may be formed in a cavity structure or a concave recess structure. A stepped structure may be disposed around an upper portion of the package body 560, and the reflective plate 570 may be closely coupled on the stepped structure. The reflective plate 570 may be in contact with the package body 560 with an adhesive (not shown).

The sensor unit 105A may sense a gas exposing by light emitted from the light emitting unit 101A and a gas introduced through an opening part 572 of the reflective plate 570, for example, a harmful gas.

The light emitting unit 101A and the sensor unit 105A are separately disposed on the circuit board 550, but the light emitting unit 101 may be integrally disposed on the substrate of the semiconductor device.

FIG. 32 is another example of a sensing device having the semiconductor device according to the second embodiment, and is an example of the sensing device having the semiconductor device of FIG. 28. In description of FIG. 32, the above-disclosed configuration refers to the above description, and may be selectively applied to the sensing device. The semiconductor device of the sensing device of FIG. 32 will be described as an example of the sensor unit of FIG. 28

Referring to FIG. 32, the sensing device may include a circuit board 550, a semiconductor device 100B having a light emitting unit 101 and a sensor unit 105A on the circuit board 550, a package body 560 around the semiconductor device 100B, and a reflective plate 570 disposed on the semiconductor device 100B and the package body 560.

The light emitting unit 101 may be disposed on a first region of the circuit board 550, and the sensor unit 105A may be disposed on a second region of the circuit board 550. The light emitting unit 101 may be disposed between the sensor unit 105A and the circuit board 550.

The package body 560 may be a ceramic material. The package body 560 may be formed of the same ceramic material as a material of a body of the circuit board 550. Such a ceramic material may effectively reflect light emitted from the light emitting unit 101. An inside 565 of the package body 560 has a cavity or a recess structure, and the sensor unit 105A and the light emitting unit 101 may be disposed therein. A reflective plate 570 is disposed on the package body 560, and the reflective plate 570 may reflect light to prevent leakage of light. A stepped structure may be disposed around an upper portion of the package body 560, and the reflective plate 570 may be closely coupled on the stepped structure. The reflective plate 570 may be in contact with the package body 560 with an adhesive (not shown). The sensor unit 105A may sense a gas exposing by light emitted from the light emitting unit 101 and a gas introduced through an opening part 572 of the reflective plate 570, for example, a harmful gas. The light emitting unit 101 and the sensor unit 105A are overlapped on the circuit board 550, and a configuration of another embodiment disclosed above may be applied selectively.

In an embodiment, any one of first and second sensor electrodes 151 and 153 of the sensor unit may be commonly connected to any one of first and second electrodes of the light emitting unit. For example, the first pad portion and the first electrode may be connected in common, but the invention is not limited thereto. A configuration of the semiconductor device may apply the configurations of FIGS. 26, 29 and 30, but the invention is not limited thereto.

Figure 33:
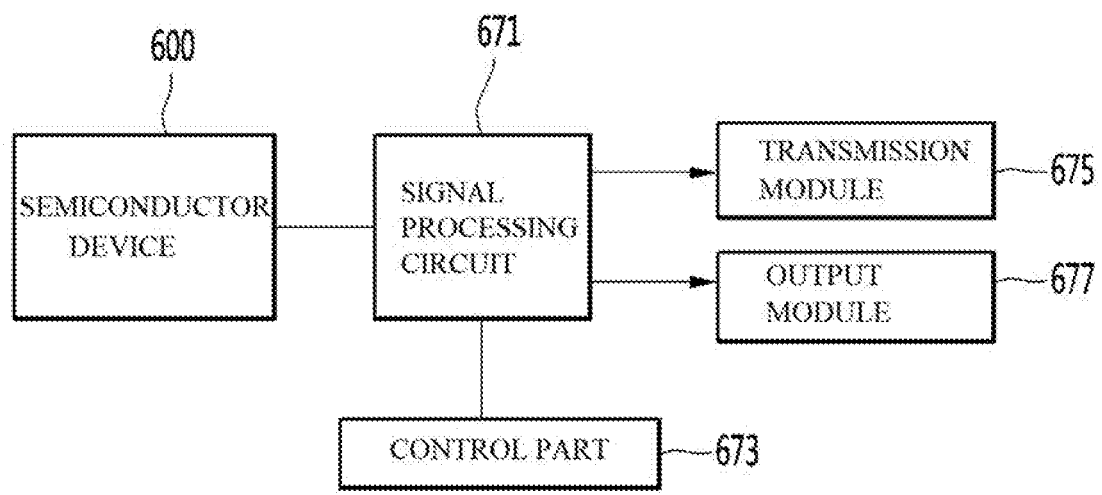
FIG. 33 is a block diagram showing a gas sensing system according to an embodiment of the invention.

FIG. 33 is an example of a block diagram of a sensing system having a semiconductor device according to an embodiment of the invention.

Referring to FIG. 33, a change in resistance sensed by a semiconductor device 600 is detected by a signal processing circuit 671, and the signal processing circuit 671 detects gas through a change in resistance due to an inflow of gas. When gas is detected, the signal processing circuit 671 may transmit a signal through a transmission module 675 by wired or wireless communication, or inform a user through an output module 677 by an alarm or a display mode. A control part 673 may be disposed in such a system. The control part 673 may control the output or transmission of the signal processing circuit 671.

The semiconductor device or the sensing device according to an embodiment may be applied to a place or a device in which gas such as various kinds of toxic gas or explosive gas is generated, for example, a moving device such as a vehicle or an enclosed space. Alternatively, it may be applied to indoor or outdoor sensing devices.

According to an embodiment of the invention, the first region and the second region of the sensing material may be alternately disposed. The electrode portion may include a plurality of line patterns overlapped with the first region of the sensing material in a vertical direction. The first and second pad portions and the electrode portion may be overlapped with the active layer in the vertical direction. An interval between the line patterns may be greater than a width of each of the line patterns, and an entire length of the electrode portions may be longer than a distance between the first and second pad portions. The second region may be disposed between the line patterns.

According to an embodiment of the invention, an insulating layer may be disposed between the sensing material and the light emitting unit. The light emitting unit may include a conductive layer between the sensor unit and the second conductivity type semiconductor layer. The substrate may be disposed between the light emitting structure layer and the sensor unit. The light emitting unit generates ultraviolet light, and the sensing material may react with the ultraviolet light. The substrate may include a transparent material or a conductive material. The electrode portion may be electrically separated from the first and second electrodes.

Third Embodiment

FIG. 35 is a perspective view of a semiconductor device according to a third embodiment, FIG. 36 is a plan view of the semiconductor device of FIG. 35, FIG. 37 is a partially enlarged view of the semiconductor device of FIG. 36, FIG. 38 is a cross-sectional view of the semiconductor device taken along a line A1-A1 of FIG. 36, and FIG. 39 is a side cross-sectional view of the semiconductor device taken along line B1-B1 of FIG. 36.

Referring to FIGS. 35 to 39, a semiconductor device 100E according to the third embodiment includes a support member 350, a light emitting unit 301 on a first region of the support member 350, and a sensor unit 105C on a second region of the support member 350.

In the semiconductor device 100E, an electrode structure such as a lead electrode or a frame may be disposed on the support member 350. The electrode structure may include first and second lead electrodes 320 and 330 connected to the light emitting unit 301. The electrode structure may include sensor electrodes 151 and 153 of the sensor unit 105C.

In the semiconductor device 100E, the light emitting unit 301 and the sensor unit 105C may be disposed on different regions of the support member 350. In the semiconductor device 100E, the light emitting unit 301 and the sensor unit 105C may be not overlapped in the vertical direction Z. The light emitting unit 301 and the sensor unit 105C may be disposed to be overlapped with each other in the horizontal direction based on the light emitting unit 301. In the sensor unit 105C, resistance may be changed by light emitted from the light emitting unit 301. The sensor unit 105C may have a low resistance or conductivity due to the light emitted from the light emitting unit 301.

The light emitting unit 301 according to an embodiment may be implemented by at least one of a horizontal chip structure, a vertical chip structure, and a flip chip structure, but is not limited thereto. The light emitting unit 301 may include, for example, a light-emitting element. The light-emitting element may include a light-emitting diode (LED), and the LED may emit at least one of ultraviolet light, visible light, and infrared light. The light emitting unit 301 according to the embodiment may emit light having an ultraviolet wavelength of, for example, 400 nm or less or light in a range of 300 nm to 400 nm. In the semiconductor device according to the embodiment, a distance (K1 in FIG. 36) between the light emitting unit 301 and the sensor unit 105C may be five times or less the width C2 of the light emitting unit 301, for example, in a range of 1 to 5 times.

As shown in FIG. 36, in a size of the semiconductor device 100E, a width X11×length Y11 may be, for example, in a range of 300 μm to 5000 μm×300 μm to 5000 μm. When the horizontal length and the longitudinal length of the semiconductor device 100E are 300 μm or more, it may be advantageous for disposing wires of the light emitting unit disposed in the semiconductor device. When the horizontal length and the longitudinal length of the semiconductor device 100E are 5000 μm or less, a module of the semiconductor device 100E may be made small, and thus it may be advantageously applied to various fields. The horizontal length and the longitudinal length of the semiconductor device 100E may be 300 μm to 700 μm in terms of advantageous disposition of the wires, and within the above range, reliability against moisture or other substances contained in heat or air may be ensured. A thickness or a height of the semiconductor device 100E may be 100 μm or more, for example, in a range of 100 μm to 500 μm. A first axis direction on a plane may be a lateral direction or the X-axis direction, and the second axis direction may be a longitudinal direction or the Y-axis direction orthogonal to the X-axis direction. A third axis direction may be a height or a thickness direction, or may be the Z-axis direction orthogonal to the first and second axis directions.

The support member 350 may be a conductive or insulating material. The support member 350 may be a semiconductor material. The support member 350 may be a light-transmitting or non-light-transmitting material. The support member 350 may be selected from the group consisting of a sapphire substrate ($Al_2O_3$), GaN, SiC, ZnO, Si, GaP, InP, $Ga_2O_3$, GaAs, and the like. The support member 350 may be formed of a GaN-based semiconductor, for example, a GaN semiconductor. The support member 350 may be a bulk GaN single crystal substrate. The support member 350 may be used as a support member for supporting the light emitting unit 301 or the semiconductor device. When the support member 350 is a conductive material such as silicon, an insulating layer 352 may be disposed on the support member 350.

A thickness of the support member 350 may be in the range of 30 μm or more, for example, in a range of 30 μm to 300 μm. When the thickness of the support member 350 is smaller than that of the above range, handling during manufacture may be difficult, and when the thickness of the substrate 111 is larger than that of the above range, a size of the semiconductor device may be increased. The support member 350 may include a recess and the recess may pass through the support member 350, and may be disposed so that only a partial region of the support member 350 is exposed, but is not limited thereto. When the thickness of the support member 350 is thicker than 30 μm, problems such as cracking and warping of the support member 350 that may occur in a process of disposing the recesses may be effectively suppressed, and when the thickness of the support member 350 is thinner than 300 μm, problems such as cracking and warping of the support member 350 that may occur due to heat or pressure in a process of disposing the recess on the support member 350 may be effectively suppressed. In the support member 350, a length in a first axis X direction and a length in a second axis Y direction may be the same or different. The length in the first axis direction and the length in the second axis direction of the support member 350 may be a horizontal length and a longitudinal length of the semiconductor device 100E.

The insulating layer 352 may be disposed on the support member 350. The insulating layer 352 may be disposed on an entire upper surface of the support member 350. The insulating layer 352 may be disposed on the upper surface of the support member 350, and may be disposed in a region between the support member 350 and the light emitting unit 301 and in a region between the support member 350 and the sensor unit 105C. The insulating layer 352 may be disposed between the support member 350 and lead electrodes 320 and 330 connected to the light emitting unit 301 and sensor electrodes 151 and 153 of the sensor unit 105C.

The insulating layer 352 may be formed as a single layer or multiple layers by using a dielectric material. The insulating layer 352 includes an insulating material or an insulating resin formed of at least one of an oxide, a nitride, a fluoride, and a sulfide having at least one of Al, Cr, Si, Ti, Zn, and Zr. For example, the insulating layer 352 may be selectively formed of $SiO_2$, $Si_3N_4$, $Al_2O_3$, $TiO_2$, or MgO. A thickness of the insulating layer 352 may be 5 μm or less, for example, in the range of 0.1 μm to 2 μm. When the thickness of the insulating layer 352 is 0.1 μm or more, it is more advantageous for electrically insulating the insulating layer 352, and when the thickness of the insulating layer 352 is 2 μm or less, heat dissipation of the semiconductor device 100E or stress between support member 350 and the light emitting unit 301 and between the support member 350 and the sensor unit 105C may be relaxed and reliability of the semiconductor device 100E may be improved.

The electrode structure according to the third embodiment may be disposed on the support member 350 or the insulating layer 352. The electrode structure may include the lead electrodes 320 and 330 connected to the light emitting unit 301. At least one of the lead electrodes 320 and 330 may be disposed under the light emitting unit 301, and for example, both the first and second lead electrodes 320 and 330 may be disposed thereunder. The first and second lead electrodes 320 and 330 may be electrically connected to the light emitting unit 301. The first and second lead electrodes 320 and 330 may be disposed in a horizontal layer structure. At least one or both of the first and second lead electrodes 320 and 330 may be overlapped with the light emitting unit 301 in the vertical direction.

The first and second lead electrodes 320 and 330 may extend in the horizontal direction of the light emitting unit 301. At least one wire may be disposed on the first and second lead electrodes 320 and 330. In order to dispose the wires, the first and second lead electrodes 320 and 330 may be 300 μm or more in a direction in which the wires are disposed, and may be 700 μm or less. The direction may be a horizontal direction of the support member 350, and may be a longitudinal direction, but is not limited thereto. The first and second lead electrodes 320 and 330 may be equal to a horizontal length or a longitudinal length of the support member 350, and may be disposed to be shorter than the horizontal length or the longitudinal length of the support member 350. However, the invention is not limited thereto. A ratio of the horizontal length or the longitudinal length of the support member 350 to a horizontal length or a longitudinal length of the first and second lead electrodes 320 and 330 may be 1:0.7 to 1:0.95. That is, the horizontal length or the longitudinal length of the first and second lead electrodes 320 and 330 may be 30% to 70% of the horizontal length or the longitudinal length of the support member 350. When the horizontal or longitudinal length of the first and second lead electrodes 320 and 330 is greater than 30% of the horizontal or longitudinal length of the support member 350, it may be advantageous for injecting a current from the first and second lead electrodes 320 and 330 to the light emitting unit 301, and when it is smaller than 70%, it is possible to prevent the first and second lead electrodes 320 and 330 from being damaged when the support member 350 is manufactured as a module.

The first and second lead electrodes 320 and 330 may extend outside a region of the light emitting unit 301. The first and second lead electrodes 320 and 330 may extend in opposite directions on the basis of the light emitting unit 301. The first and second lead electrodes 320 and 330 may be disposed in a recess of the support member 350. In this case, a bottom pad connected to the first and second lead electrodes may be disposed on a lower surface of the support member 350.

The first and second lead electrodes 320 and 330 may be formed of at least one selected from the group consisting of titanium (Ti), copper (Cu), nickel (Ni), gold (Au), chromium (Cr), tantalum (Ta), platinum (Pt), silver (Ag), aluminum (Al), and phosphorus (P), or selective alloys thereof, and may be formed as a single layer or multiple layers. As shown in FIGS. 36 and 39, when the first and second lead electrodes 320 and 330 are multiple layers, bonding layers 321 and 331 may be disposed on the insulating layer 352 or the support member 350, and reflective layers 322 and 332 may be disposed on the bonding layers 321 and 331. The bonding layers 321 and 331 may be bonded between the reflective layers 322 and 332 and the insulating layer 352 or between the reflective layers 322 and 332 and the support member 350, and may be bonded to the light emitting unit 301 by bonding members 341 and 342. The bonding layers 321 and 331 may be a single layer or multiple layers, and in case of the single layer, it may be gold or a gold alloy. For example, the bonding layers 321 and 331 may be disposed in a stacked structure such as an adhesive metal/bonding metal. The adhesive metal may include at least one of Ti, Ni, Cr, Ta, and Pt, and the bonding metal may include Au or Au alloy. The reflective layers 322 and 332 may be a single layer or multiple layers, and in case of a single layer, the reflective layers 322 and 332 may include at least one of aluminum, silver, and gold, and the adhesive metal may be selected from among aluminum, silver and gold. The reflective layers 322 and 332 may be overlapped with an area of the light emitting unit 301 at 10% or less, and may reflect light incident from a circumference of the light emitting unit 301. The reflective layers 322 and 332 may be spaced apart from the bonding members 341 and 342 disposed in lower regions R11 and R12 of the light emitting unit 301. As the reflective layers 322 and 332 are adjacent to the light emitting unit 301, a bonding error may occur. An area of upper surfaces of the reflective layers 322 and 332 may be smaller than that of the bonding layers 321 and 331.

The first and second lead electrodes 320 and 330 may include pads 323 and 333. The pads 323 and 333 may be removed when the bonding layers 322 and 333 are opened and exposed. The pads 323 and 333 of the first and second lead electrodes 320 and 330 may be spaced apart from each other, and for example, may be spaced apart more than a length C1 in a second axis direction of the light emitting unit 301. The pads 323 and 333 may include a first pad 323 disposed on the first reflective layer 321 of the first lead electrode 320 and a second pad 333 disposed on the second reflective layer 332 of the second lead electrode 330. The first and second pads 323 and 333 may be disposed on opposite sides on the basis of the light emitting unit 301. The first and second pads 323 and 333 may be disposed on the first and second bonding layers 321 and 331 of the first and second lead electrodes 320 and 330, respectively, but is not limited thereto.

The first and second pads 323 and 333 may be connected to a connection member, such as a wire, to receive power. The first and second pads 323 and 333 may not be formed separately when the first and second lead electrodes 320 and 330 have a via structure. A top view shape of the first pad 323 and a top view shape of the second pad 333 may be different from each other, and for example, may be selected from a circular shape and a polygonal shape. The first and second lead electrodes 320 and 330 may be disposed to have a long length in the second axis direction, and the light emitting unit 301 may be electrically connected to the first and second lead electrodes 320 and 330 in a boundary region of the first and second lead electrodes 320 and 330.

The widths X2 of the first and second lead electrodes 320 and 330 in the first axis direction may be the same or different from each other, but the invention is not limited thereto. The widths X2 may be greater than a width C2 of the light emitting unit 301.

The light emitting unit 301 includes a light emitting structure layer 120 having the first conductivity type semiconductor layer 121, the active layer 123 and the second conductivity type semiconductor layer 125 as shown in FIGS. 51 and 52. The light emitting unit 301 may include a first electrode 141 connected to the first conductive semiconductor layer 121 and a second electrode 143 connected to the second conductive semiconductor layer 125. The light emitting unit 301 may include a substrate 111. The light emitting structure layer 120 may be disposed on the substrate 111. At least one of the side surfaces of the light emitting unit 301 may correspond to the sensor unit 105C. Here, the configuration of FIG. 51 may be referred to the description of FIG. 14. FIG. 52 is another example of the light emitting unit according to the third embodiment. Referring to FIG. 52, a light emitting unit 301 includes a substrate 221 and a light emitting structure layer 225. The substrate 221 is disposed on the light emitting structure layer 225, and the light emitting structure layer 210 may be disposed on the first and second electrodes 245 and 247. This configuration will be described with reference to FIG. 15 to FIG. 17.

The light emitting unit 301 may be disposed on at least one of the first and second lead electrodes 320 and 330. The light emitting unit 301 may be disposed on the first and second lead electrodes 320 and 330 and a gap region 325 between the first and second lead electrodes 320 and 330, but the present invention is not limited thereto. The same configurations as those in FIGS. 14 and 15 to 17 in the light emitting unit 301 shown in FIGS. 51 and 52 may be referred to the description of FIG. 14 and may be applied to the third embodiment.

An electrode structure of the light emitting unit 301 according to the embodiment may include first and second electrodes 141 and 143, and a conductive layer 114. The first electrode 141 may be electrically connected to the first conductivity type semiconductor layer 121. The first electrode 141 may be implemented as a pad. The first electrode 141 may be disposed under a portion of the first conductivity type semiconductor layer 121. The first electrode 141 may be disposed in a region higher than the second electrode 143 and face the side surface of the active layer 123. The first electrode 141 may be formed of one selected from the group consisting of Ti, Cu, Ni, Au, Cr, Ta, Pt, Sn, Ag, Al, P, or a selective alloy thereof, and may be formed as a single layer or a multilayer.

The second electrode 143 may be disposed under the second conductive semiconductor layer 125. The second electrode 143 may be electrically connected to at least one of the conductive layer 114 and the second conductive semiconductor layer 125. The second electrode 143 may be implemented as a pad. The second electrode 143 may be formed of at least one selected from the group consisting of Ti, Cu, Ni, Au, Cr, Ta, Pt, Sn, Ag, Al, P, or a selective alloy thereof, and may be formed as a single layer or a multilayer. The first and second electrodes 141 and 143 may be spaced apart from each other in the horizontal direction on the light emitting structure layer 120.

The conductive layer 114 may be disposed under the light emitting structure layer 120. The conductive layer 114 is disposed to at least one or both of a region between the second conductivity type semiconductor layer 125 and the second electrode 143 and a region between the first conductivity type semiconductor layer 121 and the first electrode 141. The conductive layer 114 may be disposed under the second conductivity type semiconductor layer 125 and may be electrically connected to the second conductivity type semiconductor layer 125 and the second electrode 143.

The conductive layer 114 may be a transparent layer or a layer of reflective material. The conductive layer 114 may include at least one of a metal, a non-metal, and a semiconductor. The conductive layer 114 may be formed of a metal or an alloy including at least one of metals such as Ag, Ni, Al, Rh, Pd, Ir, Ru, Mg, Zn, Pt, Cu, or may be formed as a single layer or multiple layers. The conductive layer 114 may include at least one of a non-metal such as a metal oxide or a metal nitride. The metal oxide or the metal nitride may be at least one selected from the group consisting of ITO (indium tin oxide), ITO nitride, IZO (indium zinc oxide), IZON nitride, IZTO (indium zinc oxide), IAZO at least one of materials such as indium gallium zinc oxide, IGTO (indium gallium tin oxide), AZO (aluminum zinc oxide), ATO (antimony tin oxide), GZO (gallium zinc oxide), ZnO, IrOx, RuOx. The conductive layer 114 may have a concavo-convex structure to improve light reflection efficiency.

The protective layer 133 may be disposed under the light emitting structure layer 120. The protective layer 133 may be formed of an insulating material. The protective layer 133 may protect the conductive layer 114 and the second electrode 143 and can prevent external moisture penetration and electrical interference. A portion of the protective layer 133 may extend to contact the side surface of the first electrode 141.

The protective layer 133 may be formed of a distributed Bragg reflector (DBR) structure. The DBR structure includes a structure in which two dielectric layers having different refractive indices are alternately arranged. For example, the two dielectric layers may include different layers selected from a SiO$_2$ layer, a Si$_3$N$_4$ layer, a TiO$_2$ layer, an Al$_2$O$_3$ layer, and a MgO layer, respectively.

As shown in FIG. 39, the light emitting unit 301 is a flip chip structure, and at least one of first and second electrodes 141 and 143 may be disposed as a plurality to improve the bonding force and stably support the light emitting unit 301. The light emitting unit 301 may be disposed in a horizontal chip structure as shown in FIG. 40, or a vertical chip structure as shown in FIG. 41.

As shown in FIGS. 35 to 38, the sensor unit 105C may be electrically isolated from the light emitting unit 301, and may be a sensor detecting the presence or absence of gas in response to light emitted from the light emitting unit 301. The sensor unit 105C may be disposed on the insulating layer 352. Here, the insulating layer 352 may be a protective layer of the sensor unit 105C.

The sensor unit 105C may include a plurality of sensor electrodes 151 and 153 and a sensing material 150 connected to the plurality of sensor electrodes 151 and 153.

The plurality of sensor electrodes 151 and 153 may be disposed on the insulating layer 352 or the support member 350. The plurality of sensor electrodes 151 and 153 may include a first sensor electrode 151 and a second sensor electrode 153 separated from each other. The first and second sensor electrodes 151 and 153 may be formed of a metal including at least one of Ag, Ni, Al, Rh, Pd, Ir, Ru, Mg, Zn, Pt, Cu, Au, Hf, Mo, W, TiN, Cr, or alloys thereof, and may be formed as a single layer or multiple layers. The first and second sensor electrodes 151 and 153 may be electrically separated from the first and second lead electrodes 320 and 330. A horizontal or longitudinal length of the first and second sensor electrodes 151 and 153 may be the same as or different from that of the first and second lead electrodes 320 and 330. However, the invention is not limited thereto. The horizontal or longitudinal length of the first and second sensor electrodes 151 and 153 may be in a range of 30% to 70% of the horizontal or longitudinal length of the first and second lead electrodes 320 and 330. When the lengths of the first and second sensor electrodes 151 and 153 are 70% or more of the lengths of the first and second lead electrodes 320 and 330, it is possible to secure a sufficient space for disposing a first pad portion 20 and a second pad portion 40 on the sensor electrodes 151 and 153, and to secure a space for disposing so as to vertically overlap the sensing material 150 and the first and second sensor electrodes 151 and 153. In addition, when the lengths of the first and second sensor electrodes 151 and 153 are 120% or less of the lengths of the first and second lead electrodes 320 and 330, resistance of the first and second sensor electrodes 151 and 153 may be sufficiently lowered.

The first and second sensor electrodes 151 and 153 may extend in the horizontal direction of the sensing material 150. When wires are connected to at least one of the first and second lead electrodes 320 and 330 adjacent to each other, a horizontal or a longitudinal length of the first and second sensor electrodes 151 and 153 may be taken into consideration when the wire is disposed, and may be, for example, 300 μm or more, or 700 μm or less. The first and second sensor electrodes 151 and 153 may be equal to or different from a horizontal length or a longitudinal length of the support member 350, and may be disposed to be shorter than the horizontal length or the longitudinal length of the support member 350. However, the invention is not limited thereto. A ratio of the horizontal length or the longitudinal length of the support member 350 to a horizontal length or a longitudinal length of the first and second sensor electrodes 151 and 153 may be 1:0.7 to 1:0.95. That is, the horizontal length or the longitudinal length of the first and second sensor electrodes 151 and 153 may be 30% to 70% of the horizontal length or the longitudinal length of the support member 350. When the horizontal length or the longitudinal length of the first or second sensor electrode 151 or 153 is greater than 30% of the horizontal length or the longitudinal length of the support member 350, sensing sensitivity by contact with the detection material 150 in the first and second sensor electrodes 151 and 153 may be advantageous, and when it is smaller than 70%, it is possible to prevent the first and second sensor electrodes 151 and 153 from being damaged when the support member 350 is manufactured as a module.

The first sensor electrode 151 may include a first pad portion 20 and a first electrode portion 23 extending from the first pad portion 20 toward the sensing material 150. The first pad portion 20 may be electrically connected to an external terminal, and may be, for example, connected by a wire. The first pad portion 20 may have a thickness greater than that of the first electrode portion 23, or may further include a bonding layer, but the invention is not limited thereto. When the first electrode portion 23 has the bonding layer, the first pad portion 20 may be removed. As shown in FIG. 36, a top view shape of the first pad portion 20 may be a circular shape, an elliptical shape, or polygonal shape. An area of an upper surface of the first pad portion 20 may be, for example, a size that may be bonded to a wire ball or more, and may have a smaller width than a pattern width of the first electrode portion 23.

The second sensor electrode 153 may include a second pad portion 40 and a second electrode portion 43 extending from the second pad portion 40 toward the sensing material 150. The second pad portion 40 may be electrically connected to an external terminal, and may be, for example, connected by a wire. The second pad portion 40 may have a thickness greater than that of the second electrode portion 43, or may further include a bonding layer, but the invention is not limited thereto. When the second electrode portion 43 has a bonding layer, the second pad portion 40 may be removed. A top view shape of the second pad portion 40 may be a circular shape, an elliptical shape, or polygonal shape. An area of an upper surface of the second pad portion 40 may be, for example, a size that may be bonded to a wire ball or more, and may have a smaller width than a pattern width of the second electrode portion 43.

An interval (E3 in FIG. 37) between the first and second sensor electrodes 151 and 153 may be 5 μm or more, for example, in a range of 5 μm to 200 μm. When the interval is larger than the above range, sensing sensitivity is lowered, and when the interval is smaller than the above range, a sensing error may occur due to mutual interference.

The first and second electrode portions 23 and 43 may be formed to a thickness of 100 nm or more, for example, 200 nm or more, but the invention is not limited thereto. The first and second pad portions 20 and 40 may be disposed to be thicker than the first and second electrode portions 23 and 43.

The first electrode portion 23 may extend from the first pad portion 20, and may be in contact with the sensing material 150. The second electrode portion 43 may extend from the second pad portion 40 toward the first electrode portion 23, and may be in contact with the sensing material 150. The first and second electrode portions 23 and 43 may be spaced a predetermined interval E3 apart. The sensing material 150 may be disposed on the first and second electrode portions 23 and 43. A plurality of the first electrode portions 23 may extend in a direction of the second electrode portion 43 or the second pad portion 40. A plurality of the second electrode portions 43 may extend in a direction of the first electrode portion 23 or the first pad portion 20. The plurality of second electrode portions 43 may be disposed between the plurality of first electrode portions 23, respectively. One or more of the first electrode portions 23 may extend in the horizontal direction through a region of the sensing material 150, and one or more of the second electrode portions 43 may extend in the horizontal direction toward the sensing material 150.

The first and second electrode portions 23 and 43 will be described in detail. The first electrode portion 23 has a concave first open region 25, and the second electrode portion has a concave second open region 45. The sensing material 150 may be disposed on the first and second open regions 25 and 45. The first and second open regions 25 and 45 may be regions opened in opposite directions from a gap region 155 between the first and second lead electrodes 320 and 330. For example, in the first open region 25, a part of the first sensor electrode 151 is opened in a direction of the first pad portion 20 from the gap region 155 between the first and second sensor electrodes 151 and 153, and in the second open region 45, a part of the second sensor electrode 153 is opened in a direction of the second pad portion 40 from the gap region 155 between the first and second sensor electrodes 151 and 153. A width E2 of the first and second open regions 25 and 45 may be larger or smaller than a width M2 of the sensing material 150 in the first axis direction. A length between the first and second open regions 25 and 45 may be an interval E1 between a first and second lead electrodes 151 and 153 in the open regions 25 and 45, or may be a distance between the first and second electrode portions 23 and 43. The interval E1 may be less than or equal to a bottom length M1 of the sensing material 150 in the second axis direction. The first and second open regions 25 and 45 adjust the interval E1 between the first and second sensor electrodes 151 and 153 in a region overlapped with the sensing material 150, and thus sensing resistance between the first and second sensor electrodes 151 and 153 by the sensing material 150 may be set.

The first open region 25 of the first sensor electrode 151 may be disposed between first and second protrusions 26 and 27, and the first and second protrusions 26 and 27 may not be overlapped with the sensing material 150 in the vertical direction. The second open region 45 of the second sensor electrode 153 may be disposed between the third and fourth protrusions 46 and 47, and the third and fourth protrusions 46 and 47 may not be overlapped with the sensing material 150.

The sensing material 150 may include a first part 61 overlapped with the first sensor electrode 151, a second part 62 overlapped with the second sensor electrode 153, and a third part 63 not overlapped with the sensor electrodes 151 and 153. The third part 63 may be disposed between the first and second parts 61 and 62. The third part 63 may be disposed to be overlapped with the first and second open regions 25 and 45. As another example, at least one or all of the first to fourth protrusions 26, 27, 46, and 47 may be overlapped and in contact with the sensing material 150 in the vertical direction. Here, a bottom area of the first part 61 or the second part 62 may be smaller than that of the third part 63. A bottom area of the third part 63 may be greater than a sum of the bottom areas of the first and second parts 61 and 62.

A width X13 in the first axial direction of the first and second sensor electrodes 151 and 153 may be greater than the bottom width M2 of the sensing material 150. The width X12 may be equal to or less than the width X13, which may have a relationship of X12≥X13 for electrical and thermal conduction. The interval E1 between the open regions 25 and 45 between the first and second sensor electrodes 151 and 153 may be smaller than the bottom width M1 in the second axis direction of the sensing material 150. Accordingly, the sensing material 150 may be in contact with the first and second sensor electrodes 151 and 153. Since the sensing material 150 is disposed in the open regions 25 and 45 of the first and second sensor electrodes 151 and 153, a contact area with the sensing material 150 may be improved. The bottom width M1 of the sensing material 150 may be disposed to have a long length in the Y-axis direction, and may be disposed to be longer than the length C1 in the Y-axis direction of the light emitting unit 301. For example, it is possible to have a relationship M1≥C1, or a ratio D1:C1 may be in the range of 1:1 to 3:1. Accordingly, a light incidence area in the Y-axis direction in the sensing material 150 may be increased. Alternatively, even though M1≤C1, sensing of the sensing material 150 may be possible.

The first and second sensor electrodes 151 and 153 may include materials such as nanopowder, nanowires, nanorods, carbon nanotubes (CNTs), and graphene, but is not limited thereto.

The sensing material 150 may be disposed in the gap region 155 between the first and second sensor electrodes 151 and 153. The sensing material 150 may be disposed to be overlapped with the first and second electrode portions 23 and 43 in the vertical direction Z. The sensing material 150 may be connected to the first and second sensor electrodes 151 and 153. The sensing material 150 may be in contact with the first and second sensor electrodes 151 and 153. The sensing material 150 may be in contact with the insulating layer 352. The sensing material 150 may be physically separated from the light emitting unit 301. A gap region 325 between the first and second lead electrodes 320 and 330 and the gap region 155 may be disposed on the same straight line in the X-axis direction.

The sensing material 150 may be disposed in a region corresponding to at least one or two side surfaces of side faces of the light emitting unit 301. The sensing material 150 may be disposed in a region not overlapped with the light emitting unit 301 in the vertical direction. The sensing material 150 may be overlapped in the vertical direction on the basis of the light emitting unit 301.

The sensing material 150 may be disposed on the first electrode portion 23 of the first sensor electrode 151 and the second electrode portion 43 of the second sensor electrode 153. The sensing material 150 may be activated by a wavelength of light emitted from the light emitting unit 301 or similar light. Here, in activation, electron-hole pairs may be generated by a wavelength of the light emitted from the light emitting unit 301 or similar light. In the sensing material 150, resistance may be changed by at least 30% or more by incident light, and a generation rate of the electron-hole pairs may become greater according to the incident wavelength and luminous flux.

As shown in FIGS. 36 and 37, the sensing material 150 may be disposed on the first and second electrode portions 23 and 43. The sensing material 150 includes a first part 61 overlapped with the first electrode portion 23 in the vertical direction Z, a second part 52 overlapped with the first electrode portion 43 in the vertical direction, and a third part 53 not overlapped with the first and second electrode portions 23 and 43 in the vertical direction.

The first and second parts 61 and 62 of the sensing material 150 may protrude in opposite directions from the third part 63 disposed in the first and second open regions 25 and 45. The third part 63 may protrude toward the support member. The third part 63 may be disposed between the first and second electrode portions 23 and 43.

An interval E1 between the first and second electrode portions 23 and 43 may be 5 μm or more, for example, in a range of 5 μm to 200 μm. In the first and second electrode portions 23 and 43, when the interval E1 is smaller than the above range, reliability of the sensor may be deteriorated due to interference between the adjacent electrode portions 23 and 43, and when the interval E1 is larger than the above range, a size of the sensor unit 105C may be increased or sensing sensitivity may be lowered. A resistance value for measuring gas may be determined according to the interval E1 between the first and second electrode portions 23 and 43, and as the interval E1 between the first and second electrode portions 23 and 43 is closer, the resistance value of the sensing material 150 may be lower.

As shown in FIG. 53, the sensing material 150 may be in contact with the first and second sensor electrodes 151 and 153 in a region between the first and second sensor electrodes 151 and 153. Since the sensing material 150 has a low resistance or conductivity due to light emitted from the light emitting unit 301, it is possible to electrically connect the adjacent first and second sensor electrodes 151 and 153. The sensing material 150 may have a first resistance due to light L1 incident from the light emitting unit 301, and may be changed to a second resistance lower than the first resistance when an external gas G2 is introduced. Accordingly, the sensing material 150 may reduce the electrical resistance between the first and second sensor electrodes 151 and 153, that is, the first and second electrode portions 23 and 43 by the light L1 and the gas G2, and may electrically connect the first and second sensor electrodes 151 and 153. The first and second sensor electrodes 151 and 153 are electrically connected by the sensing material 150, and the resistance is lowered, and thus the resistance may be detected by the first and second sensor electrodes 151 and 153. A change in the detected resistance may measure the presence or absence of gas by a semiconductor device.

The sensing material 150 may be formed of a metal oxide material. The sensing material 150 may include a main sensing material and a catalyst. The main sensing material comprises a metal oxide material, the catalyst may comprise a metal. The main sensing material may include, for example, at least one or two or more of $SnO_2$, CuO, $TiO_2$, $In_2O_3$, ZnO, $V_2O_5$, $RuO_2$, $WO_3$, $ZrO_2$, $MoO_3$, NiO, CoO, $Fe_2O_3$, and $AB_2O_4$, and may be formed of various materials not limited to this. The catalyst of the sensing material 150 may include, for example, at least one or two or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), Ruthenium (Ru), rhodium (Rh), silver (Ag), hafnium (Hf), tantalum (Ta), tungsten (W), rhenium (Re), iridium (Ir). The catalyst material may be a doping material in the sensing material 150, and mixed with the main sensing material. The sensing material 150 may include a material that may have both of sensing and catalytic properties. The material of the sensing material 150 in accordance with an embodiment of the invention may optionally be mixed with materials of the main sensing material and the catalyst according to the type of gas to be detected. The meaning of sensing by the sensor unit 105C may mean not only the presence or absence of a measurement gas, but also a change in concentration of the measurement gas.

The sensing material 150 is in contact with a surface of the first and second sensor electrodes 151 and 153 to reduce the impendence change. The sensing material 150 may be mixed in one type or two or more types of main sensing material, and doped with one or two types of catalyst materials in the mixed material. The catalyst material may be added in an amount of 5 wt % or less, for example, in a range of 1 wt % to 5 wt % of the main sensing material, and the gas sensing sensitivity may be lowered when the catalyst material exceeds the above range. For example, when $SnO_2$ and ZnO are mixed, in the sensing material 150, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt % to 3 wt % of the main sensing material. Here, since $SnO_2$ has a band gap of about 3.6 eV, a photo current may be formed when light emitted from the light emitting unit 101 is 340 nm. A particle size of the main sensing material is 30 nm or more, for example, in a range of 30 nm to 60 nm. When the particle size is small, characteristics may be improved, but costs may be increased, and when the particle size is larger than the above range, surface energy becomes small, and thus oxygen vacancies may not be formed.

In an operation of the sensor unit 105C according to the embodiment, as shown in FIGS. 36 and 53, when light corresponding to a wavelength of the light L1 emitted from the light emitting unit 301 is irradiated (step ①), electron-hole pairs (EHP) are generated by the sensing material 150 (step ②), at this time, the sensing material 150 may react first with nitrogen or oxygen which occupies the largest composition ratio in the atmosphere (step ③). The nitrogen does not react with the sensing material 150 of the semiconductor device as an inert gas, and oxygen is adsorbed on a surface of the sensing material 150 to be present in a form of oxide ions such as $O^{2-}$, $O_2^-$, and $O^-$. At this time, the oxide ions and the gas G2 to be detected may react with each other to move electrons. At this time, a very large change in impedance, that is, a high sensitivity characteristic, may be shown according to movement of the electrons on the surface of the sensing material 150. That is, the sensing material 150 generates the oxide ions by the reaction of the electrons and oxygen generated in the reaction with the light L1 corresponding to a wavelength of light emitted from the light emitting unit 301, and the oxide ions may react with the gas G2 to be detected to change the movement of the electrons through the sensing material 150. The movement of electrons in the sensing material 150 may change the resistance R between the first and second sensor electrodes 151 and 153, for example, reduce the resistance, and the change in the resistance of the sensing material 150 may be detected by the first and second sensor electrodes 151 and 153. The sensing material 150 may have conductivity by the light L1 corresponding to the wavelength of the light emitted from the light emitting unit. When the gas G2 is sensed, the conductive characteristic may be further improved, for example, and the resistance of the sensing material 150 may be further lower or higher. Accordingly, the first and second sensor electrodes 151 and 153 may be electrically connected by the sensing material 150. As shown in FIG. 54, a sensing resistance level of the semiconductor device may be changed to low/high according to on/off of the ultraviolet rays (UV). The gas may include $H_2$, $CO_2$, CO, HCl, $Cl_2$, $H_2S$, $H_2$, HCN, $NH_3$, $C_3H_8$, $C_4H_{10}$, $CH_4$, and the like. The sensing material 150 may have an impedance value in a range of several hundreds of KΩ to several tens of MΩ through a process and heat treatment as a semiconductor ceramic material. The semiconductor device 100E including the sensing material 150 may be variously applied to detect a material. For example, although the semiconductor device 100E is used for detecting gas in the above embodiment, it is possible to be used for detecting light and to be used for detecting other chemicals, but the invention is not limited thereto.

Since the sensor unit 105C and the light emitting unit 301 according to an embodiment are disposed on different regions of the support member 350, light emitted from the light emitting unit 301 may be incident on the sensor unit 105C and incidence efficiency of the light may be increased, and thus operational reliability of the sensor unit 105C may be improved.

Since the sensor unit 105C according to an embodiment is disposed adjacent to the light emitting unit 301 or in a region adjacent to the active layer 123 of the light emitting unit 301, intensity of light to be irradiated may be stably provided. Since a distance K1 between the sensing material 150 of the sensor unit 105C and the light emitting unit 301 is 2000 µm or less, for example, in a range of 500 µm to 2000 µm, a decrease in a light amount and light intensity of light irradiated in a direction of the sensing material 150 may be minimized, and sensing sensitivity may be improved. Accordingly, reliability of sensing sensitivity of a semiconductor device having the sensor unit 105C and the light emitting unit 301 on the support member may be improved.

The sensing material 150 of the sensor unit 105C according to an embodiment may change the resistance between the first and second sensor electrodes 151 and 153 to detect the presence or absence of gas sensing by the first and second sensor electrodes 151 and 153. For example, when gas is detected in the sensing material 150, a resistance value is lowered, and the resistance value may be detected by the first and second sensor electrodes 151 and 153. Alternatively, when gas is not detected in the sensing material 150, the sensing material 150 may be an insulation resistance. When a change in the resistance value of the sensing material 150 is changed by about 2%, it is possible to detect whether the gas is sensed by the first and second sensor electrodes 151 and 153.

A semiconductor device 100E according to an embodiment uses the light of the light emitting unit 301, so that costs may be reduced. Since a heater is not used, it is possible to prevent a deterioration in reliability against thermal shock, and to reduce complex problems of microelectromechanical systems (MEMS) processes due to a membrane structure or a packaging. Since the semiconductor device according to the first embodiment includes the sensor unit 105C for detecting gas and the light emitting unit 301 disposed in regions adjacent to each other, packaging of the semiconductor device may be facilitated. Even though a bottom of the sensing material 150 is disposed to contact only a region between the first and second electrode portions 23 and 43, the sensor unit 105C according to the embodiment may detect a change in resistance by the sensing material 150.

When the light emitting unit 301 according to an embodiment emits ultraviolet light, an ultraviolet LED chip has a characteristic that light output of an edge portion is lower than that of a center region. Accordingly, the sensing material 150 may be disposed to correspond to a center region of a side surface of the light emitting unit 301 rather than a peripheral region thereof. The peripheral region may include a region adjacent to each edge of the light emitting unit 301.

Since the first and second sensor electrodes 151 and 153 are separated from the light emitting unit 301 or separated from the first and second lead electrodes 320 and 330, the first and second pad portions 20 and 40 of the sensor unit 105C may be freely disposed.

FIG. 40 is a first modification example of a light emitting unit. The light emitting unit 301A may be a horizontal LED, and may be connected to first and second lead electrodes 320 and 330 through wires 1 and 2. The light emitting unit 301A may be disposed on the same center line as a center of the sensing material 150. The light emitting unit 301A may be disposed on any one of the first and second lead electrodes 320 and 330, and may be, for example, disposed on the first lead electrode 320 and connected to the first and second lead electrodes 320 and 330 through the wires 1 and 2. In this case, an area of the first lead electrode 320 may be larger than that of the second lead electrode 330, and a gap region 325 between the first and second lead electrodes 320 and 330 may be spaced apart from the light emitting unit 301A. A gap region 155 and the gap region 325 between the first and second lead electrodes 320 and 330 may be disposed on another straight line in the X-axis direction.

FIG. 41 is a second modification example of a light emitting unit. The light emitting unit 301B may be a vertical LED, and may be connected to a first lead electrode 320 by a bonding member and may be connected to a second lead electrode 330 by a wire 2. The light emitting unit 301B may be disposed on the same center line as a center of the sensing material 150. The light emitting unit 301B may be disposed on any one of the first and second lead electrodes 320 and 330, and may be, for example, disposed on the first lead electrode 320 and connected to the second lead electrode 330 by the wire 2. In this case, an area of the first lead electrode 320 may be larger than that of the second lead electrode 330, and a gap region 325 between the first and second lead electrodes 320 and 330 may be spaced apart from the light emitting unit 301B. A gap region 155 and the gap region 325 between the first and second lead electrodes 320 and 330 may be disposed on another straight line in the X-axis direction.

FIG. 42 is a modification example of the semiconductor device of FIG. 36, and a bonding region 325A of a first lead electrode 320 and a bonding region 335A of a second lead electrode 330 may extend to be overlapped to both sides in the X-axis direction. Accordingly, the light emitting unit 301 may be disposed on the bonding regions 325A and 335A of the first and second lead electrodes 320 and 330 in the X-axis direction. The light emitting unit 301 may be connected to the bonding regions 325A and 335A of the first and second lead electrodes 320 and 330 by a flip chip. In this case, a gap region 325 between the first and second lead electrodes 320 and 330 may be disposed along between the bonding regions 325A and 335A of the first and second lead electrodes 320 and 330.

A sensor unit 105C includes first and second sensor electrodes 151 and 153 and a sensing material 150.

A first electrode portion 23 of the first sensor electrode 151 may have a protrusion part 26A protruding in a first side direction of the sensing material 150, and a second electrode portion 43 of the second sensor electrode 153 may have a protrusion part 46A protruding in a second side direction of the sensing material 150. The protrusion parts 26A and 46A of the first and second sensor electrodes 151 and 153 may be disposed in both sides of the sensing material 150, and may be disposed, for example, at both sides in the Y axis direction. The sensing material 150 may be disposed on a region 155A between the protrusion parts 26A and 46A of the first and second sensor electrodes 151 and 153, and may be in contact with at least one of the first and second electrode portion 23 and 43 and/or at least one of the protrusion parts 26A and 46A. The protrusion parts 26A and 46A and the sensing material 150 may be disposed to be overlapped in the X-axis direction. Here, the sensing material 150 may have a long length in the Y-axis direction, and may be disposed on at least one side of the light emitting unit 301.

The gap region 155 and a gap region 325 between the first and second lead electrodes 320 and 330 may be disposed on another straight line in the X-axis direction.

FIG. 43 is a modification example of a sensor electrode in the semiconductor device of FIG. 37. Referring to FIG. 43, a sensor unit 105C may include first and second sensor electrodes 151 and 153 and a sensing material 150. The first sensor electrode 151 may include a protrusion 28 protruding in a direction of a first open region 25 between protrusion parts 26 and 27. The second sensor electrode 153 may be disposed between protrusion parts 46 and 47, and may include a protrusion 48 protruding in a direction of a second open region 45.

An interval between the protrusions 28 and 48 may be smaller than that of E3 between the first and second open regions 25 and 45. The protrusions 28 and 48 may protrude in a direction of the sensing material 150, for example, in a direction of a third part 63 of the sensing material 150. Accordingly, an area of the sensing material 150 in contact with the first and second sensor electrodes 151 and 153 may be increased. A width of the sensing material 150 in the X-axis direction may be disposed larger than that of the protrusions 28 and 48 in the X-axis direction.

FIG. 44 is a modification example of the first and second sensor electrodes of the sensor unit 105C of FIG. 36. A first sensor electrode 151 may include one or a plurality of patterns 24 extending in the X-axis direction in a first open region 25, and a second sensor electrode 153 may include one or a plurality of patterns 44 extending in the X-axis direction in a second open region 45. Here, a sensing material 150 may be disposed to have a long length in the Y-axis direction, and may be overlapped with the patterns 24 and 44 of the first and second sensor electrodes 151 and 153 in the vertical direction. The sensing material 150 may be in contact with the patterns 24 and 44 of the first and second sensor electrodes 151 and 153 in the first and second open regions 25 and 45. A change in resistance between the first and second sensor electrodes 151 and 153 may be detected by a contact of the sensing material 150. The patterns 24,44 may have a predetermined interval or different intervals.

FIG. 45 is a modification example of the first and second sensor electrodes of the sensor unit 105C in FIG. 36. A first sensor electrode 151 may include one or a plurality of patterns 24A extending in the Y-axis direction in a first open region 25, and a second sensor electrode 153 may include one or a plurality of patterns 44A extending in the Y-axis direction in a second open region 45. Here, the sensing material 150 may be disposed to have a long length in the Y-axis direction, and may be overlapped with the patterns 24A and 44A of the first and second sensor electrodes 151 and 153 in the vertical direction. The sensing material 150 may be in contact with the patterns 24A and 44A of the first and second sensor electrodes 151 and 153 in the first and second open regions 25 and 45. A change in resistance between the first and second sensor electrodes 151 and 153 may be detected by a contact of the sensing material 150. Lengths of the patterns 24A and 44A of the first and second sensor electrodes 151 and 153 in the Y-axis direction may be smaller than a length of each of the first and second open regions 25 and 45.

FIG. 46 is a modification example of the semiconductor device of FIG. 36, and is an example including a plurality of sensor units. Any one of the plurality of sensor units 105C and 105D will be defined and described as the above-mentioned sensor unit, and the same parts as the sensor unit are processed to the same reference numerals and will be used for explanation.

Referring to FIG. 46, a semiconductor device 100F may include a light emitting part 301 on a first region of a support member 350, the first sensor unit 105C on a second region, and the second sensor unit 105D on a third region. The first sensor unit 105D or the second sensor unit 105D refers to the sensor unit disclosed above.

The light emitting unit 301, the first sensor unit 105C and the second sensor unit 105D may be disposed on different regions of the support member 350. The light emitting unit 301 may be disposed between the first sensor unit 105C and the second sensor unit 105D. The light emitting unit 301 may be disposed between first and second sensing materials 150 and 150A. The first and second sensor units 105C and 105D may be disposed in regions corresponding to different side surfaces of the light emitting unit 301. The first and second sensor units 105C and 105D may be disposed in regions corresponding to at least two side surfaces of the light emitting unit 301. The first and second sensor units 105C and 105D may be disposed in regions corresponding to opposite side surfaces of the light emitting unit 301. The first and second sensing materials 150 and 150A may be disposed on opposite side surfaces or different side surfaces of the light emitting unit 301.

A distance between the first sensor unit 105C and the second sensor unit 105D may be larger than a distance between the light emitting part 301 and the first sensor unit 105C, and may be larger than a distance between the light emitting part 301 and the second parts 105D.

The first sensor unit 105C may include first and second sensor electrodes 151 and 153 and the first sensing material 150, and the first sensing material 150 may be connected to or in contact with the first and second sensor electrodes 151 and 153. In an open region in which the first sensing material 150 is disposed, a distance E1 between electrode portions 23 and 43 of the first and second sensor electrodes 151 and 153 may be smaller than or equal to a length M1 of the first sensing material 150 in the Y-axis direction.

The first sensor unit 105D may include third and fourth sensor electrodes 151A and 153A and the second sensing material 150A, and the second sensing material 150A may be connected to or in contact with the third and fourth sensor electrodes 151A and 153A. In an open region in which the second sensing material 150A is disposed, a distance E11 between electrode portions 23A and 43A of the third and fourth sensor electrodes 151A and 153A may be smaller than or equal to a length M11 of the second sensing material 150A in the Y-axis direction. The distances E1 and E11 may be equal to or different from each other. The first to fourth sensor electrodes 151, 153, 151A, and 153A refer to description of the sensor electrodes disclosed above, and may be selectively used to the same configuration.

The first and second sensing materials 150 and 150A may be equal to or different from each other. In this case, when the first and second sensing materials 150 and 150A are different, it is possible to detect by sensing different gases.

The first and second sensing materials 150 and 150A may be formed of a metal oxide material. The first and second sensing materials 150 and 150A may include a main sensing material and a catalyst. The main sensing material comprises a metal oxide material, the catalyst may comprise a metal.

The main sensing material may include, for example, at least one or two or more of $SnO_2$, CuO, $TiO_2$, $In_2O_3$, ZnO, $V_2O_5$, $RuO_2$, $WO_3$, $ZrO_2$, $MoO_3$, NiO, CoO, $Fe_2O_3$, and $AB_2O_4$, and may be formed of various materials not limited to this. The catalyst of the first and second sensing materials 150 and 150A may include, for example, at least one or two or more of platinum (Pt), copper (Cu), rhodium (Rd), gold (Au), palladium (Pd), iron (Fe), titanium (Ti), vanadium (V), chromium (Cr), nickel (Ni), aluminum (Al), zirconium (Zr), niobium (Nb), molybdenum (Mo), Ruthenium (Ru), rhodium (Rh), silver (Ag), hafnium (Hf), tantalum (Ta), tungsten (W), rhenium (Re), iridium (Ir). The catalyst material may be a doping material in the first and second sensing materials 150 and 150A, and mixed with the main sensing material. The first and second sensing material 150 and 150A may include a material that may have both of sensing and catalytic properties. The material of the first and second sensing materials 150 and 150A in accordance with an embodiment of the invention may optionally be mixed with materials of the main sensing material and the catalyst according to the type of gas to be detected.

The first sensing material 150 is in contact with a surface of the first and second sensor electrodes 151 and 153 to reduce the impendence change. The second sensing material 150A is in contact with a surface of the first and second sensor electrodes 151A and 153A to reduce the impendence change. The first and second sensing materials 150 and 150A may be mixed in one type or two or more types of main sensing material, and doped with one or two types of catalyst materials in the mixed material. The catalyst material may be added in an amount of 5 wt % or less, for example, in a range of 1 wt % to 5 wt % of the main sensing material, and the gas sensing sensitivity may be lowered when the catalyst material exceeds the above range. For example, when $SnO_2$ and ZnO are mixed, in one of the first and second sensing materials 150 and 150A, $SnO_2$ may be mixed at a larger ratio than ZnO, for example, $SnO_2$:ZnO may be mixed at a molar ratio of 1:2.5 to 2.5:1, and the catalyst material may be doped with, for example, platinum (Pt) in a range of 1 wt % to 3 wt % of the main sensing material. Here, since $SnO_2$ has a band gap of about 3.6 eV, a photo current may be formed when light emitted from the light emitting unit 101 is 340 nm. A particle size of the main sensing material is 30 nm or more, for example, in a range of 30 nm to 60 nm. When the particle size is small, characteristics may be improved, but costs may be increased, and when the particle size is larger than the above range, surface energy becomes small, and thus oxygen vacancies may not be formed.

In sensor units 105C and 105D according to an embodiment, when light L1 from a light emitting unit 301 is emitted, electrons are generated by the first and second sensing materials 150 and 150A, and oxygen is adsorbed on surfaces of the sensing materials 150 and 150A to be present in a form of oxide ions such as $O^{2-}$, $O_{2-}$, and $O^-$. At this time, the oxide ions may react with gas to move electrons. At this time, a very large change in impedance, that is, high sensitivity characteristic, may be shown according to movement of the electrons on the surfaces of the sensing materials 150 and 150A. That is, the sensing materials 150 and 150A generates oxide ions by reaction of the electrons and oxygen generated in reaction with light, and the generated oxide ions may react with the gas to move the electrons through the sensing materials 150 and 150A. The movement of electrons in the sensing materials 150 and 150A may change resistance between first and second sensor electrodes 151 and 153 and resistance between third and fourth sensor electrodes 151A and 153A. For example, reduce the resistance. The change in the resistance of the sensing materials 150 and 150A may be detected by the sensor electrodes in the sensor units 105C and 105D.

FIG. 47 is a modification example of the support member in the semiconductor device of FIG. 36 according to the third embodiment.

Referring to FIG. 37, a semiconductor device may have a concave recess 350A on an upper portion of a support member 350, and the light emitting unit 301 may be disposed at the recess 350A. A depth H1 of the recess 350A may be half or less of a thickness T11 of the support member 350. An upper surface of the light emitting unit 301 may be disposed at a lower height than the structure of FIG. 39. A sensor unit may be disposed on a side surface of the light emitting part 301 to emit light emitted from the light emitting part 301 to the sensor unit. A bottom area of the recess 350A may be larger than that of the light emitting part 301, and a periphery of the recess 350A may be an inclined plane or a vertical plane. As another example, the recess 350A of the support member 350 may be disposed under a sensor unit, for example, under a sensing material, not under a light emitting unit.

A width of the recess 350A may be gradually narrower toward a bottom, and first and second lead electrodes 320 and 330 may be disposed on the bottom and a side surface of the recess 350A to be electrically connected to the light emitting unit 301.

The insulating layer 352 may be disposed between the first and second lead electrodes 320 and 330 disposed in the recess 350A and the support member 350, but the invention is not limited thereto.

FIG. 48 is a modification example of the support member in the semiconductor device of FIG. 46 according to the third embodiment.

Referring to FIG. 48, a semiconductor device may have a concave recess 350A on an upper portion of a support member 350, and the light emitting unit 301 may be disposed at the recess 350A. A depth H1 of the recess 350A may be half or less of a thickness T11 of the support member 350. An upper surface of the light emitting unit 301 may be disposed at a lower height than the structure of FIG. 5. Sensor units 105C and 105D may be disposed on different side surfaces of the light emitting part 301 to emit light emitted from the light emitting part 301 to the sensor units 105C and 105D.

A bottom area of the recess 350A may be larger than that of the light emitting part 301, and a periphery of the recess 350A may be an inclined plane or a vertical plane. A width of the recess 350A may be gradually narrower toward a bottom, and first and second lead electrodes 320 and 330 may be disposed on the bottom and a side surface of the recess 350A to be electrically connected to the light emitting unit 301.

The insulating layer 352 may be disposed between the first and second lead electrodes 320 and 330 disposed in the recess 350A and the support member 350, but the invention is not limited thereto.

FIG. 49 is an exploded perspective view of the sensing device having the semiconductor device according to the third embodiment of the invention, and FIG. 50 is a side cross-sectional view of the sensing device of FIG. 49. The semiconductor device applies an example of the semiconductor device of FIG. 46, and the semiconductor device and another element as shown in FIG. 35 may be selectively applied thereto.

Referring to FIGS. 49 and 50, a sensing device may include a package body 660, a semiconductor device 100F disclosed in an embodiment in a cavity 665 of the package body 660, and a reflective plate 570 on the semiconductor device 100F.

The package body 660 may include at least one of a resin PCB, a metal core PCB (MCPCB), and a flexible PCB (FPCB), but the invention is not limited thereto. The package body 660 may include a ceramic material. An external size of the package body 660 may be at least one side of 6 mm or more, for example, in a range of 6 mm to 12 mm×5 mm to 12 mm.

The package body 660 may have the cavity 665, and the semiconductor device 100F may be disposed in the cavity 665. A depth of the cavity 665 may be at least 1 mm or more, for example, in a range of 1 mm to 3 mm. A horizontal length and a longitudinal length of the cavity 665 may be at least 4 mm or more, for example, in a range of 4 mm to 10 mm.

A plurality of lead patterns 91, 92, 93, 94, 95, and 96 may be disposed on a bottom of the cavity 665, and the plurality of lead patterns 91, 92, 93, 94, 95, and 96 may be electrically connected to pad portions 20, 40, 20A, 40A, 323, and 333 of the semiconductor device 100F by a connection member such as a wire 669. The lead pattern 91 disposed at a center of the bottom of the cavity 665 may have an area equal to or larger than that of the semiconductor device 100F to be bonded to the semiconductor device 100F by an adhesive.

Lower patterns 91A, 96A and 97A may be disposed on a bottom of the package body 660, and may be connected to the lead pattern 91 in a via structure 90. It is possible to supply power through the lower patterns 91A, 96A, and 97A, or detect sensing resistance.

The package body 660 may be disposed around the semiconductor device 100F to reflect light emitted from a light emitting unit 301 of the semiconductor device 100F and dissipate heat conducted from the semiconductor device 100F. The package body 660 may be disposed on a circuit board, or coupled to another structure. In the embodiment, the semiconductor device 100F may include one or a plurality of sensor units 105C and 105D. When the plurality of sensor units 105C and 105D are provided, it is possible to detect different gases or improve sensing sensitivity.

A stepped structure 662 may be disposed on the package body 660. A reflective plate 570 may be disposed on the stepped structure 662. The reflective plate 570 may reflect light to prevent leakage of light. The reflective plate 570 may be closely coupled on or adhered to the stepped structure 662 of the package body 660. The reflective plate 570 may be in contact with the package body 660 with an adhesive (not shown). The sensor unit 105C may sense an exposing gas due to light emitted from the light emitting unit 301 and gas introduced through an opening part 572 of the reflective plate 570, for example, a harmful gas. The opening parts 572 may be disposed in one or plural.

Since the light emitting unit 301 and the sensor unit 105C are disposed in different regions of the semiconductor device 100F, a configuration of another embodiment disclosed above may be applied selectively. In an embodiment, any one of first and second sensor electrodes 151 and 153 of the sensor unit may be commonly connected to the light emitting unit 301, for example, the first sensor electrode 151 and a first electrode may be connected in common, but the invention is not limited thereto.

As another example, in an embodiment, a light emitting unit 301 is configured as one, but disposed in plural, and a sensor unit 105C may be disposed between the plurality of light emitting units, or the sensor unit may be disposed outside different light emitting units, respectively. The plurality of light emitting units may emit the same wavelength or different wavelengths.

Whether gas sensed by a sensing device having a semiconductor device according to an embodiment is sensed or not, may be detected by a signal processing circuit, and it is possible to transmit through a transmission module by wired or wireless communication, or inform a user through an output module by an alarm or a display mode.

FIGS. 51 and 52 show examples of a semiconductor device, and will be described with reference to FIGS. 14 and 15 to 17.

According to an embodiment of the invention, a second sensor unit may include on a third region of the supporting member, and the second sensor unit may include a second sensing material and third and fourth sensor electrodes contacted with the second sensing material.

According to an embodiment of the invention, the first and second sensing materials may be disposed on at least two side surfaces of the plurality of side surfaces of the light emitting unit.

According to an embodiment of the invention, a first lead electrode and a second lead electrode electrically connected to the light emitting unit may be disposed on the support member, and the first lead electrode and the second lead electrode may be electrically separated from the first and second sensor electrodes. An insulating layer may be disposed on the supporting member, and the insulating layer may be disposed between the supporting member and the first and second lead electrodes, and between the supporting member and the first and second sensor electrodes.

According to an embodiment of the invention, the light emitting unit may be disposed between the first and second sensing materials.

According to an embodiment of the invention, a first lead electrode and a second lead electrode electrically connected to the light emitting unit may be disposed on the support member, and the first lead electrode and the second lead electrode may be electrically separated from the first and second sensor electrodes.

According to an embodiment of the invention, an insulating layer may be disposed on the supporting member, and the insulating layer may be disposed between the supporting member and the first and second lead electrodes, and between the supporting member and the first and second sensor electrodes.

According to an embodiment of the invention, at least one of the first and second electrode portions may include a protrusion part extending to at least one side surface or both side surfaces of the sensing material. The first and second electrode portions may have first and second open regions opened in opposite directions from a gap region between the first and second sensor electrodes, and the first sensing material may be disposed in the first and second open regions. A distance between the first and second sensor electrodes in the first and second open regions may be greater than a width of the gap region, and smaller than a bottom length in a second axis direction of the first sensing material.

According to an embodiment of the invention, the first and second electrode portions may include at least one pattern extending in a direction of the first and second open regions. A length in the second axis direction of the first sensing material may be greater than a length in the second axis direction of the light emitting unit. The first sensor electrode may have a first pad portion, the second sensor electrode may have a second pad portion, and the first sensing material may be disposed between the first and second pad portions. The light emitting unit may be an LED including a substrate and first and second electrodes under the light emitting structure layer, and the substrate may be disposed on the light emitting structure layer. The light emitting unit may include a vertical or horizontal LED. The light emitting unit may emit ultraviolet light. The support member may include a substrate of an insulating or conductive material. A concave recess may be disposed on an upper portion of the support member, and the light emitting unit may be disposed in the recess.

According to an embodiment of the invention, first and second lead electrodes may be electrically connected to the light emitting unit on the support member, and a plurality of electrode patterns may be formed on a bottom of the cavity, and the first and second lead electrodes and the first and second sensor electrodes may be electrically connected to the plurality of electrode patterns.

According to an embodiment of the invention, a second sensor unit may be disposed on a third region of the support member, the package body may include a ceramic material, a plurality of lower patterns may be formed on a bottom of the package body, and the electrode pattern may be electrically connected to the lower pattern.

In the invention, the first to fourth embodiments disclosed above, other examples, and modification examples of the first to third embodiments may be selectively combined with or modified from each other.

Whether gas sensed by a sensing device having a semiconductor device according to an embodiment is sensed or not, may be detected by a signal processing circuit, and it is possible to transmit through a transmission module by wired or wireless communication, or inform a user through an output module by an alarm or a display mode.

A semiconductor device or a sensing device according to an embodiment may be applied to a place or a device in which gas such as various kinds of toxic gas or explosive gas is generated, for example, a moving device such as an interior of a vehicle or a vehicle lamp, or an enclosed space. Alternatively, it may be applied to indoor or outdoor sensing devices.

The characteristics, structures and effects described in the above-described embodiments are included in at least one embodiment but are not limited to one embodiment. Furthermore, the characteristic, structure, and effect illustrated in each embodiment may be combined or modified for other embodiments by a person skilled in the art. Thus, it would be construed that contents related to such a combination and such a modified example are included in the scope of the invention.

In addition, embodiments are mostly described above. However, they are only examples and do not limit the invention. A person skilled in the art may appreciate that several variations and applications not presented above may be made without departing from the essential characteristics of the embodiments. For example, each component particularly represented in the embodiments may be varied. In addition, it should be construed that differences related to such a variation and such an application are included in the scope of the invention defined in the following claims.

The invention claimed is:

1. A semiconductor device comprising:
a support member;
a light emitting unit on a first region of the support member;
a first sensor unit is disposed on a second region of the support member; and
an insulating layer disposed between the light emitting unit and the support member and between the support member and the first sensor unit,
wherein the light emitting unit includes a light emitting structure layer having a first conductivity type semiconductor layer, a second conductivity type semiconductor layer, and an active layer between the first conductivity type semiconductor layer and the second conductivity type semiconductor layer,
wherein the first sensor unit includes at least one first sensing material activated by light emitted from the light emitting unit, a first sensor electrode including a first electrode portion contacted to the first sensing material, and a second sensor electrode including a second electrode portion contacted to the first sensing material,
wherein the first electrode portion is spaced apart from the second electrode portion,
wherein the first sensing material is disposed on the first electrode portion and the second electrode portion, and
wherein the first sensing material includes a first part overlapped with the first electrode portion in a vertical direction, a second part overlapped with the second electrode portion in the vertical direction, and a third part not overlapped with the first and second electrode portions in the vertical direction between the first and second electrode portions.

2. The semiconductor device of claim 1, wherein the light emitting unit generates an ultraviolet light and the first sensing material reacts by the ultraviolet light.

3. The semiconductor device of claim 1, wherein the light emitting unit further includes a first electrode connected to the first conductivity type semiconductor layer and a second electrode connected to the second conductivity type semiconductor layer, and
wherein the first and second sensor electrodes are electrically separated from the first and second electrodes.

4. The semiconductor device of claim 1, wherein the first sensing material includes a main sensing material and a catalyst,
wherein the main sensing material includes at least one or more of $SnO_2$, $CuO$, $TiO_2$, $In_2O_3$, $ZnO$, $V_2O_5$, $RuO_2$, $WO_3$, $ZrO_2$, $MoO_3$, $NiO$, $CoO$, $Fe_2O_3$, and $AB_2O_4$, and
wherein the catalyst includes at least one or more of platinum (Pt), copper (Cu), gold (Au), palladium (Pd), iron (Fe), titanium (Ti), vanadium (V), chromium (Cr), nickel (Ni), aluminum (Al), zirconium (Zr), niobium (Nb), molybdenum (Mo), ruthenium (Ru), rhodium (Rh), silver (Ag), hafnium (Hf), tantalum (Ta), tungsten (W), rhenium (Re), and iridium (Ir).

5. A sensing device comprising:
a circuit board;
a package body disposed on the circuit board and including a cavity;
the semiconductor device of claim 1 including the first sensor unit and the light emitting unit disposed in the cavity; and
a reflective plate having an opening part on the cavity,
wherein the light emitting unit generates an ultraviolet light,
wherein the first sensor unit includes the first sensing material, and
wherein the first sensing material of the first sensor unit reacts by the ultraviolet light.

6. The semiconductor device according to claim 1, further comprising a plurality of lead electrodes including a bonding layer on the insulating layer and a reflective layer on the bonding layer, wherein the first and second sensor electrodes are disposed on the insulating layer, and wherein each of the plurality of lead electrodes and each of the first and second sensor electrodes are spaced from a side surface of the support member.

7. The semiconductor device of claim 6, wherein each of the plurality of lead electrodes extends outwardly from a side surface of the light emitting unit, and wherein an area of the reflective layer overlaps an area of the light emitting unit by 10% or less in the vertical direction.

8. The semiconductor device of claim 1, further comprising a second sensor unit disposed on a third region of the support member, wherein the second sensor unit includes a second sensing material, and a third sensor electrode and a fourth sensor electrode contacted to the second sensing material.

9. The semiconductor device of claim 8, wherein the first sensing material and the second sensing material are disposed on at least two side surfaces of the light emitting unit.

\* \* \* \* \*